US010711289B2

(12) United States Patent
Suominen et al.

(10) Patent No.: US 10,711,289 B2
(45) Date of Patent: Jul. 14, 2020

(54) METHOD OF PRODUCING AND PROCESSING DIAMINES FROM AN ENGINEERED MICROORGANISM

(71) Applicant: Genomatica, Inc., California, CA (US)

(72) Inventors: Lauri H. Suominen, San Diego, CA (US); Connor J. Galleher, San Diego, CA (US); Michael Japs, San Diego, CA (US); Mark J. Burk, San Diego, CA (US); Cara Tracewell, San Diego, CA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 15/538,448

(22) PCT Filed: Dec. 22, 2015

(86) PCT No.: PCT/US2015/067478
§ 371 (c)(1),
(2) Date: Jun. 21, 2017

(87) PCT Pub. No.: WO2016/106367
PCT Pub. Date: Jun. 30, 2016

(65) Prior Publication Data
US 2017/0369913 A1  Dec. 28, 2017

Related U.S. Application Data

(60) Provisional application No. 62/096,309, filed on Dec. 23, 2014, provisional application No. 62/193,693, filed on Jul. 17, 2015, provisional application No. 62/211,315, filed on Aug. 28, 2015.

(51) Int. Cl.
| | | |
|---|---|---|
| C12P 13/00 | (2006.01) |
| C12N 11/16 | (2006.01) |
| C12N 9/96 | (2006.01) |
| C12N 9/88 | (2006.01) |
| C12N 1/20 | (2006.01) |
| C12N 15/52 | (2006.01) |
| C12N 1/02 | (2006.01) |

(52) U.S. Cl.
CPC .............. *C12P 13/001* (2013.01); *C12N 1/02* (2013.01); *C12N 1/20* (2013.01); *C12N 9/88* (2013.01); *C12N 9/96* (2013.01); *C12N 11/16* (2013.01); *C12N 15/52* (2013.01); *C12Y 402/01001* (2013.01)

(58) Field of Classification Search
None
See application file for complete search history.

(56) References Cited

U.S. PATENT DOCUMENTS

| 8,509,617 B2 | 8/2013 | Cao |
| 9,458,480 B2 | 10/2016 | Burk et al. |
| 2009/0246838 A1* | 10/2009 | Zelder ............... C12N 9/88 435/128 |

FOREIGN PATENT DOCUMENTS

| CN | 102056889 A | 5/2011 |
| JP | 2004 222569 A | 8/2004 |
| WO | 2007/113127 A1 | 10/2007 |
| WO | 2009/092793 A2 | 7/2009 |
| WO | 2012/114256 A1 | 8/2012 |
| WO | 2015/152541 A1 | 10/2015 |

OTHER PUBLICATIONS

Jo et al. Appl Environ Microbiol. Nov. 2013;79(21):6697-705. Epub Aug. 23, 2013. (Year: 2013).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Bover-Cid, Sara et al., "Improved Screening Procedure for Biogenic Amine Production by Lactic Acid Bacteria", International Journal of Food Microbiology, 53, 1999, 33-41.
International Search Report, International Application No. PCT/US2015/067478, 8 pages, dated Apr. 5, 2016.
Merlin et al. (2003) "Why is Carbonic Anhydrase Essential to *Escherichia coli*?", Journal of Bacteriology, 185(21):6415-6424.

* cited by examiner

*Primary Examiner* — Christian L Fronda
(74) *Attorney, Agent, or Firm* — Kagan Binder PLLC

(57) ABSTRACT

Provided is a method of producing and isolating a diamine produced by microbial fermentation that minimizes undesirable salt formation to provide a lower cost process.

10 Claims, 36 Drawing Sheets
Specification includes a Sequence Listing.

SEQUENCE LISTING

```
<160> NUMBER OF SEQ ID NOS: 15

<210> SEQ ID NO 1
<211> LENGTH: 242
<212> TYPE: PRT
<213> ORGANISM: Desulfovibrio vulgaris str. Miyazaki F

<400> SEQUENCE: 1

Met Arg Leu Arg Phe Leu Ser Ala Leu Phe Leu Val Val Ala Met Val
1               5                   10                  15

Gly Thr Ala Leu Ala Gly Ser Thr Gly Pro Gly Ile Gly Pro Asp Glu
            20                  25                  30

Ala Leu Gln Arg Leu Lys Glu Gly Asn Ala Arg Phe Val Ala Glu Thr
        35                  40                  45

Pro Thr Arg Gln Asn Leu Ser Ala Lys Arg Leu Ala Thr Ser Gln His
    50                  55                  60

Gly Gln Thr Pro Tyr Ala Thr Ile Leu Ser Cys Ala Asp Ser Arg Ala
65                  70                  75                  80

Pro Val Glu Leu Ile Phe Asp Glu Gly Val Gly Asp Leu Phe Val Ile
                85                  90                  95

Arg Val Ala Gly Asn Val Ala Ala Thr Asp Glu Val Gly Thr Ala Glu
            100                 105                 110

Tyr Gly Ala Asp His Leu Asn Val Pro Leu Leu Val Val Met Gly His
        115                 120                 125

Thr Gln Cys Gly Ala Val Thr Ala Val Val Gln Gly Ala Glu Val His
    130                 135                 140

Gly Ser Ile Pro Met Leu Val Ala Pro Ile Val Pro Ala Val Thr Ala
145                 150                 155                 160

Val Glu Lys Ser Asn Pro Lys His Asp Arg Ala Ala Leu Val Pro Lys
                165                 170                 175

Val Ile Glu Ala Asn Val Trp Gln Ala Ile Asp Asp Thr Met Arg Gln
            180                 185                 190
```

```
Ser Pro Ile Ile Arg Ala Arg Val Ala Ala Gly Lys Leu Lys Val Val
            195                 200                 205

Gly Ala Ile Tyr His Ile Asp Asp Gly Lys Val Glu Trp Leu Gly Glu
            210                 215                 220

His Pro Met Gln Ala Arg Leu Leu Asn Tyr Thr Ser Gly Pro Ala Lys
225                 230                 235                 240

Ala His

<210> SEQ ID NO 2
<211> LENGTH: 237
<212> TYPE: PRT
<213> ORGANISM: Desulfovibrio sp. U5L

<400> SEQUENCE: 2

Met Lys Arg Phe Leu Ala Ala Thr Ala Thr Met Ala Phe Leu Leu Ala
1               5                   10                  15

Met Cys Thr Ala Val Leu Ala Ser Ser Gly Gly Pro Glu Val Ser Ala
            20                  25                  30

Asp Glu Ala Leu Ser Arg Leu Lys Glu Gly Asn Thr Arg Phe Val Ser
            35                  40                  45

Gln Ala Asn Val Ala Pro His Gln Asp Ala Ala Arg Arg His Glu Thr
    50                  55                  60

Ala Thr Gly Gly Gln His Pro Phe Ala Thr Val Leu Ser Cys Ala Asp
65                  70                  75                  80

Ser Arg Ala Pro Val Glu Val Leu Phe Asp Gln Gly Val Gly Asp Leu
                85                  90                  95

Phe Val Val Arg Val Ala Gly Asn Val Ala Ala Thr Asp Glu Ile Gly
                100                 105                 110

Thr Ile Glu Tyr Gly Ala Glu His Leu Gly Val Pro Leu Val Val Val
            115                 120                 125

Leu Ala His Thr Lys Cys Gly Ala Val Thr Ala Val Val Lys Asn Glu
        130                 135                 140

Pro Val Thr Glu Asn Ile Gly Lys Leu Val Ala Pro Ile Val Pro Ala
145                 150                 155                 160

Val Lys Gly Val Lys Ala Arg Phe Ala Ala Ser Asp Val Asn Glu Ile
                165                 170                 175

Ile Ser Arg Ser Ile Glu Ala Asn Met Trp Gln Ala Val Ser Asp Ile
            180                 185                 190

Tyr Ala Lys Ser Pro Met Leu Lys Lys Met Ala Ala Asp Gly Lys Ile
        195                 200                 205

Lys Val Val Gly Ala Leu Tyr Asp Ile Asp Ser Gly Glu Val His Trp
    210                 215                 220

Phe Gly Glu His Pro Ser Glu Gly Asn Leu Leu Asp Asn
225                 230                 235

<210> SEQ ID NO 3
<211> LENGTH: 237
<212> TYPE: PRT
<213> ORGANISM: Desulfovibrio fructosovorans

<400> SEQUENCE: 3

Met Lys Arg Ala Phe Ala Ala Phe Ala Ala Val Phe Val Ala Ala
1               5                   10                  15

Thr Cys Ala Leu Ala Leu Ala Ser Ser Ala Gly Pro Gly Leu Thr Ser
            20                  25                  30
```

```
Asp Glu Ala Leu Ala Lys Leu Lys Glu Gly Asn Asp Arg Tyr Val Ala
         35                  40                  45

Lys Ala Ser Val Ala Pro Arg Arg Asp Ala Ala Arg Arg His Glu Thr
 50                  55                  60

Ala Thr Gly Gly Gln His Pro Phe Ala Thr Val Leu Ala Cys Ser Asp
 65                  70                  75                  80

Ser Arg Val Pro Val Glu Val Phe Asp Gln Gly Val Gly Asp Ile
             85                  90                  95

Phe Val Val Arg Val Ala Gly Asn Val Ala Ala Thr Asp Glu Ile Gly
            100                 105                 110

Thr Met Glu Tyr Gly Ala Glu His Leu Gly Val Pro Leu Ile Val Val
            115                 120                 125

Met Gly His Thr Lys Cys Gly Ala Val Ser Ala Val Val Lys Asn Glu
130                 135                 140

Pro Val Thr Glu Asn Ile Gly Lys Leu Val Ala Pro Ile Val Pro Ala
145                 150                 155                 160

Val Lys Ser Val Lys Ala Arg Phe Ala Thr Ala Asn Thr Asp Glu Leu
                165                 170                 175

Ile Ala Lys Ser Ile Glu Ala Asn Val Trp Gln Ala Ile Ser Asp Ile
            180                 185                 190

Tyr Ala Lys Ser Pro Leu Ile Lys Lys Met Ala Ala Gly Lys Val
            195                 200                 205

Lys Val Val Gly Ala Leu Tyr Asp Ile Asp Ser Gly Glu Val His Trp
            210                 215                 220

Leu Gly Glu His Pro Asn Asn Ala Ile Leu Leu Gly Lys
225                 230                 235

<210> SEQ ID NO 4
<211> LENGTH: 238
<212> TYPE: PRT
<213> ORGANISM: Desulfovibrio fructosovorans JJ

<400> SEQUENCE: 4

Met Met Lys Arg Ala Phe Ala Ala Phe Ala Ala Ala Val Phe Val Ala
 1               5                  10                  15

Ala Thr Cys Ala Leu Ala Leu Ala Ser Ser Ala Gly Pro Gly Leu Thr
                20                  25                  30

Ser Asp Glu Ala Leu Ala Lys Leu Lys Glu Gly Asn Asp Arg Tyr Val
         35                  40                  45

Ala Lys Ala Ser Val Ala Pro Arg Arg Asp Ala Ala Arg Arg His Glu
 50                  55                  60

Thr Ala Thr Gly Gly Gln His Pro Phe Ala Thr Val Leu Ala Cys Ser
 65                  70                  75                  80

Asp Ser Arg Val Pro Val Glu Val Phe Asp Gln Gly Val Gly Asp
                 85                  90                  95

Ile Phe Val Val Arg Val Ala Gly Asn Val Ala Ala Thr Asp Glu Ile
                100                 105                 110

Gly Thr Met Glu Tyr Gly Ala Glu His Leu Gly Val Pro Leu Ile Val
                115                 120                 125

Val Met Gly His Thr Lys Cys Gly Ala Val Ser Ala Val Val Lys Asn
            130                 135                 140

Glu Pro Val Thr Glu Asn Ile Gly Lys Leu Val Ala Pro Ile Val Pro
145                 150                 155                 160

Ala Val Lys Ser Val Lys Ala Arg Phe Ala Thr Ala Asn Thr Asp Glu
                165                 170                 175
```

Leu Ile Ala Lys Ser Ile Glu Ala Asn Val Trp Gln Ala Ile Ser Asp
                180                 185                 190

Ile Tyr Ala Lys Ser Pro Leu Ile Lys Lys Met Ala Ala Ala Gly Lys
            195                 200                 205

Val Lys Val Val Gly Ala Leu Tyr Asp Ile Asp Ser Gly Glu Val His
    210                 215                 220

Trp Leu Gly Glu His Pro Asn Asn Ala Ile Leu Leu Gly Lys
225                 230                 235

<210> SEQ ID NO 5
<211> LENGTH: 237
<212> TYPE: PRT
<213> ORGANISM: Desulfovibrio sp. TomC

<400> SEQUENCE: 5

Met Arg Arg Asn Met Thr Ala Met Thr Val Val Ile Trp Thr Leu Cys
1               5                   10                  15

Met Ala Thr Thr Ala Leu Ala Phe Ser Gly Gly Ala Gly Ile Thr Ala
            20                  25                  30

Asp Glu Ala Leu Ser Arg Leu Lys Glu Gly Asn Thr Arg Phe Val Ala
        35                  40                  45

Gly Ala Ala Val Thr Pro Arg Gln Asp Ala Ala Arg Arg His Glu Thr
    50                  55                  60

Thr Val Gly Gly Gln His Pro Phe Ala Thr Val Leu Ala Cys Ala Asp
65                  70                  75                  80

Ser Arg Val Pro Val Glu Ala Ile Val Asp Gln Gly Val Gly Asp Val
                85                  90                  95

Phe Val Val Arg Val Ala Gly Asn Val Ala Asn Thr Asp Glu Ile Gly
            100                 105                 110

Thr Ile Glu Tyr Gly Ala Glu His Leu Gly Val Pro Leu Val Val Val
        115                 120                 125

Leu Gly His Thr Lys Cys Gly Ala Val Thr Ala Val Val Lys Gly Glu
    130                 135                 140

His Val Thr Glu Asn Ile Gly Lys Leu Val Ala Pro Ile Val Pro Ala
145                 150                 155                 160

Val Ala Gly Val Lys Asn Arg Phe Ala Ser Ala Asp Leu Asp Glu Leu
                165                 170                 175

Ile Asn Arg Ser Ile Glu Ala Asn Val Trp Gln Ser Ile Ser Asp Met
            180                 185                 190

Tyr Ala Asn Ser Pro Leu Leu Lys Lys Met Ala Ala Asp Gly Lys Leu
        195                 200                 205

Lys Val Val Gly Ala Leu Tyr Asp Ile Asp Ser Gly Asp Ile His Trp
    210                 215                 220

Leu Gly Glu His Pro Ser Asn Ala Lys Leu Leu Gly Asn
225                 230                 235

<210> SEQ ID NO 6
<211> LENGTH: 230
<212> TYPE: PRT
<213> ORGANISM: Desulfovibrio sp. TomC

<400> SEQUENCE: 6

Met Thr Val Val Ile Trp Thr Leu Cys Met Ala Thr Thr Ala Leu Ala
1               5                   10                  15

Phe Ser Gly Gly Ala Gly Ile Thr Ala Asp Glu Ala Leu Ser Arg Leu
            20                  25                  30

```
Lys Glu Gly Asn Thr Arg Phe Val Ala Gly Ala Ala Val Thr Pro Arg
                35                  40                  45

Gln Asp Ala Ala Arg Arg His Glu Thr Thr Val Gly Gly Gln His Pro
 50                  55                  60

Phe Ala Thr Val Leu Ala Cys Ala Asp Ser Arg Val Pro Val Glu Ala
 65                  70                  75                  80

Ile Val Asp Gln Gly Val Gly Asp Val Phe Val Arg Val Ala Gly
                 85                  90                  95

Asn Val Ala Asn Thr Asp Glu Ile Gly Thr Ile Glu Tyr Gly Ala Glu
                100                 105                 110

His Leu Gly Val Pro Leu Val Val Val Leu Gly His Thr Lys Cys Gly
                115                 120                 125

Ala Val Thr Ala Val Val Lys Gly Glu His Val Thr Glu Asn Ile Gly
130                 135                 140

Lys Leu Val Ala Pro Ile Val Pro Ala Val Ala Gly Val Lys Asn Arg
145                 150                 155                 160

Phe Ala Ser Ala Asp Leu Asp Glu Leu Ile Asn Arg Ser Ile Glu Ala
                165                 170                 175

Asn Val Trp Gln Ser Ile Ser Asp Met Tyr Ala Asn Ser Pro Leu Leu
                180                 185                 190

Lys Lys Met Ala Ala Asp Gly Lys Leu Lys Val Val Gly Ala Leu Tyr
                195                 200                 205

Asp Ile Asp Ser Gly Asp Ile His Trp Leu Gly Glu His Pro Ser Asn
                210                 215                 220

Ala Lys Leu Leu Gly Asn
225                 230

<210> SEQ ID NO 7
<211> LENGTH: 237
<212> TYPE: PRT
<213> ORGANISM: Desulfovibrio magneticus

<400> SEQUENCE: 7

Met Lys Arg Phe Val Thr Ala Phe Ala Gly Ala Val Ile Thr Ile Ser
 1               5                  10                  15

Met Ala Gly Ala Ala Met Ala Phe Ser Gly Gly Ala Gly Ile Ser Ala
                 20                  25                  30

Asp Glu Ala Leu Ala Arg Leu Lys Glu Gly Asn Thr Arg Tyr Val Ala
                 35                  40                  45

Gly Ala Ala Val Thr Pro Arg Gln Asp Ala Ala Arg Arg His Glu Thr
 50                  55                  60

Ala Thr Gly Gly Gln His Pro Phe Val Ser Val Leu Ser Cys Ala Asp
 65                  70                  75                  80

Ser Arg Val Pro Val Glu Thr Val Phe Asp Gln Gly Ile Gly Asp Val
                 85                  90                  95

Phe Val Ile Arg Val Ala Gly Asn Val Ala Asn Thr Asp Glu Ile Gly
                100                 105                 110

Thr Ile Glu Tyr Gly Ala Glu His Leu Gly Thr Pro Leu Val Leu Val
                115                 120                 125

Met Ala His Thr Lys Cys Gly Ala Val Thr Ala Val Lys Gly Glu
130                 135                 140

His Val Thr Glu Asn Ile Gly Lys Leu Val Ala Pro Ile Val Pro Ala
145                 150                 155                 160

Val Ala Ser Val Lys Ser Arg Phe Ala Thr Asp Val Asn Glu Leu
                165                 170                 175
```

Ile Asn Arg Ser Ile Glu Ala Asn Met Trp Gln Ala Ile Ala Asp Met
            180                 185                 190

Tyr Ala Lys Ser Pro Leu Leu Lys Lys Met Ala Ala Asp Gly Lys Ile
        195                 200                 205

Lys Val Val Gly Ala Leu Tyr Asp Ile Asp Ser Gly Glu Val His Trp
    210                 215                 220

Phe Gly Glu His Pro Ser Asn Ala Asn Leu Leu Gly Lys
225                 230                 235

<210> SEQ ID NO 8
<211> LENGTH: 237
<212> TYPE: PRT
<213> ORGANISM: Desulfovibrio sp. FW1012B

<400> SEQUENCE: 8

Met Lys Arg Phe Leu Ala Ala Thr Ala Thr Met Ala Phe Leu Leu Ala
1               5                   10                  15

Met Cys Thr Ala Val Leu Ala Ser Ser Gly Gly Ser Glu Val Ser Ala
            20                  25                  30

Asp Glu Ala Leu Ser Arg Leu Lys Glu Gly Asn Thr Arg Phe Val Ser
        35                  40                  45

Gln Ala Asn Val Ala Pro His Gln Asp Ala Ala Arg Arg His Glu Thr
    50                  55                  60

Ala Thr Gly Gly Gln His Pro Phe Ala Thr Val Leu Ser Cys Ala Asp
65                  70                  75                  80

Ser Arg Ala Pro Val Glu Val Leu Phe Asp Gln Gly Val Gly Asp Leu
                85                  90                  95

Phe Val Val Arg Val Ala Gly Asn Val Ala Ala Thr Asp Glu Ile Gly
            100                 105                 110

Thr Ile Glu Tyr Gly Ala Glu His Leu Gly Val Pro Leu Val Val Val
        115                 120                 125

Leu Ala His Thr Lys Cys Gly Ala Val Thr Ala Val Val Lys Asn Glu
    130                 135                 140

Pro Val Thr Glu Asn Ile Gly Lys Leu Val Ala Pro Ile Val Pro Ala
145                 150                 155                 160

Val Lys Gly Ile Lys Ala Arg Phe Ala Ala Ser Asp Val Asn Glu Ile
                165                 170                 175

Ile Ser Arg Ser Ile Glu Ala Asn Met Trp Gln Ala Ile Ser Asp Ile
            180                 185                 190

Tyr Ala Lys Ser Pro Met Leu Lys Lys Met Ala Ala Asp Gly Lys Ile
        195                 200                 205

Lys Val Val Gly Ala Leu Tyr Asp Ile Asp Ser Gly Glu Val Arg Trp
    210                 215                 220

Phe Gly Glu His Pro Ser Glu Gly Ser Leu Leu Asp Asn
225                 230                 235

<210> SEQ ID NO 9
<211> LENGTH: 242
<212> TYPE: PRT
<213> ORGANISM: Desulfomonile tiedjei

<400> SEQUENCE: 9

Met Glu Ala Phe Met Lys Lys Ile Ala Val Leu Phe Ser Val Ile Cys
1               5                   10                  15

Met Leu Gly Ser Val Phe Ser Trp Ala Ala Asp Pro Ala Ala Thr Val
            20                  25                  30

```
Ser Pro Glu Glu Ala Val Lys Leu Leu Lys Glu Gly Asn Gly Arg Phe
        35                  40                  45

Ile Ala Gly Thr Ser Gln His Pro Asn Asn Asp Leu Gln Arg Arg Asn
 50                  55                  60

Thr Thr Ala Ala Gln Gly Gln His Pro Phe Val Thr Val Leu Ser Cys
 65                  70                  75                  80

Ser Asp Ser Arg Val Pro Val Glu Val Leu Phe Asp Arg Gly Val Gly
                 85                  90                  95

Asp Ile Phe Val Ile Arg Val Ala Gly Asn Val Ala Asn Gly Asp Glu
                100                 105                 110

Val Gly Ser Ile Glu Tyr Ala Val Asp His Leu Gly Thr Pro Leu Leu
            115                 120                 125

Val Ile Leu Gly His Thr Lys Cys Gly Ala Val Thr Ala Val Val Gln
130                 135                 140

Ser Ala Glu Leu Leu Gly Asn Ile Ile Pro Ile Gly Lys Ser Ile Phe
145                 150                 155                 160

Pro Ala Val Val Ala Ala Lys Lys Ser Asn Pro Lys Ala Ser Gly Asp
                165                 170                 175

Ala Leu Ile Asn Asp Ala Ile Lys Ala Asn Val Trp Gln Ala Ile Glu
                180                 185                 190

Asp Ile Tyr Arg Thr Ser Pro Ile Thr Ala Ala Arg Val Lys Ser Gly
            195                 200                 205

Lys Leu Lys Val Val Gly Ala Leu Tyr Asp Ile Glu Ser Gly Asn Val
210                 215                 220

Ser Trp Leu Gly Ser His Pro Lys Glu Gly Leu Leu Ser Asp Lys
225                 230                 235                 240

Gly His

<210> SEQ ID NO 10
<211> LENGTH: 238
<212> TYPE: PRT
<213> ORGANISM: Desulfomonile tiedjei DSM 6799

<400> SEQUENCE: 10

Met Lys Lys Ile Ala Val Leu Phe Ser Val Ile Cys Met Leu Gly Ser
 1               5                  10                  15

Val Phe Ser Trp Ala Ala Asp Pro Ala Thr Val Ser Pro Glu Glu
                20                  25                  30

Ala Val Lys Leu Leu Lys Glu Gly Asn Gly Arg Phe Ile Ala Gly Thr
            35                  40                  45

Ser Gln His Pro Asn Asn Asp Leu Gln Arg Arg Asn Thr Thr Ala Ala
 50                  55                  60

Gln Gly Gln His Pro Phe Val Thr Val Leu Ser Cys Ser Asp Ser Arg
 65                  70                  75                  80

Val Pro Val Glu Val Leu Phe Asp Arg Gly Val Gly Asp Ile Phe Val
                 85                  90                  95

Ile Arg Val Ala Gly Asn Val Ala Asn Gly Asp Glu Val Gly Ser Ile
                100                 105                 110

Glu Tyr Ala Val Asp His Leu Gly Thr Pro Leu Leu Val Ile Leu Gly
            115                 120                 125

His Thr Lys Cys Gly Ala Val Thr Ala Val Val Gln Ser Ala Glu Leu
130                 135                 140
```

-continued

```
Leu Gly Asn Ile Ile Pro Ile Gly Lys Ser Ile Phe Pro Ala Val Val
145                 150                 155                 160

Ala Ala Lys Lys Ser Asn Pro Lys Ala Ser Gly Asp Ala Leu Ile Asn
            165                 170                 175

Asp Ala Ile Lys Ala Asn Val Trp Gln Ala Ile Glu Asp Ile Tyr Arg
            180                 185                 190

Thr Ser Pro Ile Thr Ala Ala Arg Val Lys Ser Gly Lys Leu Lys Val
            195                 200                 205

Val Gly Ala Leu Tyr Asp Ile Glu Ser Gly Asn Val Ser Trp Leu Gly
            210                 215                 220

Ser His Pro Lys Glu Gly Gly Leu Leu Ser Asp Lys Gly His
225                 230                 235
```

<210> SEQ ID NO 11
<211> LENGTH: 237
<212> TYPE: PRT
<213> ORGANISM: Desulfovibrio alcoholivorans

<400> SEQUENCE: 11

```
Met Lys Arg Leu Phe Thr Ala Thr Thr Met Leu Ala Leu Leu Leu Ala
1               5                   10                  15

Cys Cys Ala Leu Ala Leu Ala Ser Ser Gly Gly Pro Gly Leu Thr Ala
            20                  25                  30

Asp Glu Ala Leu Ala Lys Leu Lys Glu Gly Asn Met Arg Tyr Val Ala
            35                  40                  45

Gln Ala Ser Val Ala Pro His Gln Asp Ala Ala Arg Arg His Glu Thr
    50                  55                  60

Ala Thr Asp Gly Gln His Pro Phe Ala Thr Ile Leu Ser Cys Ala Asp
65                  70                  75                  80

Ser Arg Val Pro Leu Glu Ile Ile Phe Asp Gln Gly Val Gly Asp Ile
            85                  90                  95

Phe Ala Val Arg Val Ala Gly Asn Val Ala Ala Val Asp Glu Ile Gly
            100                 105                 110

Thr Met Glu Tyr Gly Ala Glu His Leu Gly Val Pro Leu Ile Val Val
            115                 120                 125

Leu Gly His Thr Lys Cys Gly Ala Val Thr Ala Val Val Lys Asn Glu
130                 135                 140

Pro Val Thr Glu Asn Ile Gly Gln Leu Val Ala Pro Ile Val Pro Ala
145                 150                 155                 160

Val Lys Ser Val Lys Ser Arg Phe Ala Ser Ala Ser Leu Asp Glu Leu
            165                 170                 175

Ile Asn Lys Ser Ile Glu Ala Asn Val Trp Gln Ala Val Ser Asp Ile
            180                 185                 190

Tyr Ala Lys Ser Pro Leu Leu Lys Lys Met Ala Ala Gly Lys Val
            195                 200                 205

Lys Val Val Gly Ala Leu Tyr Asp Ile Asp Ser Gly Lys Val Gln Trp
    210                 215                 220

Phe Gly Glu His Pro Ser Asn Ala Ser Leu Leu Gly Lys
225                 230                 235
```

<210> SEQ ID NO 12
<211> LENGTH: 237
<212> TYPE: PRT
<213> ORGANISM: Desulfovibrio magneticus

<400> SEQUENCE: 12

```
Met Lys Arg Phe Val Ala Ala Phe Ala Gly Ala Val Ile Thr Phe Ser
1               5                   10                  15

Met Ala Gly Ala Ala Met Ala Phe Ser Gly Gly Ala Gly Ile Ser Ala
                20                  25                  30

Asp Glu Ala Leu Ala Arg Leu Lys Glu Gly Asn Thr Arg Tyr Val Ala
            35                  40                  45

Gly Ala Ala Val Thr Pro Arg Gln Asp Ala Ala Arg Arg His Glu Thr
        50                  55                  60

Ala Thr Gly Gly Gln His Pro Phe Val Ser Val Leu Ser Cys Ala Asp
65                  70                  75                  80

Ser Arg Val Pro Val Glu Thr Val Phe Asp Gln Gly Ile Gly Asp Val
                85                  90                  95

Phe Val Ile Arg Val Ala Gly Asn Val Ala Asn Thr Asp Glu Ile Gly
            100                 105                 110

Thr Ile Glu Tyr Gly Thr Glu His Leu Gly Thr Pro Leu Val Val Val
        115                 120                 125

Leu Ala His Thr Lys Cys Gly Ala Val Thr Ala Val Val Lys Gly Glu
    130                 135                 140

His Val Thr Glu Asn Ile Gly Lys Leu Val Ala Pro Ile Val Pro Ala
145                 150                 155                 160

Val Ala Ser Val Lys Ser Arg Phe Ala Ser Gly Asp Leu Asn Glu Leu
                165                 170                 175

Ile Asn Arg Ser Ile Glu Ala Asn Met Trp Gln Ala Ile Ala Asp Met
            180                 185                 190

Tyr Ala Lys Ser Pro Leu Leu Lys Lys Met Ala Ala Asp Gly Lys Ile
        195                 200                 205

Lys Val Val Gly Ala Leu Tyr Asp Ile Asp Ser Gly Asp Val His Trp
    210                 215                 220

Phe Gly Glu His Pro Ser Asn Ala Asn Leu Ile Gly Lys
225                 230                 235
```

<210> SEQ ID NO 13
<211> LENGTH: 220
<212> TYPE: PRT
<213> ORGANISM: Escherichia coli str. K-12 substr. [MG1655]

<400> SEQUENCE: 13

```
Met Lys Asp Ile Asp Thr Leu Ile Ser Asn Asn Ala Leu Trp Ser Lys
1               5                   10                  15

Met Leu Val Glu Glu Asp Pro Gly Phe Phe Glu Lys Leu Ala Gln Ala
                20                  25                  30

Gln Lys Pro Arg Phe Leu Trp Ile Gly Cys Ser Asp Ser Arg Val Pro
            35                  40                  45

Ala Glu Arg Leu Thr Gly Leu Glu Pro Gly Glu Leu Phe Val His Arg
        50                  55                  60

Asn Val Ala Asn Leu Val Ile His Thr Asp Leu Asn Cys Leu Ser Val
65                  70                  75                  80

Val Gln Tyr Ala Val Asp Val Leu Glu Val Glu His Ile Ile Ile Cys
                85                  90                  95

Gly His Tyr Gly Cys Gly Gly Val Gln Ala Ala Val Glu Asn Pro Glu
            100                 105                 110
```

-continued

Leu Gly Leu Ile Asn Asn Trp Leu His Ile Arg Asp Ile Trp Phe
            115                 120                 125

Lys His Ser Ser Leu Leu Gly Glu Met Pro Gln Glu Arg Arg Leu Asp
    130                 135                 140

Thr Leu Cys Glu Leu Asn Val Met Glu Gln Val Tyr Asn Leu Gly His
145                 150                 155                 160

Ser Thr Ile Met Gln Ser Ala Trp Lys Arg Gly Gln Lys Val Thr Ile
                165                 170                 175

His Gly Trp Ala Tyr Gly Ile His Asp Gly Leu Leu Arg Asp Leu Asp
            180                 185                 190

Val Thr Ala Thr Asn Arg Glu Thr Leu Glu Gln Arg Tyr Arg His Gly
                195                 200                 205

Ile Ser Asn Leu Lys Leu Lys His Ala Asn His Lys
            210                 215                 220

<210> SEQ ID NO 14
<211> LENGTH: 219
<212> TYPE: PRT
<213> ORGANISM: Escherichia coli

<400> SEQUENCE: 14

Met Lys Glu Ile Ile Asp Gly Phe Leu Lys Phe Gln Arg Glu Ala Phe
1               5                   10                  15

Pro Lys Arg Glu Ala Leu Phe Lys Gln Leu Ala Thr Gln Gln Ser Pro
            20                  25                  30

Arg Thr Leu Phe Ile Ser Cys Ser Asp Ser Arg Leu Val Pro Glu Leu
        35                  40                  45

Val Thr Gln Arg Glu Pro Gly Asp Leu Phe Val Ile Arg Asn Ala Gly
    50                  55                  60

Asn Ile Val Pro Ser Tyr Gly Pro Glu Pro Gly Gly Val Ser Ala Ser
65                  70                  75                  80

Val Glu Tyr Ala Val Ala Ala Leu Arg Val Ser Asp Ile Val Ile Cys
                85                  90                  95

Gly His Ser Asn Cys Gly Ala Met Thr Ala Ile Ala Ser Cys Gln Cys
            100                 105                 110

Met Asp His Met Pro Ala Val Ser His Trp Leu Arg Tyr Ala Asp Ser
        115                 120                 125

Ala Arg Val Val Asn Glu Ala Arg Pro His Ser Asp Leu Pro Ser Lys
    130                 135                 140

Ala Ala Ala Met Val Arg Glu Asn Val Ile Ala Gln Leu Ala Asn Leu
145                 150                 155                 160

Gln Thr His Pro Ser Val Arg Leu Ala Leu Glu Glu Gly Arg Ile Ala
                165                 170                 175

Leu His Gly Trp Val Tyr Asp Ile Glu Ser Gly Ser Ile Ala Ala Phe
            180                 185                 190

Asp Gly Ala Thr Arg Gln Phe Val Pro Leu Ala Ala Asn Pro Arg Val
        195                 200                 205

Cys Ala Ile Pro Leu Arg Gln Pro Thr Ala Ala
    210                 215

<210> SEQ ID NO 15
<211> LENGTH: 223
<212> TYPE: PRT
<213> ORGANISM: Neisseria gonorrhoeae

```
<400> SEQUENCE: 15

His Thr His Trp Gly Tyr Thr Gly His Asp Ser Pro Glu Ser Trp Gly
1               5                   10                  15

Asn Leu Ser Glu Glu Phe Arg Leu Cys Ser Thr Gly Lys Asn Gln Ser
                20                  25                  30

Pro Val Asn Ile Thr Glu Thr Val Ser Gly Lys Leu Pro Ala Ile Lys
            35                  40                  45

Val Asn Tyr Lys Pro Ser Met Val Asp Val Glu Asn Asn Gly His Thr
    50                  55                  60

Ile Gln Val Asn Tyr Pro Glu Gly Gly Asn Thr Leu Thr Val Asn Gly
65                  70                  75                  80

Arg Thr Tyr Thr Leu Lys Gln Phe His Phe His Val Pro Ser Glu Asn
                85                  90                  95

Gln Ile Lys Gly Arg Thr Phe Pro Met Glu Ala His Phe Val His Leu
            100                 105                 110

Asp Glu Asn Lys Gln Pro Leu Val Leu Ala Val Leu Tyr Glu Ala Gly
            115                 120                 125

Lys Thr Asn Gly Arg Leu Ser Ser Ile Trp Asn Val Met Pro Met Thr
    130                 135                 140

Ala Gly Lys Val Lys Leu Asn Gln Pro Phe Asp Ala Ser Thr Leu Leu
145                 150                 155                 160

Pro Lys Arg Leu Lys Tyr Tyr Arg Phe Ala Gly Ser Leu Thr Thr Pro
                165                 170                 175

Pro Cys Thr Glu Gly Val Ser Trp Leu Val Leu Lys Thr Tyr Asp His
            180                 185                 190

Ile Asp Gln Ala Gln Ala Glu Lys Phe Thr Arg Ala Val Gly Ser Glu
            195                 200                 205

Asn Asn Arg Pro Val Gln Pro Leu Asn Ala Arg Val Val Ile Glu
210                 215                 220
```

METHOD OF PRODUCING AND PROCESSING DIAMINES FROM AN ENGINEERED MICROORGANISM

PRIORITY CLAIM

This application claims priority from International Application No. PCT/US2015/067478 filed Dec. 22, 2015, which in turn claims the benefit of U.S. Provisional Patent Application Ser. No. 62/211,315 filed Aug. 28, 2015, U.S. Provisional Patent Application Ser. No. 62/193,693 filed Jul. 17, 2015, and U.S. Provisional patent Application Ser. No. 62/096,309 filed Dec. 23, 2014, the disclosure of each application incorporated herein by reference.

The present invention generally provides a process to produce, isolate, and purify a diamine, including hexamethylenediamine (HMD), cadaverine, putrescine, ethylenediamine and heptamethylenediamine. The invention more particularly relates to a method for culturing a microorganism producing the diamine, e.g. HMD, to a method of isolating the diamine from diamine-containing cultures or cultured media. Such diamine products are used to make diamine-containing polymers, including polyamides.

BACKGROUND

Hexamethylenediamine also referred to as 1,6-diaminohexane or 1,6-hexanediamine (abbreviated as HMD or HMDA) has the chemical formula $H_2N(CH_2)_6NH_2$. HMD is an important raw material in the chemical industry. HMD is used, for example, in the preparation of polyamides, polyureas or polyurethanes and copolymers of these materials. Cadaverine, also referred to as 1,5-diaminopentane, is used as a monomer for polyamine production. Putrescine, also referred to as 1,4-diaminobutane, is used as a monomer for polyamine production. Heptamethylenediamine, also referred to as 1,7-diaminoheptane, is used as a monomer for polyamine production. Ethylenediamine is used as a monomer for polyamine production as well as a precursor to other chemicals. Engineered microorganisms for fermentative production of these compounds and other diamines or their immediate precursors have been reported. Typically, processes for their fermentation and isolation require acids and bases that generate salt by-products.

SUMMARY OF THE INVENTION

An embodiment of the present invention utilizes carbon dioxide, added externally or produced metabolically, during a culture or fermentation process to produce a diamine species, at least one or more of diamine carbonate, diamine bicarbonate, and/or diamine bis-bicarbonate (collectively referred to herein as "Carbonates") and, optionally diamine carbamate or diamine biscarbamate (collectively referred to herein as "Carbamates"). When the Carbonates and/or Carbamates are formed, the diamine species are neutralized and the fermentation pH is controlled. A carbon source for growth of the microorganism and its production of the diamine is provided, as described below. Optionally the carbon dioxide (or carbonate, bicarbonate) is both the carbon source for the microorganism (via $CO_2$ fixation) and the compound for neutralizing the diamine. The diamine may be, for example, hexamethylenediamine (HMD), dimethylenediamine, trimethylenediamine, cadaverine, putrescine or heptamethylenediamine (diamines having two to seven carbon atoms (C2-C7), C3-C7, preferably C4-C7 or even C4 to C12 or C2-C12). Accordingly, the diamine species are, in the case of HMD for example, HMD carbonate, HMD bicarbonate, HMD bis-bicarbonate. The carbamate and biscarbamate are, in the case of HMD for example, HMD carbamate and HMD biscarbamate. The chemical formulas for the HMD species are shown below:

| | |
|---|---|
| Free base | $H_2N$—$(CH_2)_6$—$NH_2$ |
| Bicarbonate | $[H_2N$—$(CH_2)_6$—$NH_3]^+[HCO_3]^-$ |
| Carbonate | $[H_3N$—$(CH_2)_6$—$NH_3]^{2+}[CO_3]^{2-}$ |
| Bis-bicarbonate | $[H_3N$—$(CH_2)_6$-$NH_3]^{2+}[HCO_3]_2^{2-}$ |
| Carbamate | $H_2N$-$(CH_2)_6$—$NH$—$CO_2H$ |
| Biscarbamate | $HO_2C$—$HN$—$(CH_2)_6$—$NH$—$CO_2H$ |

In one embodiment, the present invention provides improved isolation of Carbonates and/or Carbamates from culture or fermentation medium, solutions or broths, including Carbonates and Carbamates of HMD, cadaverine, putrescine and heptamethylenediamine. In another embodiment, the Carbonates and Carbamates are treated to release carbon dioxide and diamine free base (e.g. HMD free base, cadaverine free base, putrescine free base, heptamethylenediamine free base), and then the diamine free base may be extracted with a suitable organic solvent. HMD-Carbonates and -Carbamates produced during simulated fermentation conditions, such as HMD carbonate, bicarbonate, bis-bicarbonate and carbamate and biscarbamate, were found to release $CO_2$ or other fragments and to generate HMD free base which was then solvent extracted. If necessary, the diamine free base enriched fraction is subject to further purification processes.

In another embodiment, the invention provides a process for diamine (DA) production comprising the steps of:
  a) culturing a genetically engineered microorganism in medium under suitable conditions and for a sufficient period of time to form one or more of DA carbonate, DA bicarbonate, DA bis-bicarbonate (Carbonates) and/or DA carbamate or DA biscarbamate (Carbamates) in the cultured medium wherein carbon dioxide, carbonate, bicarbonate or carbonic acid predominantly control pH of the medium as a cultured medium;
  b) converting the DA carbonate, DA bicarbonate, DA bis-bicarbonate, DA carbamate or DA biscarbamate into HMD free base and carbon dioxide; and;
  c) isolating the DA free base.

In another embodiment, the invention provides a process for diamine (DA) production comprising the steps of:
  a) culturing a genetically engineered microorganism in medium under suitable conditions and for a sufficient period of time to form one or more of DA carbonate, DA bicarbonate, DA bis-bicarbonate, DA carbamate or DA biscarbamate wherein dissolved inorganic carbon percent (DIC) is determined by the formula:

DIC/TDCA×100;

wherein the DIC % is greater than or equal to 40% and wherein TDCA is the Total Dissolved Counter Anions and is the sum of DIC and other anions;
  b) converting the DA carbonate, DA bicarbonate, DA bis-bicarbonate, DA carbamate or DA biscarbamate into DA free base and carbon dioxide; and
  c) isolating the DA free base.

In another embodiment, the invention provides a process for diamine (DA) production comprising the steps of:
  a) culturing a genetically engineered microorganism in medium comprising under suitable conditions and for a sufficient period of time to produced DA and form one or more of DA carbonate, DA bicarbonate, DA bis-bicarbonate (DA Carbonates) and/or DA carbamate or DA biscarbamate (DA Carbamates) in the medium, wherein at least 40% of Carbonates or Carbamates in the medium comprises one or more of DA carbonate, DA bicarbonate, DA bis-bicarbonate, DA carbamate or DA biscarbamate;

b) converting the Carbonates or Carbamates into DA free base and carbon dioxide; and c) isolating the DA free base.

In some embodiments, an enzyme carbonic anhydrase (CA) may be added to the fermentation broth to catalyze or increase the formation of diamine Carbonates and/or diamine Carbamates (e.g. HMDA Carbonates) by increasing the amount or rate of gaseous CO2 converted to soluble ion, thus providing a greater amount or availability of soluble ion available to the diamine or HMD. The CA can also be used when the diamine comprises C2 to C7 methylene segments, C2 to C12 methylene segments or C4 to C7 methylene segments, for example can be hexamethylenediamine (HMD), cadaverine, putrescine, ethylenediamine or heptamethylenediamine, to increase formation of the diamine Carbonates, including a carbonate, bicarbonate or bis-bicarbonate, and the diamine Carbamates, including a carbamate or biscarbamate, or any mixture thereof. In some embodiments, the carbonic anhydrase is used to form one of more HMD carbonates, HMD bicarbonate, HMD bis-bicarbonate, HMD carbamate or HMD biscarbamate. Carbonic anhydrase is a reversible enzyme and therefore in other embodiments is used to catalyze the conversion of DA Carbonates or DA Carbamates into DA free base and carbon dioxide.

In some embodiments, the carbonic anhydrase is present in sufficient amount to (a) enhance the formation of a DA Carbonates or DA Carbamates by converting carbon dioxide to a bicarbonate and/or carbonate ions, (b) enhance the release of carbon dioxide from a solution of DA Carbonates or DA Carbamates by converting a bicarbonate and/or carbonate ions to carbon dioxide, or (c) both (a) and (b). The CA may be added exogenously or may be produced by a genetically engineered microorganism. In some embodiments, the CA is part of a microorganism that expresses a DA synthesis pathway such as HMD synthesis pathway. In other embodiments, the CA is introduced as an engineered microorganism that has the ability to produce CA.

The CA or variant is expressed at sufficient amount to enhance either the desired conversion of CO2 to ion or ion to CO2 or both, which can be compared to the conversion or conversions in the absence of the CA or variant. An amount of CA or variant protein will depend on its carbonic anhydrase activity and desired enhancement. A typical amount can be in the range of at least 0.001 g per liter to at least 5 gram per liter, and from at least 0.01 g/liter, 0.05 g/l, 0.1 g/liter, 0.2 g/liter, 0.5 g/liter or 1 g/liter to at least 5 g/liter, for example 0.05 to 0.2 g/liter.

Alternative embodiments are processes wherein at least 50% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate), wherein at least 60% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate), wherein at least 70% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate), wherein at least 80% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate), wherein at least 90% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate), or wherein at least 99.9% of Carbonates and/or Carbamates in the medium comprises one or more of DA carbonate, DA bicarbonate, DA bis-bicarbonate, DA carbamate or DA biscarbamate (e.g. HMDA carbonate, HMDA bicarbonate, HMDA bis-bicarbonate, HMDA carbamate or HMDA biscarbamate). In some embodiments, the Carbonates are the predominate diamine species and can include at least 50% of the DA species and up to at least 90%.

In some embodiments, the genetically engineered microorganism further forms one or more of carbon dioxide, carbonate, bicarbonate or carbonic acid. The genetically engineered microorganism formed carbon dioxide, carbonate, bicarbonate or carbonic acid may comprise stoichiometric carbon dioxide from Carbonate and/or Carbamate formation, or the genetically engineered microorganism formed carbon dioxide, carbonate, bicarbonate or carbonic acid may comprise respiration carbon dioxide or by-product carbon dioxide. In certain embodiments, the respiration carbon dioxide is formed from at least one pathway selected from, for example, via the completion of the TCA cycle, via the glyoxylate shunt, via the pentose phosphate pathway (e.g. gnd (6-phosphogluconate dehydrogenase that converts 6-phosphogluconate to ribuloase-5-phosphate and $CO_2$)), or via the Entner Duodoroff pathway. In other embodiments, the by-product carbon dioxide is associated with the formation of by-products that include acetate, ethanol, succinate, 3-oxoadipate, and 3-hydroxyadipate.

In some embodiments, a genetically engineered microorganism that comprises a diamine synthesis pathway, and optionally produces CO2, as described herein, can further comprise a CA enzyme, particularly where the microorgansims is engineered to have a nucleic acid sequence capable of expressing CA. Accordingly, engineered microorganisms comprising a synthetic pathway to produce a diamine that comprises C2 to C7 methylene segments, C2 to C12 methylene segments or C4 to C7 methylene segments, for example where the diamine is hexamethylenediamine (HMD), cadaverine, putrescine, ethylenediamine or heptamethylenediamine, can further comprise a CA enzyme, particularly where the microorgansims is engineered to have a nucleic acid sequence capable of expressing CA. In some embodiments, a genetically engineered microorganism comprises a hexamethylenediamine synthesis pathway and sequences capable of expressing CA. In other embodiments, the genetically engineered microorganism comprises sequences capable of expressing CA. The CA can be native or genetically engineered, such as to increase activity or stability including thermal stability and alkaline pH stability. Preferably the alkaline pH is about pH 8-13, pH 8.5 to 13, pH 9-13, pH 10-13, pH 8-12, pH 8.5-12, pH 9-12, pH 8-11, pH 8.5-11, pH 9-11, pH 10-11 and pH 10-12.

In some embodiments, the genetically engineered microorganism forms carbon dioxide and hexamethylenediamine in a ratio of about 0.05 to 1 to about 7 to 1. In other embodiments, the genetically engineered microorganism forms carbon dioxide and hexamethylenediamine in a ratio of about 0.05 to 1 to about 5 to 1, in a ratio of about 0.05 to 1 to about 3.5 to 1, in a ratio of about 0.05 to 1 to about 3 to 1, in a ratio of about 0.05 to 1 to about 2 to 1, in a ratio of about 0.05 to 1 to about 1.5 to 1, in a ratio of about 0.05 to 1 to about 1 to 1, or in a ratio of about 0.2 to 1 to about 3 to 1.

In some embodiments, the genetically engineered microorganism comprises a HMD synthesis pathway with at least one exogenous nucleic acid encoding at least one enzyme of the HMD synthesis pathway expressed in a sufficient amount to produce at least one HMD Carbonates and/or Carbamates compound. In still other embodiments, the genetically engineered microorganism comprises a HMD synthesis pathway with at least two, three, four, five, six, seven, eight, nine, ten, or eleven exogenous nucleic acids encoding at least two, three, four, five, six, seven, eight, nine, ten or eleven enzymes of the HMD synthesis pathway expressed in a sufficient amount to produce at least one HMD Carbonates and/or Carbamates compound.

In some embodiments, the HMD synthesis pathway comprises an intermediate compound selected from the group consisting of 3-oxoadipyl-CoA, adipate semialdehyde, 6-aminocaproate (6-ACA), 6-ACA semialdehyde, 2-aminopimelate, 3,6-dihydroxyhexanoyl-CoA and homolysine.

In some embodiments, the HMD synthesis pathway comprises an enzyme selected from the group consisting of 3-oxoadipyl-CoA thiolase, 6-ACA transaminase or dehydrogenase, 6-aminocaproyl-CoA reductase, 6-ACA reductase, adipyl-CoA reductase, adipate reductase, 6-hydroxy 3-oxohexanoyl-CoA dehydrogenase, 2-aminopimelate decarboxylase, and homolysine decarboxylase.

In some embodiments, the HMD synthesis pathway comprises an enzyme and substrate-product pair selected from the group consisting of 3-oxoadipyl-CoA thiolase that acts on succinyl-CoA and acetyl-CoA to make 3-oxoadipyl-CoA, 6-ACA transaminase that acts on adipyl-CoA to form 6-ACA, 6-aminocaproyl-CoA reductase that acts on 6-aminocaproayl-CoA to form 6-ACA semialdehyde, 6-ACA reductase that acts on 6-ACA and converts it directly to 6-ACA semialdehyde, adipyl-CoA reductase that acts on adipyl-CoA to form adipate semialdehyde, adipate reductase that acts on adipate and converts it directly to adipate semialdehyde, 6-hydroxy 3-oxohexanoyl-CoA dehydrogenase that reduces 6-hydroxy 3-oxohexanoyl-CoA to form 3,6-dihydroxy hexanoyl-CoA, 2-aminopimelate decarboxylase that decarboxylates 2-aminopimelate to form 6-ACA, and homolysine decarboxylase that decarboxylates homolysine to form HMD.

In some embodiments, the HMD synthesis pathway is selected from the group of pathways (a) to (m):

(a) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 6-ACA transferase or synthetase and 6-ACA-CoA reductase, or 6-ACA reductase, HMDA transaminase or dehydrogenase;

(b) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 6-ACA reductase, HMDA transaminase or dehydrogenase;

(c) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA transferase, hydrolase or transferase, adipate reductase, 6-ACA transaminase or dehydrogenase, 6-ACA transferase or synthetase, 6-ACA-CoA reductase, HMDA transaminase or dehydrogenase;

(d) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA transferase, hydrolase or transferase, adipate reductase, 6-ACA transaminase or dehydrogenase, 6-ACA reductase, HMDA transaminase or dehydrogenase;

(e) 3-oxoadipyl-CoA thiolase, 3-oxoadipate dehydrogenase, 3-hydroxyadipate dehydratase, 5-carboxy-2-pentenoate reductase, adipate reductase, 6-ACA transaminase or dehydrogenase, 6-ACA transferase or synthetase, 6-ACA-CoA reductase, HMDA transaminase or dehydrogenase;

(f) 3-oxoadipyl-CoA thiolase, 3-oxoadipate dehydrogenase, 3-hydroxyadipate dehydratase, 5-carboxy-2-pentenoate reductase, adipate reductase, 6-ACA transaminase or dehydrogenase, 6-ACA reductase, HMDA transaminase or dehydrogenase;

(g) 3-oxoadipyl-CoA thiolase, 3-oxoadipate dehydrogenase, 3-hydroxyadipate dehydratase, 5-carboxy-2-pentenoate reductase, adipyl-CoA transferase, hydrolase or transferase, adipyl-CoA reductase, 6-ACA transaminase or dehydrogenase, 6-ACA transferase or synthetase, 6-ACA-CoA reductase, HMDA transaminase or dehydrogenase;

(h) 3-oxoadipyl-CoA thiolase, 3-oxoadipate dehydrogenase, 3-hydroxyadipate dehydratase, 5-carboxy-2-pentenoate reductase, adipyl-CoA transferase, hydrolase or transferase, adipyl-CoA reductase, 6-ACA transaminase or dehydrogenase, 6-ACA reductase, HMDA transaminase or dehydrogenase;

(i) an 4-hydroxy-2-oxoheptane-I,7-dioate (HODH aldolase); an 2-oxohept-4-ene-1,7-dioate (OHED) hydratase; an OHED formate-lyase and a pyruvate formate-lyase activating enzyme or OHED dehydrogenase; a 2,3-dehydroadipyl-CoA reductase; an adipyl-CoA dehydrogenase; or an adipate semialdehyde aminotransferase or an adipate semialdehyde oxidoreductase (aminating);

(j) a β-ketothiolase or an acetyl-CoA carboxylase and an acetoacetyl-CoA synthase, a 3-hydroxyacyl-CoA dehydrogenase or a 3-oxoacyl-CoA reductase, an enoyl-CoA hydratase, and a trans-2-enoyl-CoA reductase for producing hexanoyl-CoA, one or more of a thioesterase, an aldehyde dehydrogenase, or a butanal dehydrogenase, said host producing hexanal or hexanoates; one or more of a monooxygenase, an alcohol dehydrogenase, an aldehyde dehydrogenase, a 6-hydroxyhexanoate dehydrogenase, a 5-hydroxypentanoate dehydrogenase, a 4-hydroxybutyrate dehydrogenase, a 6-oxohexanoate dehydrogenase, or a 7-oxoheptanoate dehydrogenase, said host producing adipic acid or adipate semialdehyde; one or more of a monooxygenase, a transaminase, a 6-hydroxyhexanoate dehydrogenase, a 5-hydroxypentanoate dehydrogenase, a 4-hydroxybutyrate dehydrogenase, and an alcohol dehydrogenase, said host producing 6-aminohexanoate; one or more of a carboxylate reductase, a w-transaminase, a deacetylase, a N-acetyl transferase, or an alcohol dehydrogenase, said host producing hexamethylenediamine;

(k) acetyltransferase or thiolase to form 6-hydroxy-3-oxo-hexanoyl-CoA, 6-hydroxy-3-oxo-hexanoyl-CoA dehydrogenase, 3,4-dihydroxyhexanoyl-CoA dehydratase, 6-hydroxy-2-hexenoyl-CoA reductase, 6-hydroxyhexanoyl-CoA hydrolase to form 6-ACA, 6-hydroxycaproate dehydrogenase and transaminase to form HMDA;

(l) homocitrate synthase, a homoaconitase and a homoisocitrate dehydrogenase to form 2-ketopimelate, 2-keto decarboxylase catalyzing the conversion of α-ketopimelate to adipate semialdehyde, 2-aminotransferase catalyzes the conversion of α-ketopimelate to 2-aminopimelate, 2-aminopimelate decarboxylase to decarboxylate 2-aminopimelate and form 6-ACA, aldehyde dehydrogenase catalyzes the conversion of 6-ACA to 6-aminohexanal and the aminotransferase catalyzes the conversion of 6-aminohexanal to 6-hexamethylenediamine; and (m) glutamyl-CoA transferase and/or ligase, beta-ketothiolase, 3-oxo-6-aminopimeloyl-CoA oxidoreductase, 3-hydroxy-6-aminopimeloyl-CoA dehydratase, 6-amino-7-carboxyhept-2-enoyl-CoA reductase, 6-aminopimeloyl-CoA reductase (aldehyde forming), 2-amino-7-oxoheptanoate aminotransferase and/or aminating oxidoreductase, homolysine decarboxylase, 6-aminopimeloyl-CoA hydrolase, transferase and/or ligase, 2-aminopimelate decarboxylase.

In any of the embodiments in the alternative pathways set out above, suitable enzymes may be selected from the group consisting of 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 3-oxoadipyl-CoA: acyl CoA transferase, 3-oxoadipate dehydrogenase, 3-hydroxyadipate dehydratase, 5-carboxy-2-pentenoate reductase, adipyl-CoA transferase, lygase or hydrolase, 6-ACA transferase or synthetase, 6-ACA-CoA reductase, HMDA transaminase or dehydrogenase, adipate reductase, 6-ACA transaminase or dehydrogenase, or 6-ACA reductase.

In some embodiments, the genetically engineered microorganism include the genus *Escherichia*, *Klebsiella*; the order Aeromoriadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*, the genus *Alkaliphilus, Methylobacterium, Methyloversatilis, Methylococcus, Methylocystis* and *Hyphomicrobium* the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*.

In other embodiments the genetically engineered microorganism include *Escherichia coli, Klebsiella oxytoca, Anaerobiospirillum succiniciproducens, Actinobacillus succinogenes, Mannheimia succiniciproducens, Rhizobium etli, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida, Bacillis pseudofirmus, Bacillus halodurans, Bacillus alcalophilus, Clostridium paradoxum, Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and *Issatchenkia orientalis*.

Some emodiments of alkaliphiles are: *Bacillis pseudofirmus, Bacillus halodurans, Bacillus alcalophilus, Clostridium paradoxum, Arthrospira platensis, Bacillus clausii, Oceanobacillus iheyensis, Alkaliphilus metaffiredigens, Alkaliphilus oremlandii, Bacillus selentireducens, Desulfovibrio alkaliphiles, Dethiobacter alkaliphiles, Thioalkalivibrio sp., Natranaerobius thermophilus, Alkalilimnicola ehrlichii,* and *Desulfonatronospira thiodismutans*.

In some embodiments, the culture medium fermentation may be substantially free of a buffer, may be substantially free of inorganic or organic acid, substantially free of externally added inorganic or organic acid or substantially free of DIC.

In some embodiments, the medium and/or cultured medium pH is controlled by carbon dioxide amount added to the culture medium, or alternatively, the cultured medium pH is controlled by the amount of carbon dioxide formed by the genetically engineered microorganism. In certain embodiments, the medium has a pH and/or the cultured medium is controlled to a pH of less than 11, less than 10, less than 9, or less than 8. In other embodiments, the medium has a pH and/or the cultured medium is controlled to a pH of at least 2, at least 3, at least 4, at least 5, at least 6, or at least 7. In still other embodiments, the medium has a pH and/or the cultured medium is controlled to a pH of about 6 to 9.5, a pH of about 6 to 9, a pH of about 6 to 8, a pH of about 7-9 or a pH of about 8-9.

In still other embodiments, the medium comprises a sugar carbon source for the genetically engineered microorganism selected from the group consisting of sucrose, glucose, galactose, fructose, starch, mannose, isomaltose, xylose, pannose, maltose, arabinose, cellobiose and 3-, 4-, or 5-oligomers thereof, or the medium comprises an alcohol carbon source for the genetically engineered microorganism selected from the group consisting of methanol, ethanol, glycerol, formate and fatty acids, or the medium comprises a carbon source obtained from gas for the genetically engineered microorganism selected from the group consisting of synthesis gas, waste gas, methane, CO, $CO_2$, and any mixture of CO or $CO_2$ with $H_2$.

In some embodiments, the Carbonates and/or Carbamates are converted to the free base, e.g. hexamethylenediamine free base, by generating carbon dioxide. In certain embodiments, the Carbonates and/or Carbamates are converted to the free base by heat, the Carbonates and/or Carbamates are converted to the free base by vacuum, the Carbonates and/or Carbamates are converted to the free base by pressure, the Carbonates and/or Carbamates are converted to the free base by ion exchange, the Carbonates and/or Carbamates are converted to the free base by steam stripping, or the Carbonates and/or Carbamates are converted to the free base by electrodialysis using a bipolar membrane. In still other embodiments, the conversion to the free base is accelerated by or enhanced by the addition of a carbonic anhydrase enzyme. The carbonic anhydrase may also be used to accelerate or enhance the release to free base when heat or other steps are used to convert the DA carbonates and/or DA Carbamates to free DA and carbon dioxide.

In some embodiments the diamine free base (e.g. HMD) is isolated from the medium using an extraction solvent and the extracted diamine is separated from the extraction solvent by distillation. In certain embodiments the extraction solvent is selected from the group consisting of alcohols, amines, ethers and ketones. Suitable extraction solvents comprise C4-C8 monohydric alcohols such as butanol, hexanal, 1-hexanol, isopentanol, or cyclohexanol, or alternatively toluene or ethyl ether or mixtures thereof. Alkanes are suitable solvents as demonstrated in the Examples, particularly for HMD free base. Alkanes, specifically hexane, were screened and subsequently tested due to extremely low water solubility. Hexane extracted little if any water and provided reasonable recovery of the available free base. Alkanes are therefore suitable solvents for use in recovery of diamine free base. Suitable alkanes include C5-C12, linear or branched. In one embodiment, both the diamine to be extracted and the alkane selected as solvent will have the same number of carbon atoms. Heptane is another suitable alkane, especially for HMD, which is further supported by the in silico modeling study below. Isomers of hexane and heptane are suitable. Hexane isomers are 2-methylpentane, 3-methylpentane, 2,2-dimethylbutane, and 2,3-dimethylbutane. Heptane isomers are 2-methylhexane, 3-methylhexane, 2,2-dimethylpentane, 2,3-dimethylpentane, 2,4-dimethylpentane, 3,3-dimethylpentane, 3-ethylpentane and 2,2,3-trimethylbutane.

In some embodiments, the genetically engineered microorganism is *Escherichia coli, Corynebacterium glutamicum, Bacillus subtilis, Pseudomonas putida, Bacillis pseudofirmus, Bacillus halodurans, Bacillus alcalophilus, Clostridium paradoxum, Saccharomyces cerevisiae*. In other embodiments, the genetically engineered microorganism is modified for improved alkali tolerance.

In some embodiments, the DA, e.g. HMD, produced by the present invention comprises one or more of DA carbonate, DA bicarbonate, DA bis-bicarbonate or DA carbamate impurities.

In some embodiments, a polymer, e.g. a polyamide for example PA66, comprising the diamine, e.g. HMD, produced by the present process comprises one or more of the DA carbonate, DA bicarbonate, DA bis-bicarbonate, DA carbamate or DA biscarbamate (e.g. HMD carbonate, HMD bicarbonate, HMD bis-bicarbonate, HMD carbamate or HMD biscarbamate) as impurities.

Another embodiment of the invention may be a genetically engineered microorganism comprising a diamine synthesis pathway, e.g. a hexamethylenediamine synthesis pathway, with at least one exogenous nucleic acid encoding at least one enzyme of the diamine synthesis pathway, e.g. HMD synthesis pathway, and at least one genetic modification that enhances or increases $CO_2$ availability to increase production of a diamine Carbonate and/or Carbamate, e.g. HMD Carbonate and/or Carbamate, compared to a genetically engineered microorganism absent that genetic modification. In one embodiment, a genetically engineered microorganism comprising the diamine, e.g. hexamethylenediamine, synthesis pathway with at least one exogenous nucleic acid encoding at least one enzyme of the diamine, e.g. HMD, synthesis pathway, and at least one carbonic anhydrase enzyme is used to increase production of the diamine, e.g. HMD, Carbonate and/or Carbamate compared to a genetically engineered microorganism absent the CA enzyme. The CA-expressing microorganism can further comprise the at least one genetic modification that increases $CO_2$ availability.

In any of the embodiments of the present invention, released carbon dioxide, the extraction solvent and/or water may be recycled. In other embodiments, the CA may be recycled.

In addition to the present process steps of culturing, converting and isolating described in the above embodiments, the present inventions also includes alternative and optional process steps. In some embodiments, the cultured medium or solution may be treated to remove solids and water during the process, either before isolating the DA free base and/or before converting the Carbonates and/or Carbamates to the DA free base. In other embodiments, the cultured medium may be treated to remove water, preferably before isolating the DA free based. In still other embodiments, the DA free base may be directly distilled from the cultured medium or solution. In still other embodiments, the DA free base be further treated and or purified after the extraction solvent is removed by distillation. In still other embodiments, the water removal or reduction and the conversion of the Carbonates and/or Carbamates to the DA free base, e.g. HMD free base) occur simultaneously and/or sequentially in the same unit operation. For example, the stripper unit (e.g. inert gas or steam) if present can be used to remove or reduce both water and CO2 to generate the free base. For a further example, the water evaporator unit if present can be used to remove or reduce both water and CO2 to generate the free base. The CA may be present during fermentation for formation of the diamine Carbonate and/or Carbamate or may be present during the step or steps for release of CO2 or may be present at either or both steps. In some embodiments, he CA may be recycled.

These alternative and/or optional process steps are described in detail below.

1: Product fermentation

2: Microbiol inactivation/Heat kill. May result in partial release of carbon dioxide and free base due to elevated temperature 3: Solids removal 4: Carbonate/Carbamate conversion to carbon dioxide and free base. Carbon dioxide is optionally recycled to fermentor.

5: Water removal. Water is optionally recycled to the product fermentation step. Carbon dioxide can also be recycled if water removal step involves conditions that can release carbon dioxide and free base.

6: Solvent extraction. Aqueous raffinate is optionally recycled to the Carbonate/Carbamate conversion step.

7: Purification: Involves distillation which recycles organic solvent back to box 6; could involve more distillation columns to purify HMD and other steps to remove color forming compounds, etc.

8: Purified HMD

9: Optional Sterilization where no carbon dioxide is released

10: Optional water removal. Water is optionally recycled to the product fermentation step. Carbon dioxide can also be recycled if water removal step involves conditions that can release carbon dioxide and free base.

11: Optional direct purification from aqueous phase with or without release of carbon dioxide. This could involve distillation, ion exchange, electrodialysis, etc. Possible to recycle water and carbon dioxide if it is produced in these steps 12: Alkalization (NaOH or CaOH) or other steps to remove Carbonates from HMD (Ion exchange, electrodialysis, etc.). If CaOH is used a precipitate will form.

Figure 5:
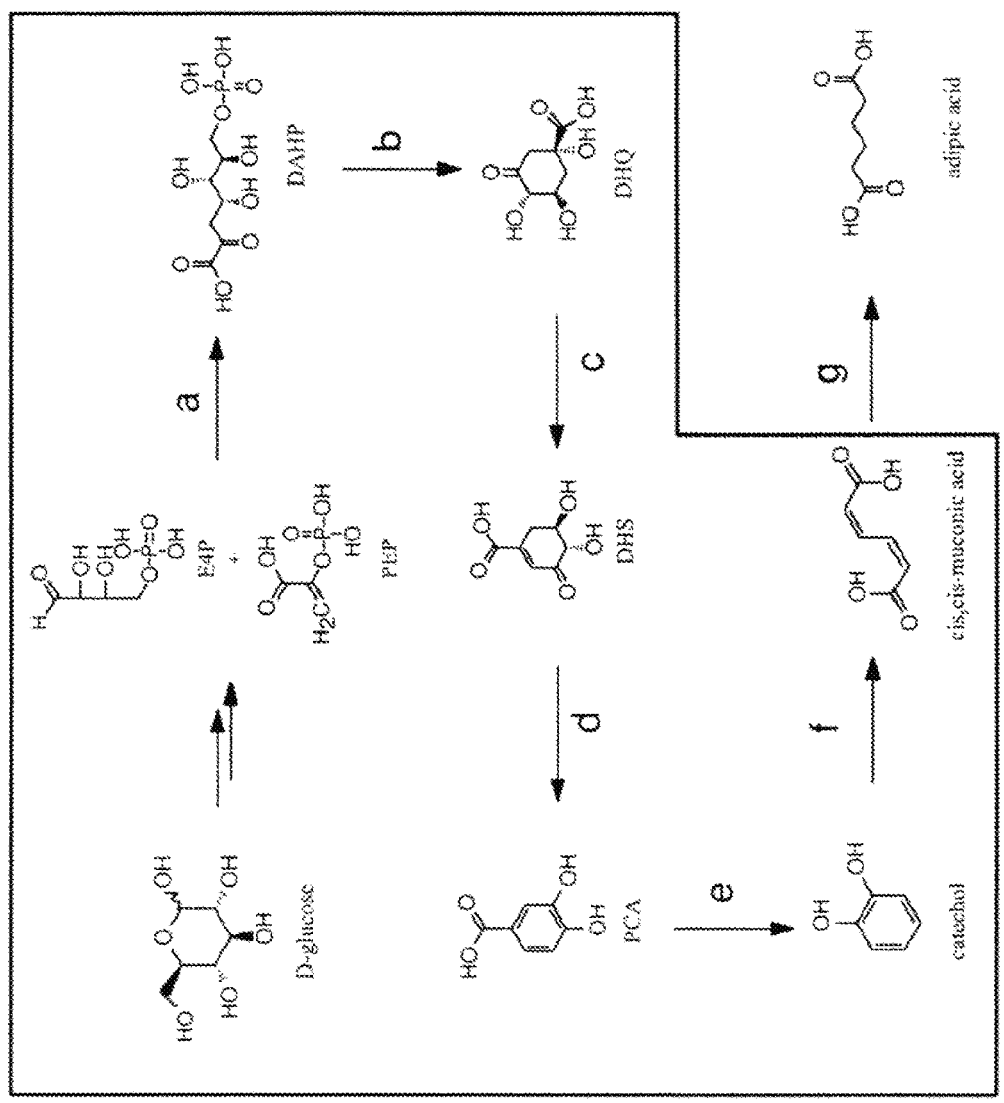

FIG. 5 shows an exemplary pathway for synthesis of adipic acid from glucose via cis,cis-muconic acid. Biosynthetic intermediates (abbreviations): D-erythrose 4-phosphate (E4P), phosphoenolpyruvic acid (PEP), 3-deoxy-D-arabinoheptulosonic acid 7-phosphate (DAHP), 3-dehydroquinic acid (DHQ), 3-dehydroshikimic acid (DHS), protocatechuic acid (PCA). Enzymes (encoding genes) or reaction conditions: (a) DAHP synthase (aroFFBR), (b) 3-dehydroquinate synthase (aroB), (c) 3-dehydroquinate dehydratase (aroD), (d) DHS dehydratase (aroZ), (e) protocatechuate decarboxylase (aroY), (f) catechol 1,2-dioxygenase (catA), (g) 10% Pt/C, H.sub.2, 3400 kPa, 25.degree. C. Figure taken from Niu et al., Biotechnol. Prog. 18:201-211 (2002).

Figure 6:
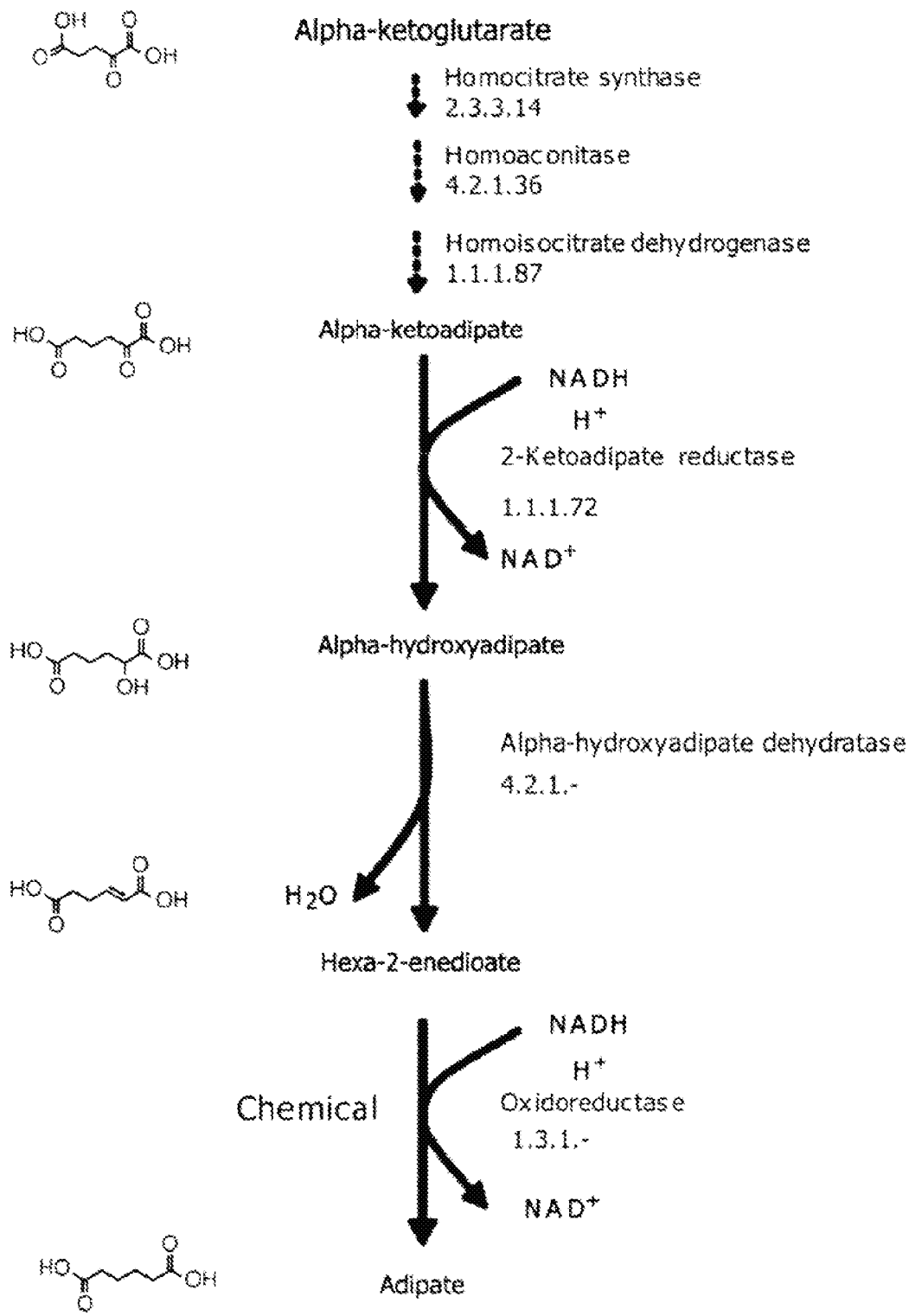

FIG. 6 shows an exemplary pathway for adipate synthesis via alpha-ketoadipate using alpha-ketoglutarate as a starting point.

Figure 7:
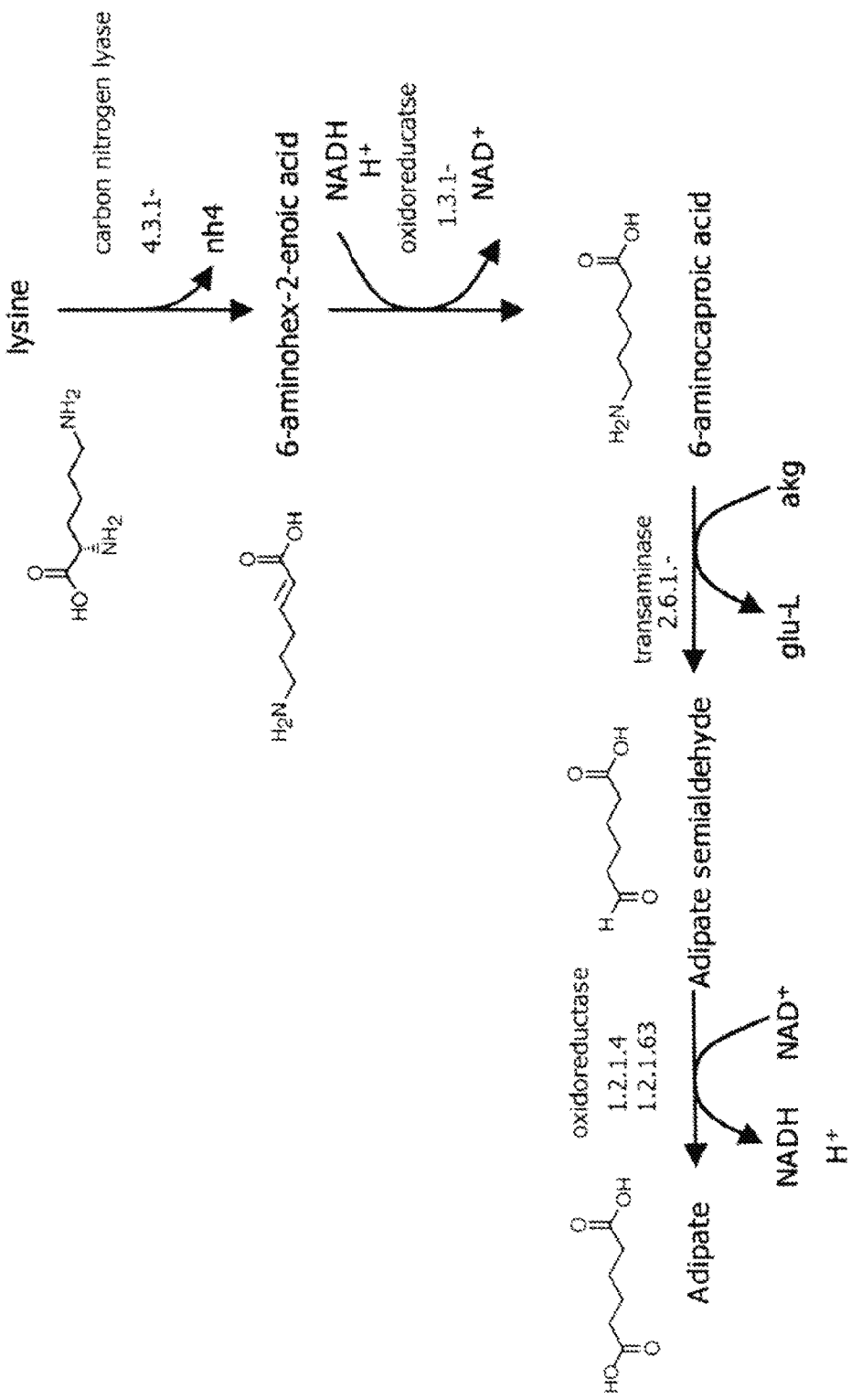

FIG. 7 shows an exemplary pathway for synthesis of adipate using lysine as a starting point.

Figure 8:
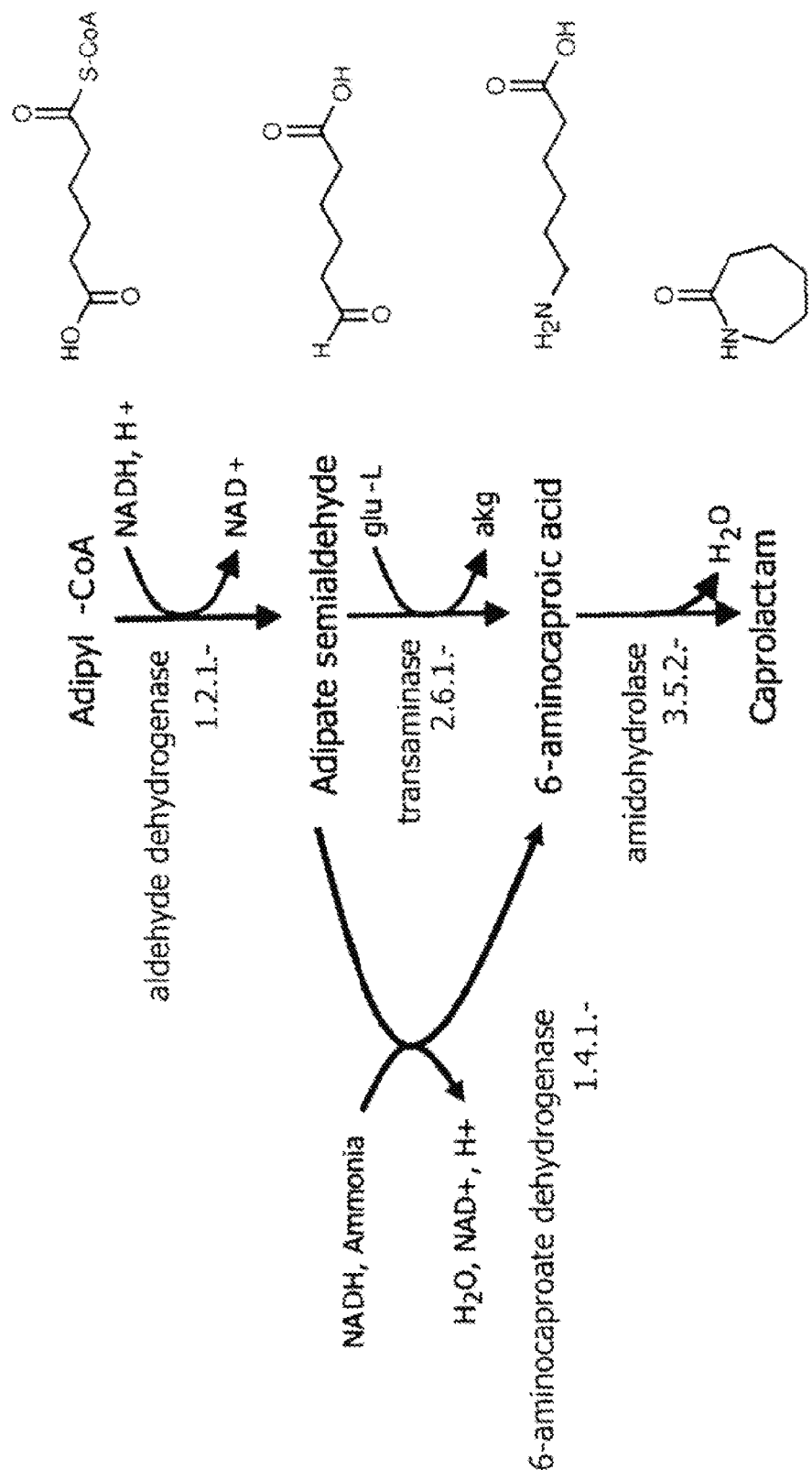

FIG. 8 shows an exemplary caprolactam synthesis pathway using adipyl-CoA as a starting point.

Figure 9:
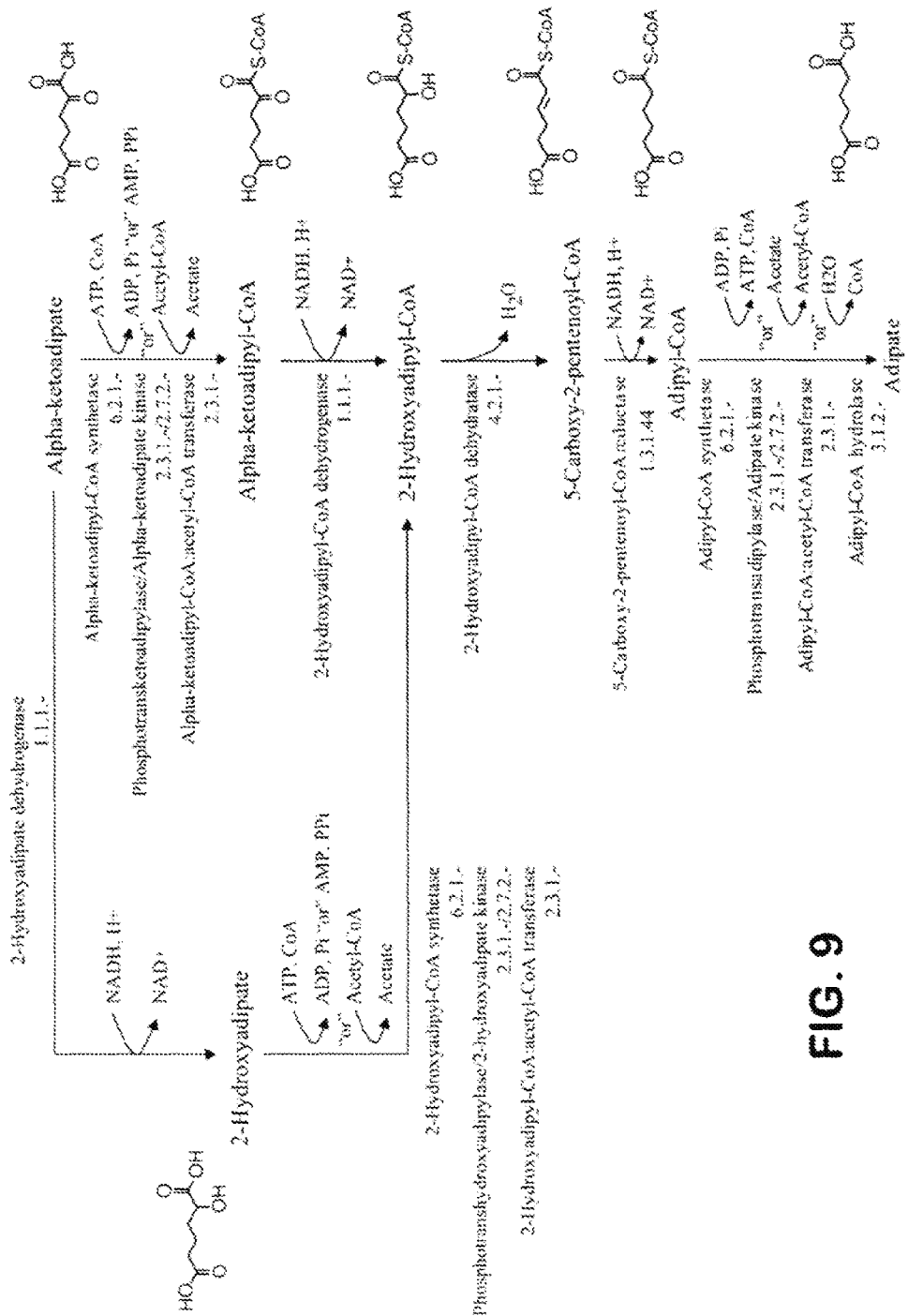

FIG. 9 shows exemplary adipate synthesis pathways using alpha-ketoadipate as a starting point.

Figure 10:
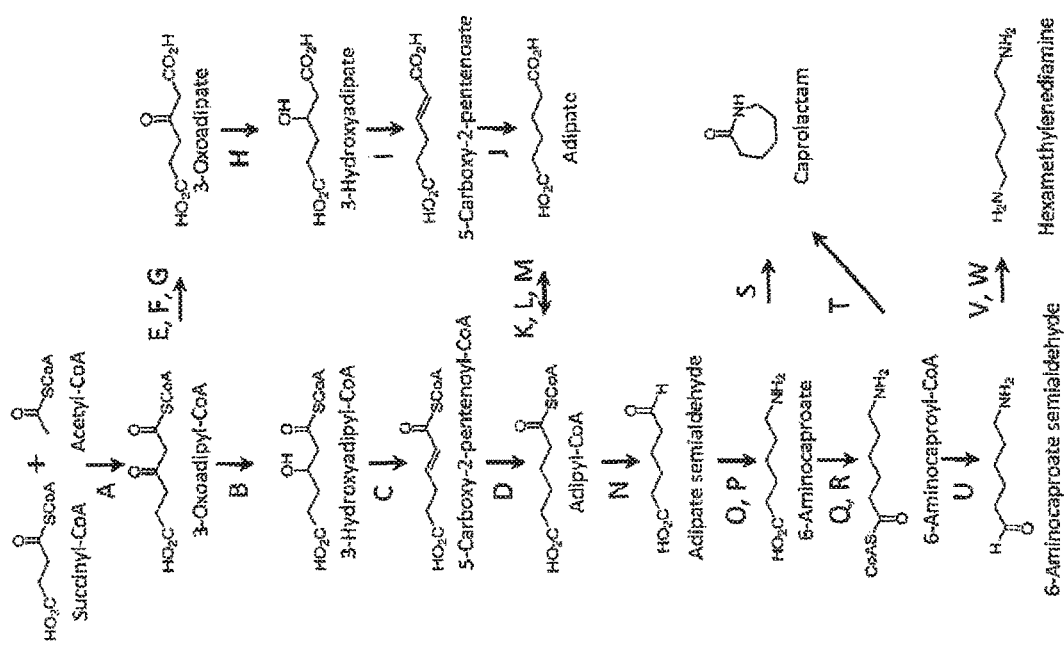

FIG. 10 shows exemplary pathways from succinyl-CoA and acetyl-CoA to hexamethylenediamine (HMDA) and caprolactam. Pathways for the production of adipate, 6-aminocaproate, caprolactam, and hexamethylenediamine from succinyl-CoA and acetyl-CoA are depicted. Abbreviations: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) 3-oxoadipyl-CoA/acyl-CoA transferase, F) 3-oxoadipyl-CoA synthase, G) 3-oxoadipyl-CoA hydrolase, H) 3-oxoadipate reductase, I) 3-hydroxyadipate dehydratase, J) 5-carboxy-2-pentenoate reductase, K) adipyl-CoA/acyl-CoA transferase, L) adipyl-CoA synthase, M) adipyl-CoA hydrolase, N) adipyl-CoA reductase (aldehyde forming), O) 6-aminocaproate transaminase, P) 6-aminocaproate dehydrogenase, Q) 6-aminocaproyl-CoA/acyl-CoA transferase, R) 6-aminocaproyl-CoA synthase, S) amidohydrolase, T) spontaneous cyclization, U) 6-aminocaproyl-CoA reductase (aldehyde forming), V) HMDA transaminase, W) HMDA dehydrogenase.

Figure 11:
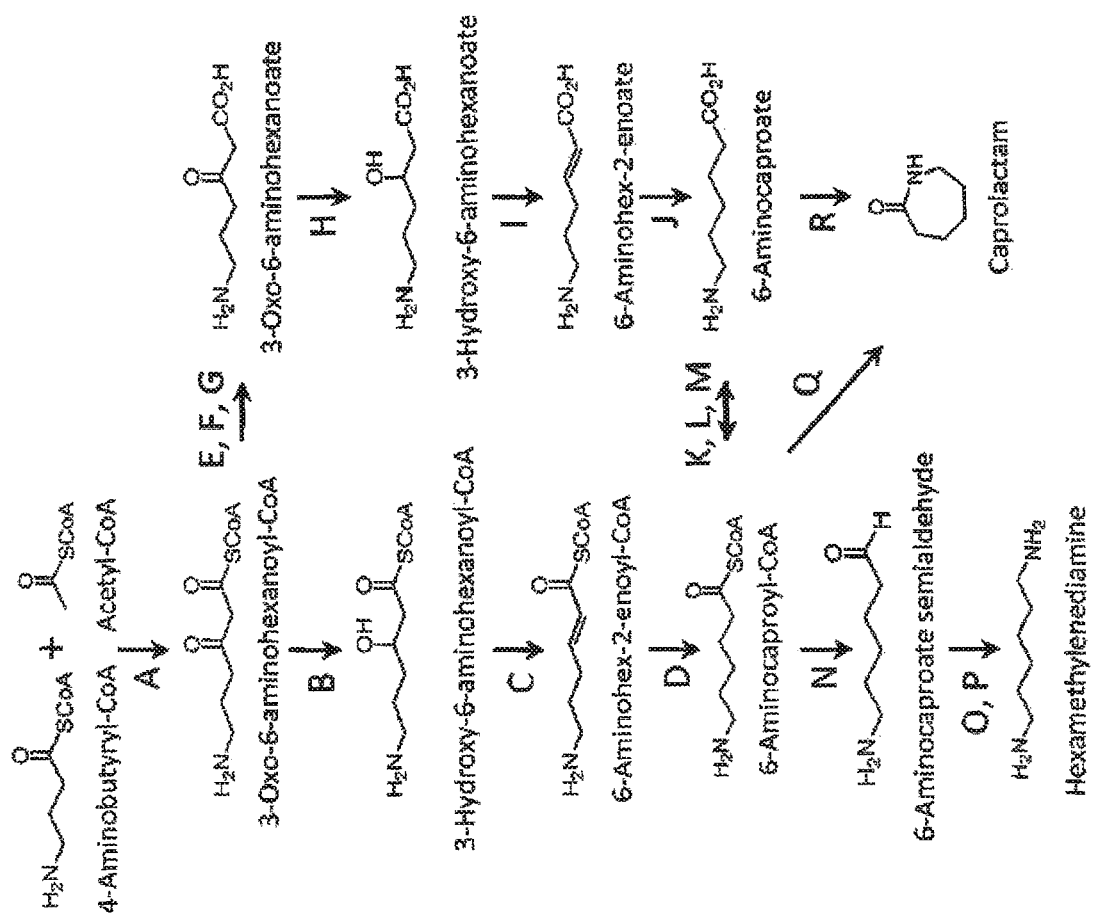

FIG. 11 shows exemplary pathways from 4-aminobutyryl-CoA and acetyl-CoA to hexamethylenediamine and caprolactam. Pathways for the production of 6-aminocaproate, caprolactam, and hexamethylenediamine from 4-aminobutyryl-CoA and acetyl-CoA are depicted. Abbreviations: A) 3-oxo-6-aminohexanoyl-CoA thiolase, B) 3-oxo-6-aminohexanoyl-CoA reductase, C) 3-hydroxy-6-aminohexanoyl-CoA dehydratase, D) 6-aminohex-2-enoyl-CoA reductase, E) 3-oxo-6-aminohexanoyl-CoA/acyl-CoA transferase, F) 3-oxo-6-aminohexanoyl-CoA synthase, G) 3-oxo-6-aminohexanoyl-CoA hydrolase, H) 3-oxo-6-aminohexanoate reductase, I) 3-hydroxy-6-aminohexanoate dehydratase, J) 6-aminohex-2-enoate reductase, K) 6-aminocaproyl-CoA/acyl-CoA transferase, L) 6-aminocaproyl-CoA synthase, M) 6-aminocaproyl-CoA hydrolase, N) 6-aminocaproyl-CoA reductase (aldehyde forming), O) HMDA transaminase, P) HMDA dehydrogenase, Q) spontaneous cyclization, R) amidohydrolase.

Figure 12:
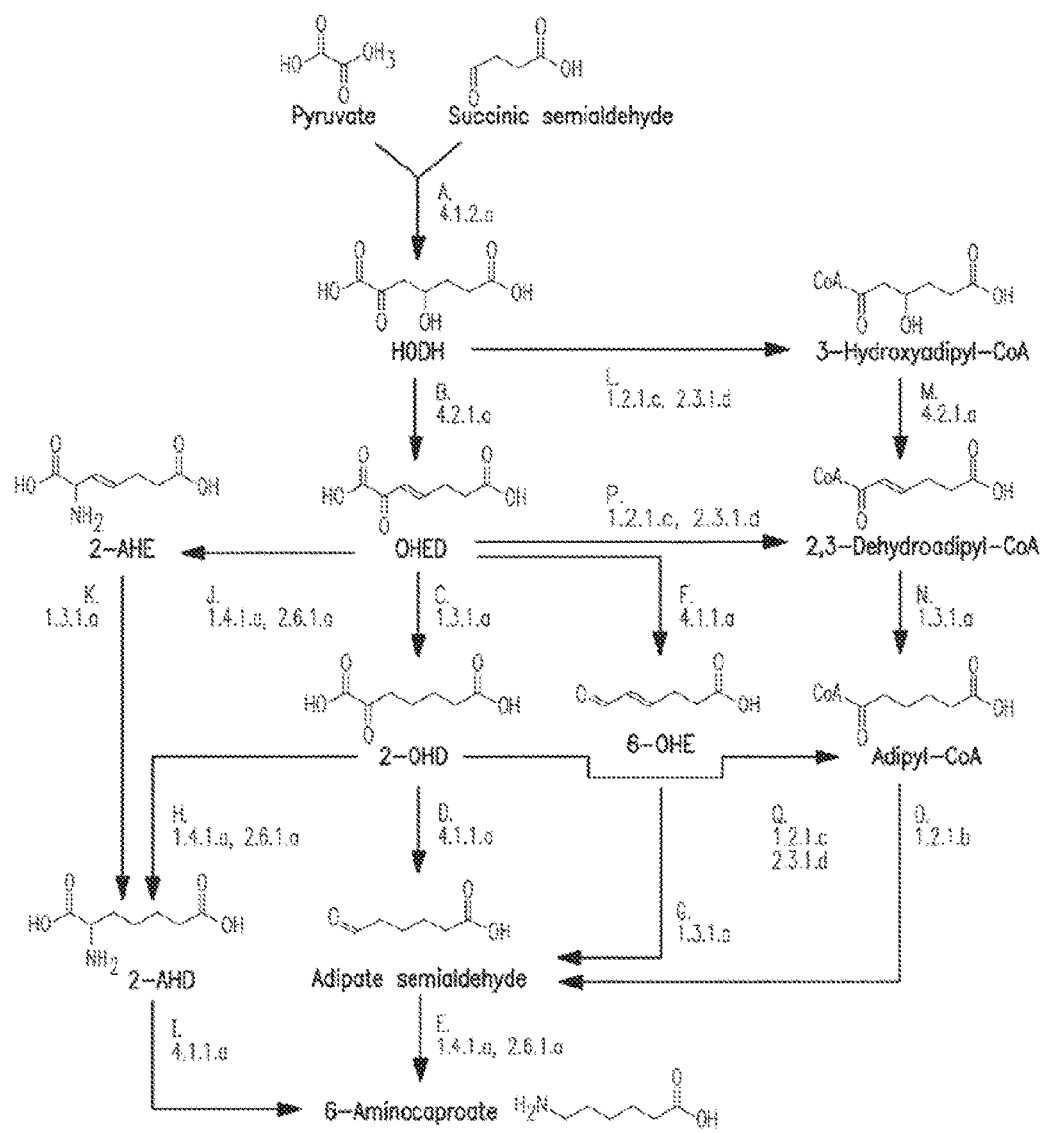

FIG. 12 shows pathways to 6-aminocaproate from pyruvate and succinic semialdehyde. Enzymes are A) HODH aldolase, B) OHED hydratase, C) OHED reductase, D) 2-OHD decarboxylase, E) adipate semialdehyde aminotransferase and/or adipate semialdehyde oxidoreductase (aminating), F) OHED decarboxylase, G) 6-OHE reductase, H) 2-OHD aminotransferase and/or 2-OHD oxidoreductase (aminating), I) 2-AHD decarboxylase, J) OHED aminotransferase and/or OHED oxidoreductase (aminating), K) 2-AHE reductase, L) HODH formate-lyase and/or HODH dehydrogenase, M) 3-hydroxyadipyl-CoA dehydratase, N) 2,3-dehydroadipyl-CoA reductase, O) adipyl-CoA dehydrogenase, P) OHED formate-lyase and/or OHED dehydrogenase, Q) 2-OHD formate-lyase and/or 2-OHD dehydrogenase. Abbreviations are: HODH=4-hydroxy-2-oxoheptane-1,7-dioate, OHED=2-oxohept-4-ene-1,7-dioate, 2-OHD=2-oxoheptane-1,7-dioate, 2-AHE=2-aminohept-4-ene-1,7-dioate, 2-AHD=2-aminoheptane-1,7-dioate, and 6-OHE=6-oxohex-4-enoate.

Figure 13:
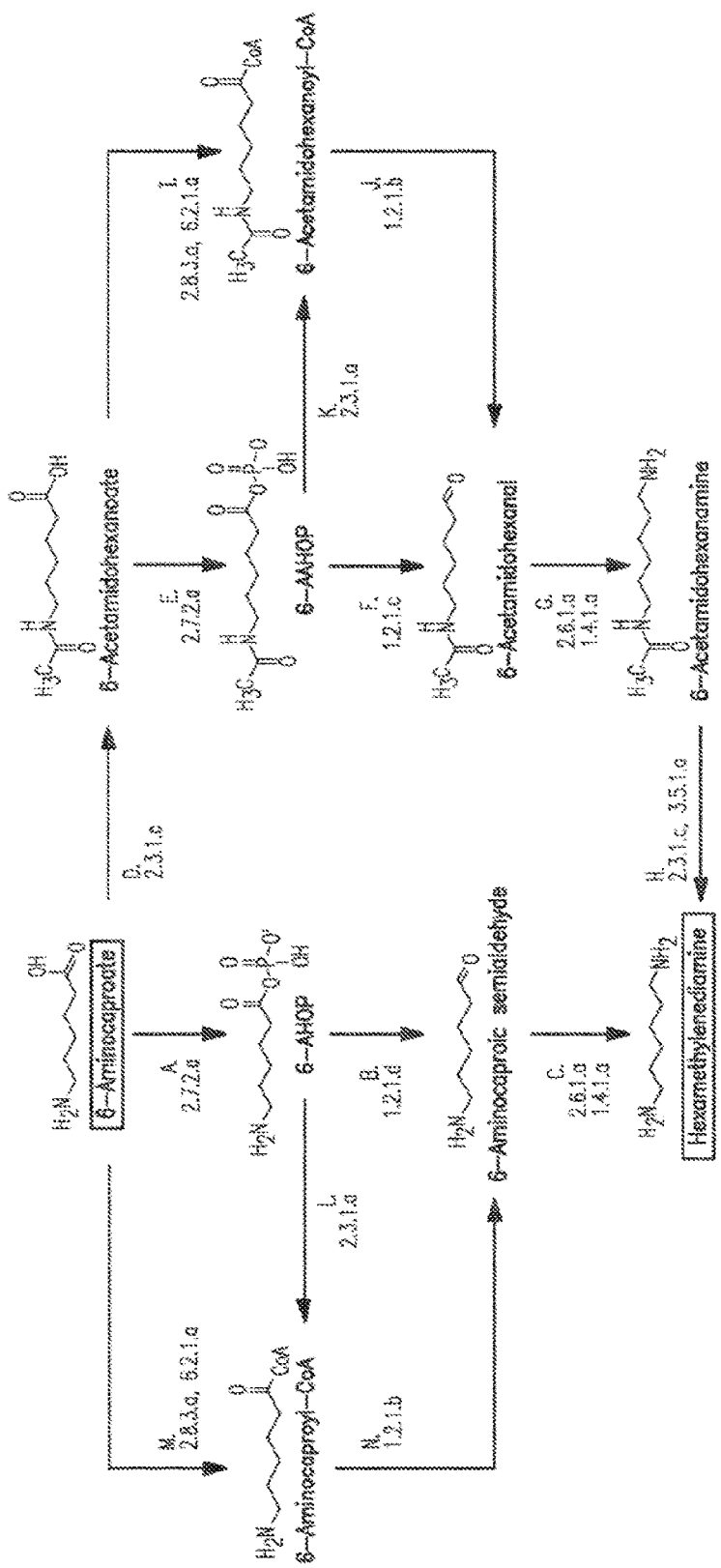

FIG. 13 shows pathways to hexamethylenediamine from 6-aminocapropate. Enzymes are A) 6-aminocaproate kinase, B) 6-AHOP oxidoreductase, C) 6-aminocaproic semialdehyde aminotransferase and/or 6-aminocaproic semialdehyde oxidoreductase (aminating), D) 6-aminocaproate N-acetyltransferase, E) 6-acetamidohexanoate kinase, F) 6-AAHOP oxidoreductase, G) 6-acetamidohexanal aminotransferase and/or 6-acetamidohexanal oxidoreductase (aminating), H) 6-acetamidohexanamine N-acetyltransferase and/or 6-acetamidohexanamine hydrolase (amide), I) 6-acetamidohexanoate CoA transferase and/or 6-acetamidohexanoate CoA ligase, J) 6-acetamidohexanoyl-CoA oxidoreductase, K) 6-AAHOP acyltransferase, L) 6-AHOP acyltransferase, M) 6-aminocaproate CoA transferase and/or 6-aminocaproate CoA ligase, N) 6-aminocaproyl-CoA oxidoreductase. Abbreviations are: 6-AAHOP=[(6-acetamidohexanoyl)oxy]phosphonate and 6-AHOP=[(6-aminohexanoyl)oxy]phosphonate.

FIG. 14 shows: A) the acetyl-CoA cycle of arginine biosynthesis. Reactions (1) and (2) are catalyzed by ornithine acetyltransferase with acetylglutamate synthase and ornithine acyltransferase functionality. Reaction 3 is a lumped reaction catalyzed by acetylglutamate kinase, N-acetylglutamylphosphate reductase, and acetylornithine aminotransferase; B) the acetyl-CoA cycle of HMDA biosynthesis. Reactions (1) and (2) are catalyzed by HMDA acetyltransferase. Reaction (3) is a lumped reaction that includes all pathways to 6-acetamidohexanamine from 6-acetamidohexanoate shown in FIG. 13.

Figure 15:
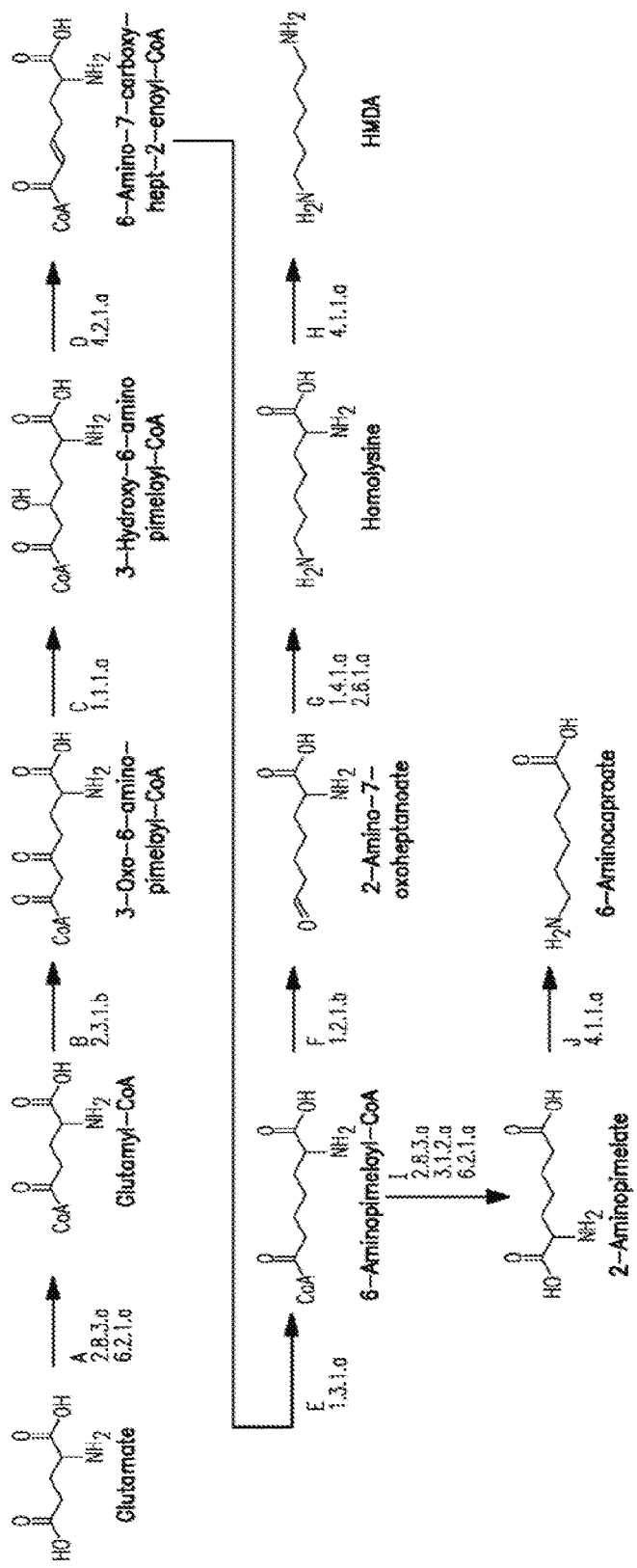

FIG. 15 shows exemplary pathways from glutamate to hexamethylenediamine (HMDA) and 6-aminocaproate. The enzymes are designated as follows: A) glutamyl-CoA transferase and/or ligase, B) beta-ketothiolase, C) 3-oxo-6-aminopimeloyl-CoA oxidoreductase, D) 3-hydroxy-6-aminopimeloyl-CoA dehydratase, E) 6-amino-7-carboxyhept-2- enoyl-CoA reductase, F) 6-aminopimeloyl-CoA reductase (aldehyde forming), G) 2-amino-7-oxoheptanoate aminotransferase and/or aminating oxidoreductase, H) homolysine decarboxylase, I) 6-aminopimeloyl-CoA hydrolase, transferase and/or ligase, J) 2-aminopimelate decarboxylase.

Figure 16:
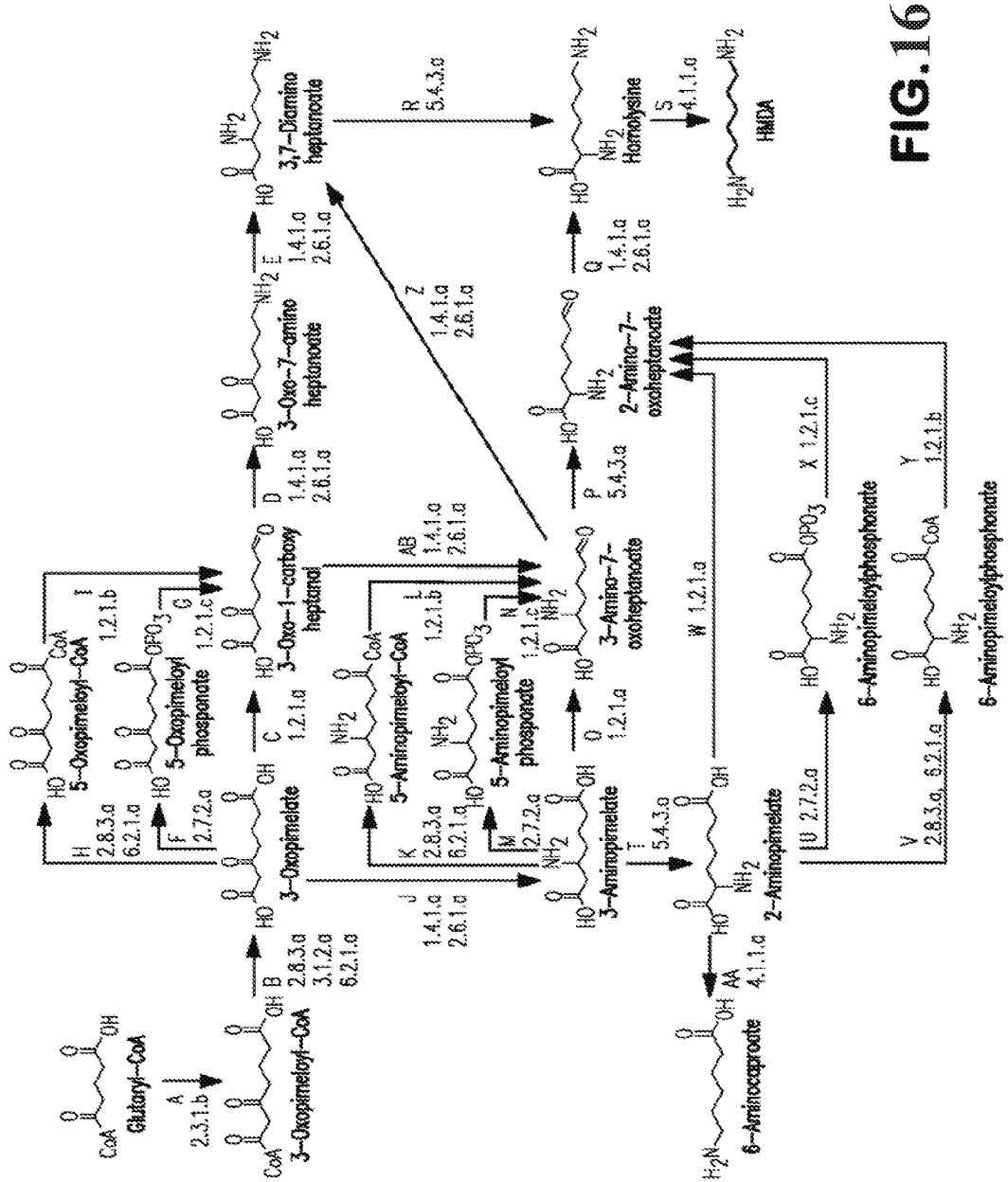

FIG. 16 shows exemplary pathways from glutaryl-CoA to hexamethylenediamine (HMDA) and 6-aminocaproate. The enzymes are designated as follows: A) glutaryl-CoA beta-ketothiolase, B) 3-oxopimeloyl-CoA hydrolase, transferase and/or ligase, C) 3-oxopimelate reductase, D) 3-oxo-1-carboxyheptanal 7-aminotransferase and/or 7-aminating oxidoreductase, E) 3-oxo-7-aminoheptanoate 3-aminotransferase and/or 3-aminating oxidoreductase, F) 3-oxopimelate kinase, G) 5-oxopimeloylphosphonate reductase, H) 3-oxopimelate CoA transferase and/or ligase, I) 5-oxopimeloyl-CoA reductase (aldehyde forming), J) 3-oxopimelate 3-aminotransferase and/or 3-aminating oxidoreductase, K) 3-aminopimelate CoA transferase and/or ligase, L) 5-aminopimeloyl-CoA reductase (aldehyde forming), M) 3-aminopimelate kinase, N) 5-aminopimeloylphosphonate reductase, O) 3-aminopimelate reductase, P) 3-amino-7-oxoheptanoate 2,3-aminomutase, Q) 2-amino-7-oxoheptanoate 7-aminotransferase and/or aminating oxidoreductase, R) 3,7-diaminoheptanoate 2,3-aminomutase, S) homolysine decarboxylase, T) 3-aminopimelate 2,3-aminomutase, U) 2-aminopimelate kinase, V) 2-aminopimelate CoA transferase and/or ligase, W) 2-aminopimelate reductase, X) 6-aminopimeloylphosphonate reductase, Y) 6-aminopimeloyl-CoA reductase (aldehyde forming), Z) 3-amino-7-oxoheptanoate 7-aminotransferase and/or 7-aminating oxidoreductase, AA) 2-aminopimelate decarboxylase and AB) 3-oxo-1-carboxyheptanal 3-aminotransferase and/or 3-aminating oxidoreductase.

Figure 17:
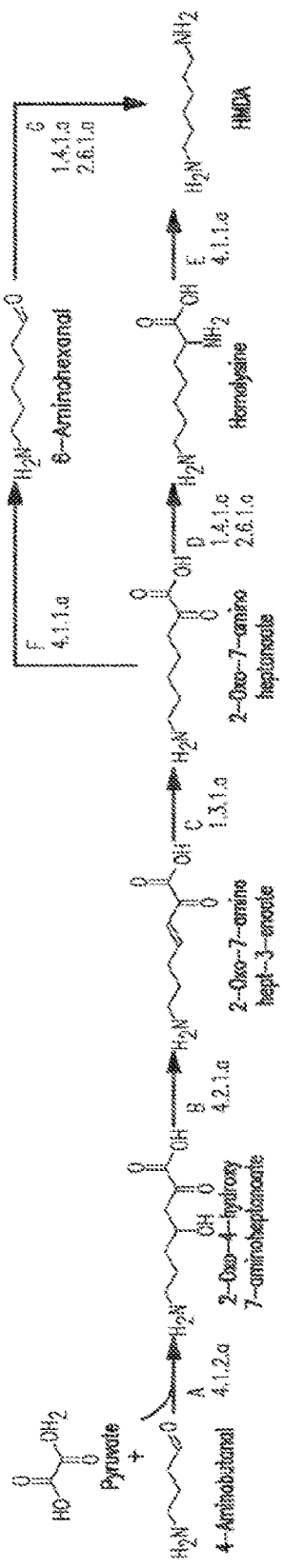

FIG. 17 shows an exemplary pathway from pyruvate and 4-aminobutanal to hexamethylenediamine (HMDA). The enzymes are designated as follows: A) 2-oxo-4-hydroxy-7-aminoheptanoate aldolase, B) 2-oxo-4-hydroxy-7-aminoheptanoate dehydratase, C) 2-oxo-7-aminohept-3-enoate reductase, D) 2-oxo-7-aminoheptanoate aminotransferase and/or aminating oxidoreductase, E) homolysine decarboxylase, F) 2-oxo-7-aminoheptanoate decarboxylase, G) 6-aminohexanal aminotransferase and/or 6-aminohexanal aminating oxidoreductase.

Figure 18:
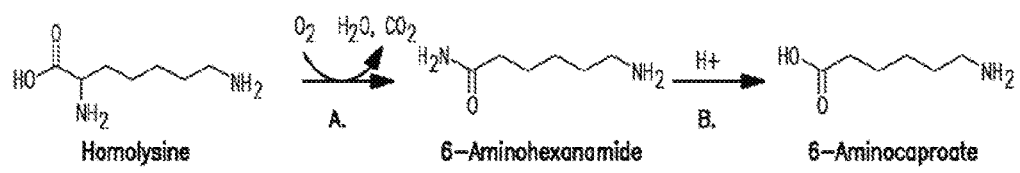

FIG. 18 shows an exemplary pathway from homolysine to 6-aminocaproate. Step A is catalyzed by homolysine 2-monooxygenase. Step B is hydrolysis, catalyzed by dilute acid or base.

Figure 19:
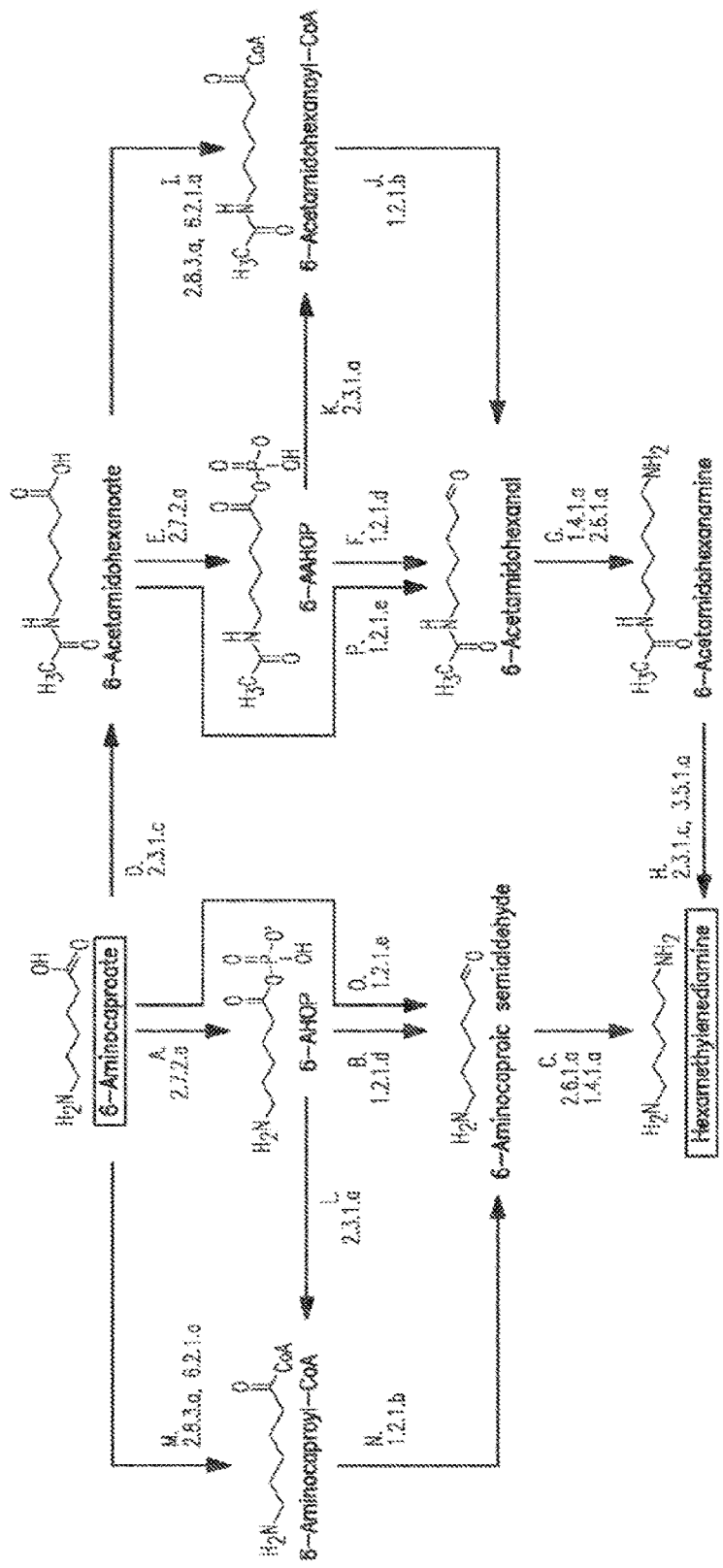

FIG. 19 shows exemplary pathways from 6-aminocaproate to hexamethylenediamine. This figure depicts additional pathways further to those presented in FIG. 13. The enzymes are designated as follows: A) 6-aminocaproate kinase, B) 6-AHOP oxidoreductase, C) 6-aminocaproic semialdehyde aminotransferase and/or 6-aminocaproic semialdehyde oxidoreductase (aminating), D) 6-aminocaproate N-acetyltransferase, E) 6-acetamidohexanoate kinase, F) 6-AAHOP oxidoreductase, G) 6-acetamidohexanal aminotransferase and/or 6-acetamidohexanal oxidoreductase (aminating), H) 6-acetamidohexanamine N-acetyltransferase and/or 6-acetamidohexanamine hydrolase (amide), I) 6-acetamidohexanoate CoA transferase and/or 6-acetamidohexanoate CoA ligase, J) 6-acetamidohexanoyl-CoA oxidoreductase, K) 6-AAHOP acyltransferase, L) 6-AHOP acyltransferase, M) 6-aminocaproate CoA transferase and/or 6-aminocaproate CoA ligase, N) 6-aminocaproyl-CoA oxidoreductase, O) 6-aminocaproate reductase and P) 6-acetamidohexanoate reductase. Abbreviations are: 6-AAHOP=[(6-acetamidohexanoyl)oxy]phosphonate and 6-AHOP=[(6-aminohexanoyl)oxy]phosphonate.

Figure 20:
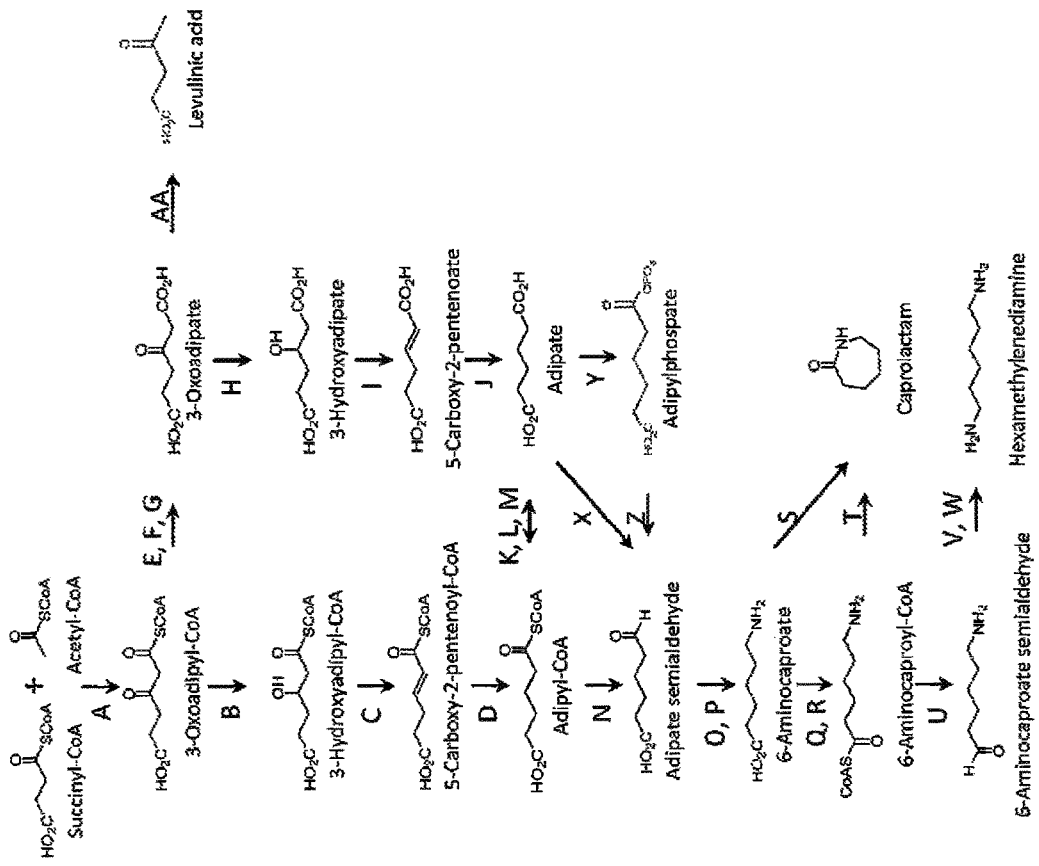

FIG. 20 shows exemplary pathways from succinyl-CoA and acetyl-CoA to hexamethylenediamine (HMDA), caprolactam or levulinic acid. Pathways for the production of adipate, 6-aminocaproate, caprolactam, hexamethylenediamine and levulinic acid from succinyl-CoA and acetyl-CoA are depicted. This figure depicts additional pathways further to those presented in FIG. 10. The enzymes are designated as follows: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) 3-oxoadipyl-CoA/acyl-CoA transferase, F) 3-oxoadipyl-CoA synthase, G) 3-oxoadipyl-CoA hydrolase, H) 3-oxoadipate reductase, I) 3-hydroxyadipate dehydratase, J) 5-carboxy-2-pentenoate reductase, K) adipyl-CoA/acyl-CoA transferase, L) adipyl-CoA synthase, M) adipyl-CoA hydrolase, N) adipyl-CoA reductase (aldehyde forming), O) 6-aminocaproate transaminase, P) 6-aminocaproate dehydrogenase, Q) 6-aminocaproyl-CoA/acyl-CoA transferase, R) 6-aminocaproyl-CoA synthase, S) amidohydrolase, T) spontaneous cyclization, U) 6-aminocaproyl-CoA reductase (aldehyde forming), V) HMDA transaminase, W) HMDA dehydrogenase, X) adipate reductase, Y) adipate kinase, Z) adipyl-phosphate reductase, and AA) 3-oxoadipate decarboxylase.

Figure 21:
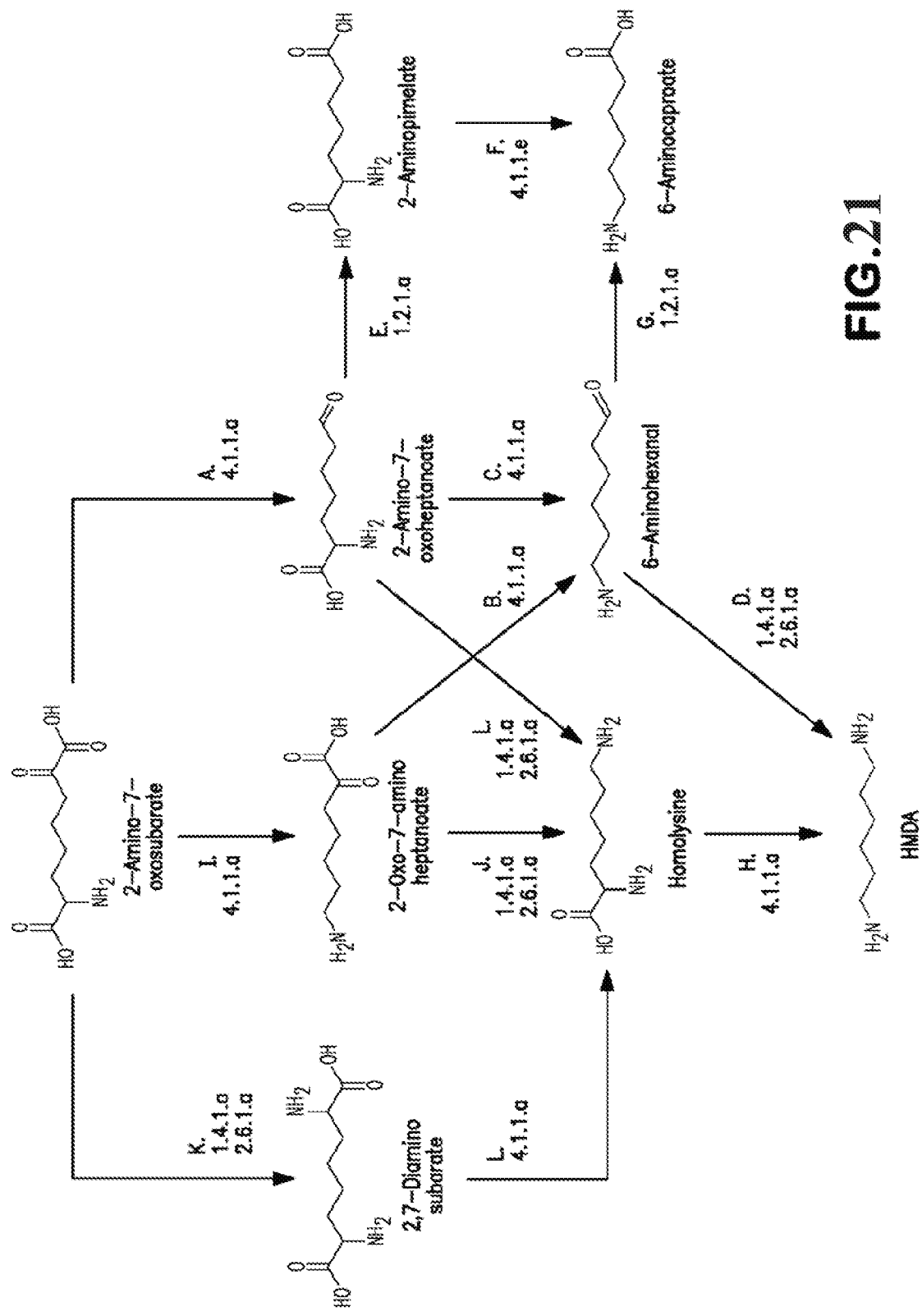

FIG. 21 shows exemplary pathways from 2-amino-7-oxosubarate to hexamethylenediamine (HMDA) and 6-aminocaproate. The enzymes are designated as follows: A) 2-amino-7-oxosubarate keto-acid decarboxylase, B) 2-amino-7-oxoheptanoate decarboxylase, C) 6-aminohexanal aminating oxidoreductase and/or 6-aminohexanal aminotransferase, D) 2-amino-7-oxoheptanoate oxidoreductase, E) 2-aminopimelate decarboxylase, F) 6-aminohexanal oxidoreductase, G) 2-amino-7-oxoheptanoate decarboxylase, H) homolysine decarboxylase, I) 2-amino-7-oxosubarate amino acid decarboxylase, J) 2-oxo-7-aminoheptanoate aminating oxidoreductase and/or 2-oxo-7-aminoheptanoate aminotransferase, K) 2-amino-7-oxosubarate aminating oxidoreductase and/or 2-amino-7-oxosubarate aminotransferase, L) 2,7-diaminosubarate decarboxylase and M) 2-amino-7-oxoheptanoate aminating oxidoreductase and/or 2-amino-7-oxoheptanoate aminotransferase.

Figure 22:
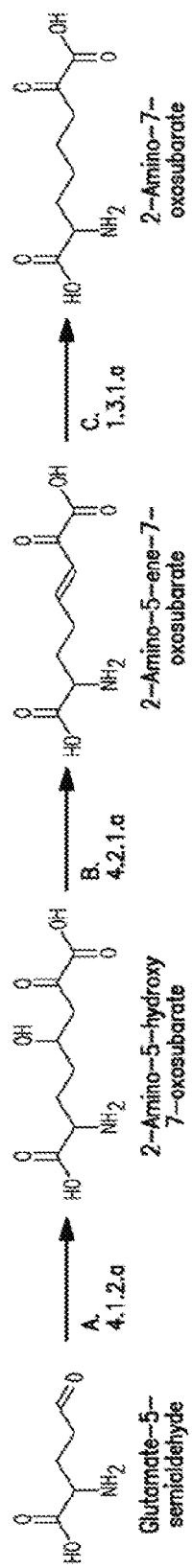

FIG. 22 shows an exemplary pathway from glutamate-5-semialdehyde to 2-amino-7-oxosubarate. The enzymes are designated as follows: A) 2-amino-5-hydroxy-7-oxosubarate aldolase, B) 2-amino-5-hydroxy-7-oxosubarate dehydratase, C) 2-amino-5-ene-7-oxosubarate reductase.

Figure 23:
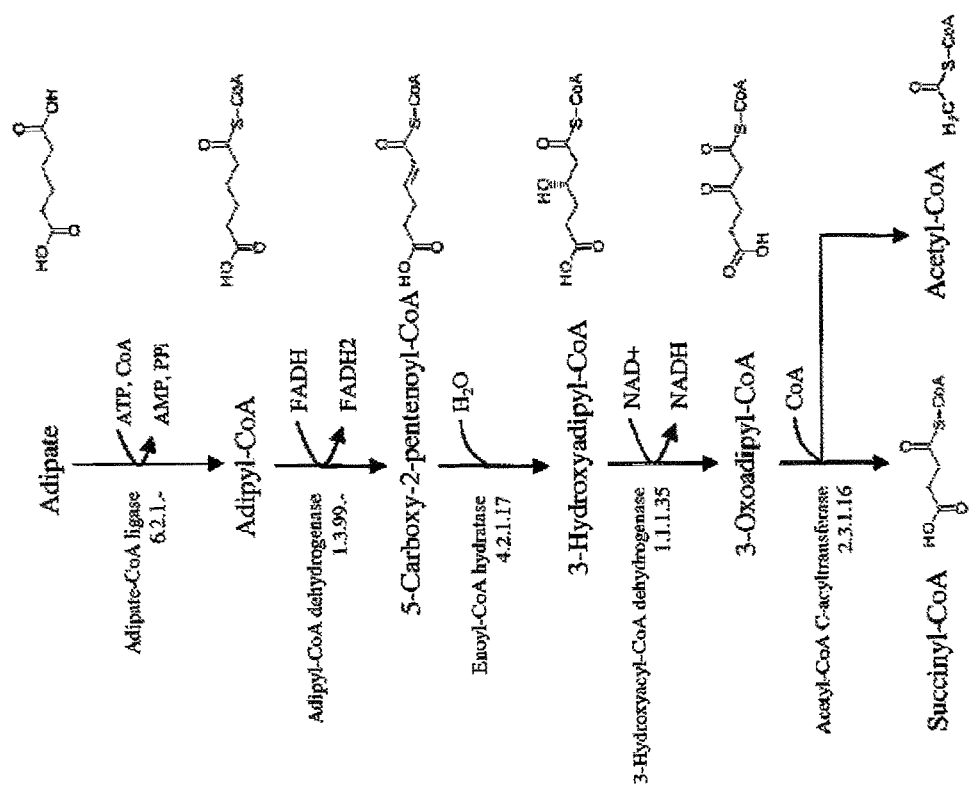

FIG. 23 shows an exemplary pathway for adipate degradation in the peroxisome of *Penicillium chrysogenum*.

Figure 24:
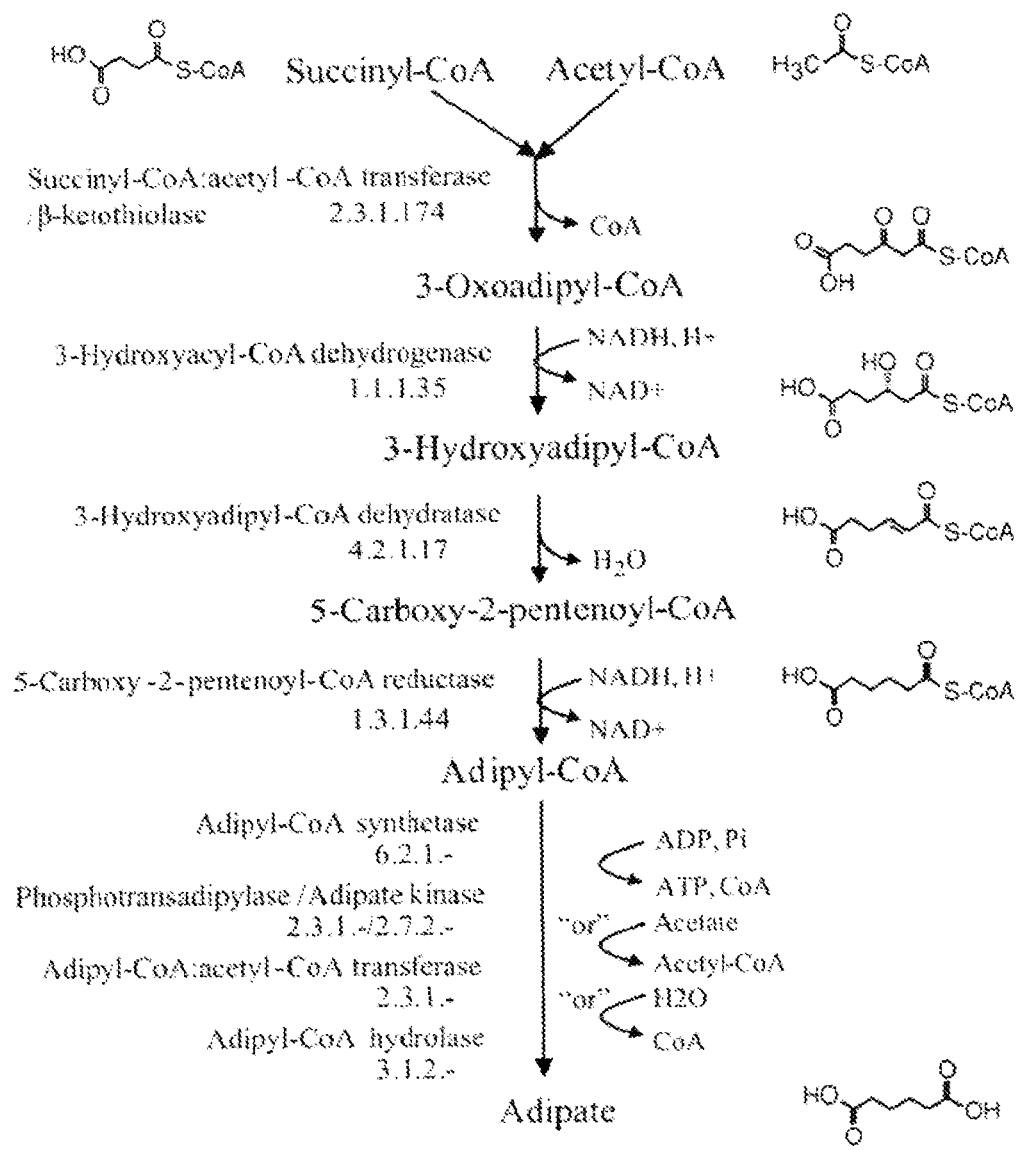

FIG. 24 shows an exemplary pathway for adipate formation via a reverse degradation pathway. Several options are provided for the final conversion of adipyl-CoA to adipate.

Figure 25:
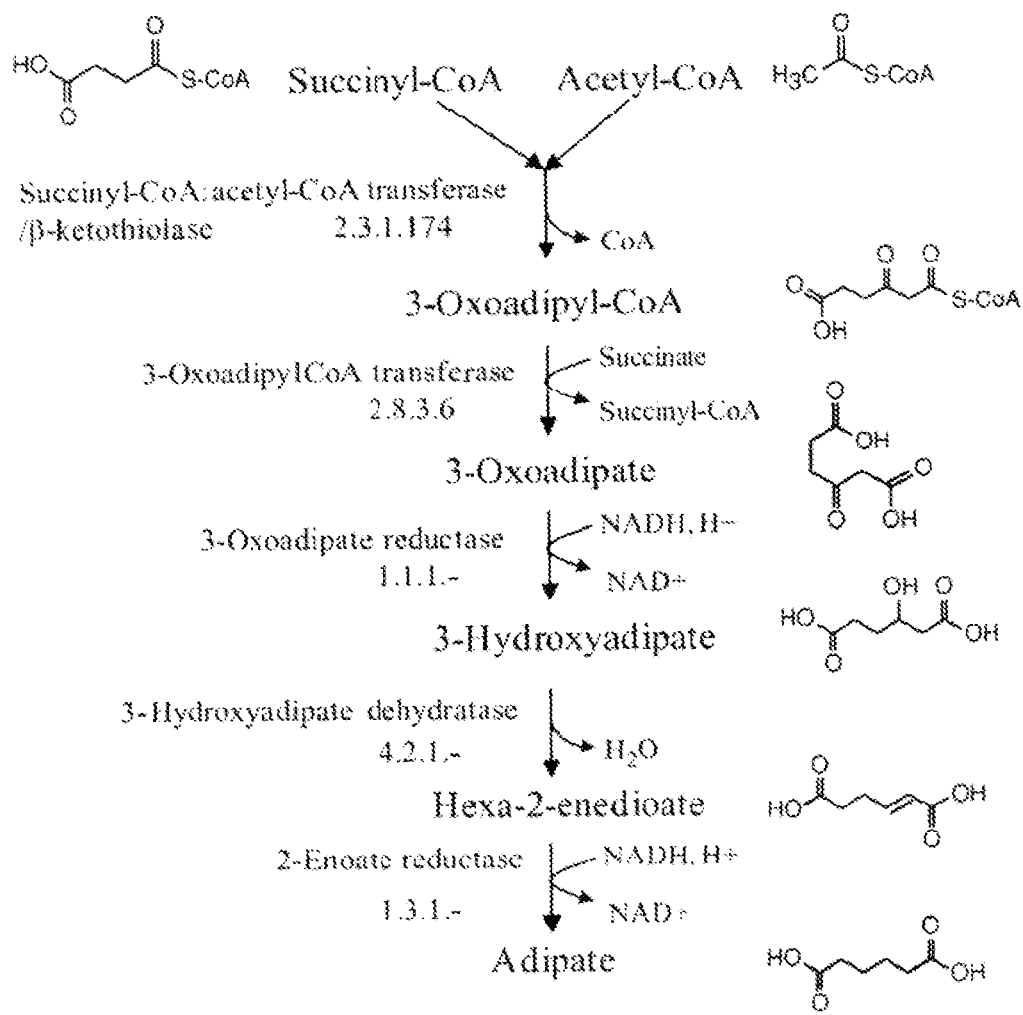

FIG. 25 shows an exemplary pathway for adipate formation via the 3-oxoadipate pathway.

Figure 26:
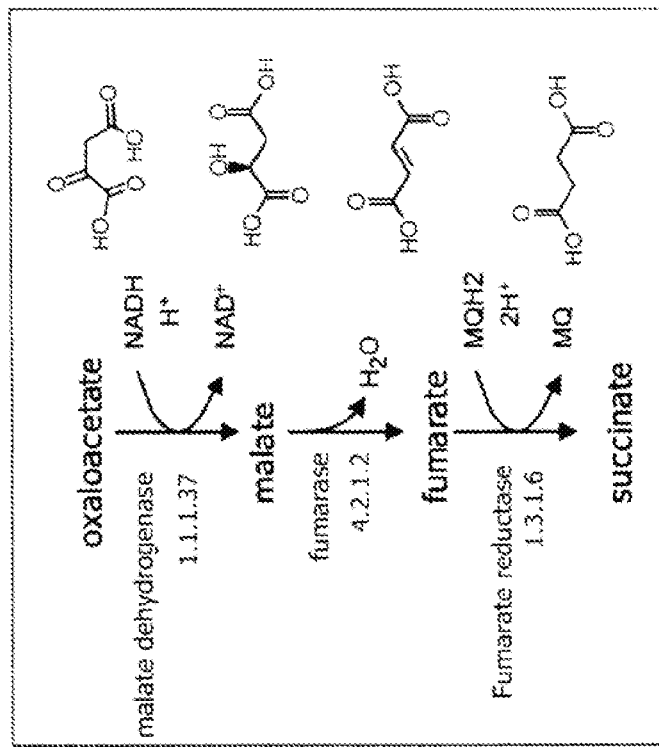
Figure 26:
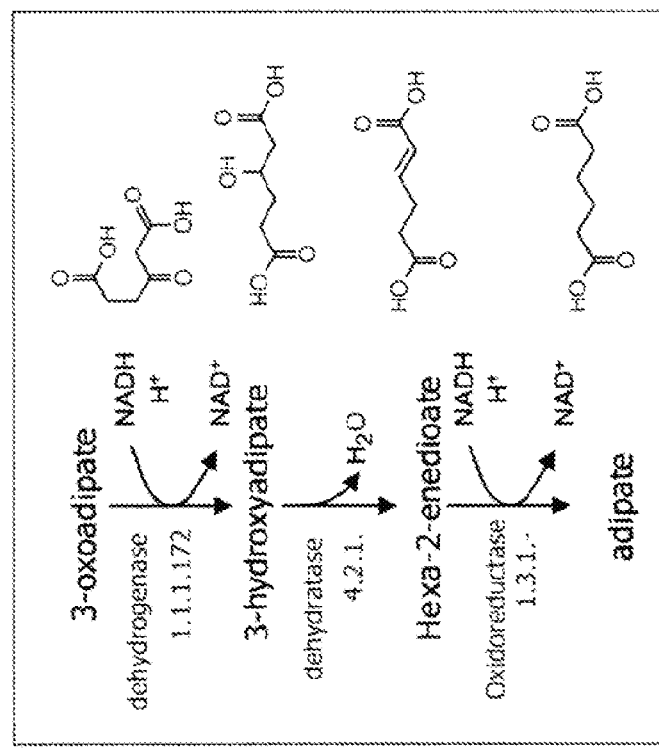

FIG. 26 shows the similar enzyme chemistries of the last three steps of the 3-oxoadipate pathway for adipate synthesis and the reductive TCA cycle.

Figure 27:
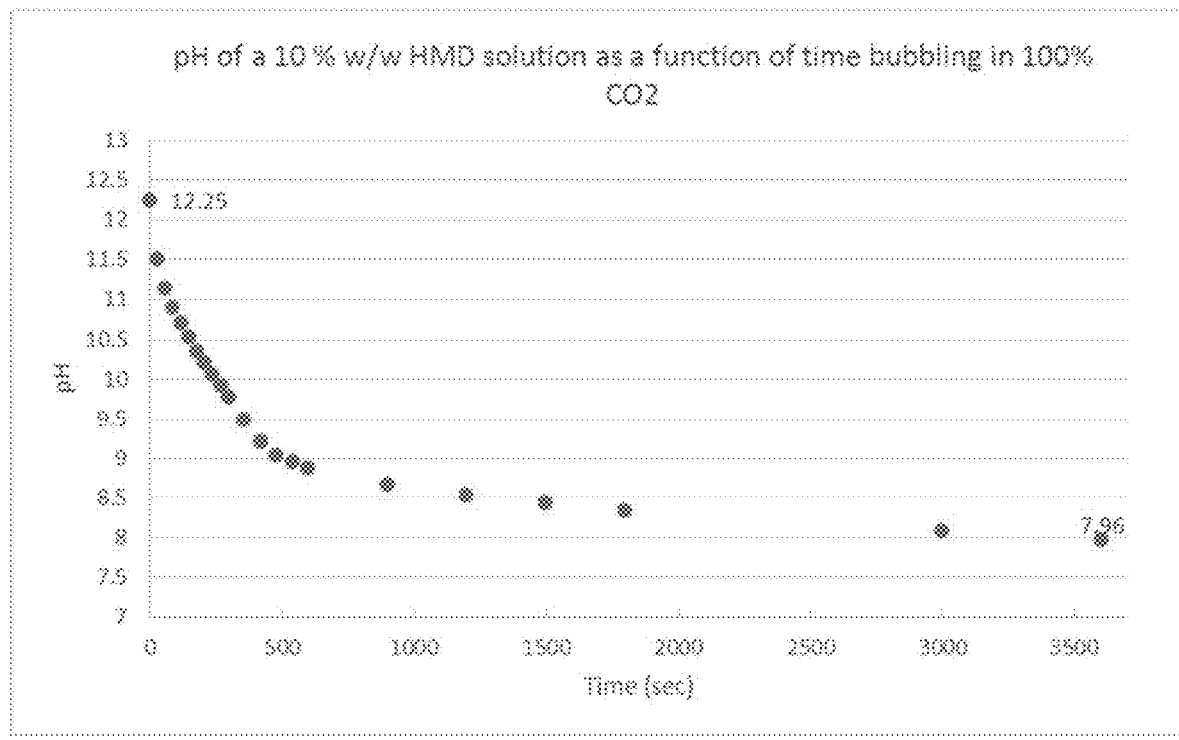

FIG. 27 shows a graphical representation of pH as function of time bubbling in $CO_2$ over 60 minutes.

Figure 28:
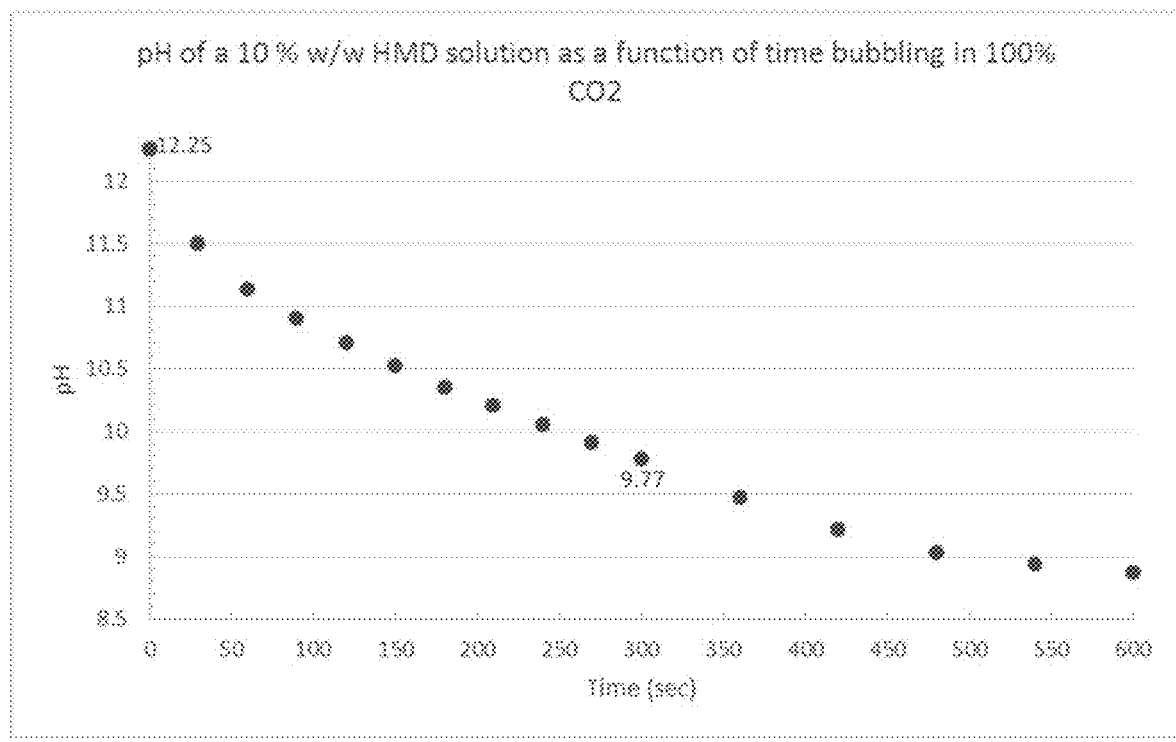

FIG. 28 shows a graphical representation of pH as a function of time bubbling in $CO_2$ for the first 10 minutes.

Figure 29:
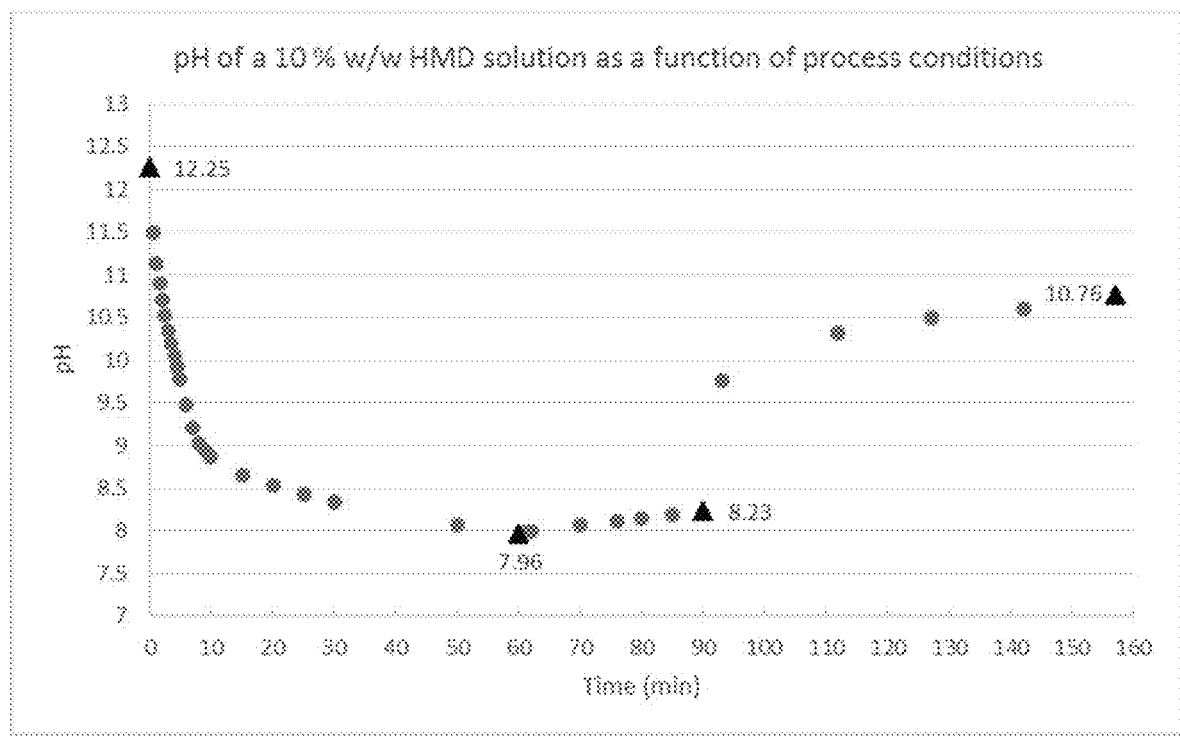

FIG. 29 shows a graphical representation of pH as a function of process conditions shown in Table 1-1.

Figure 30:
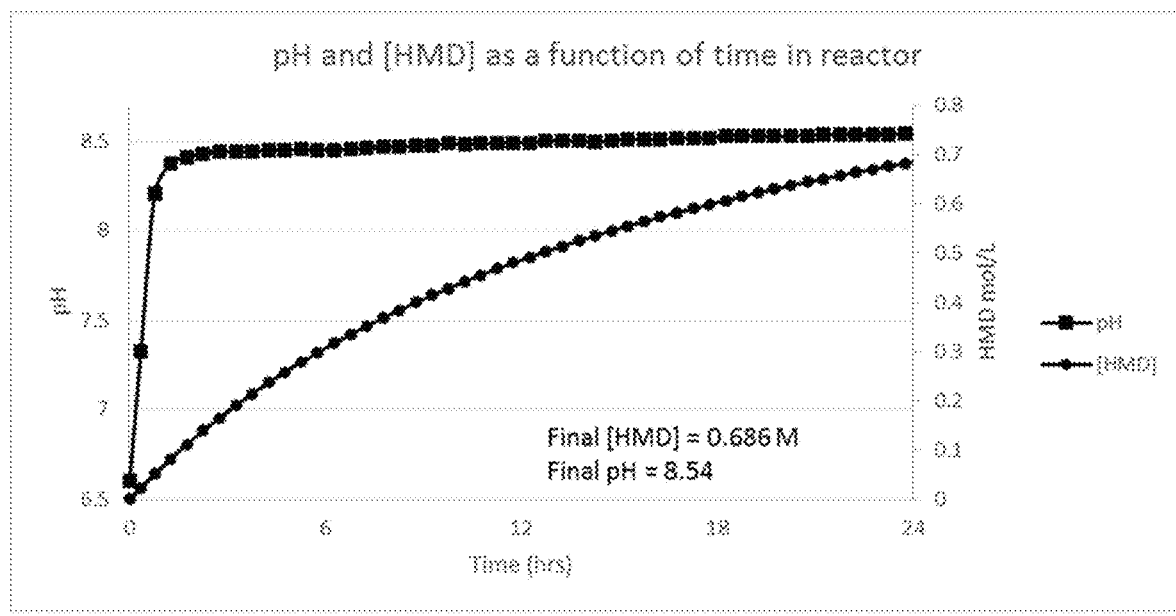

FIG. 30 shows a graphical representation of pH and HMD concentration inside a fermentor as a function of time.

Figure 31:
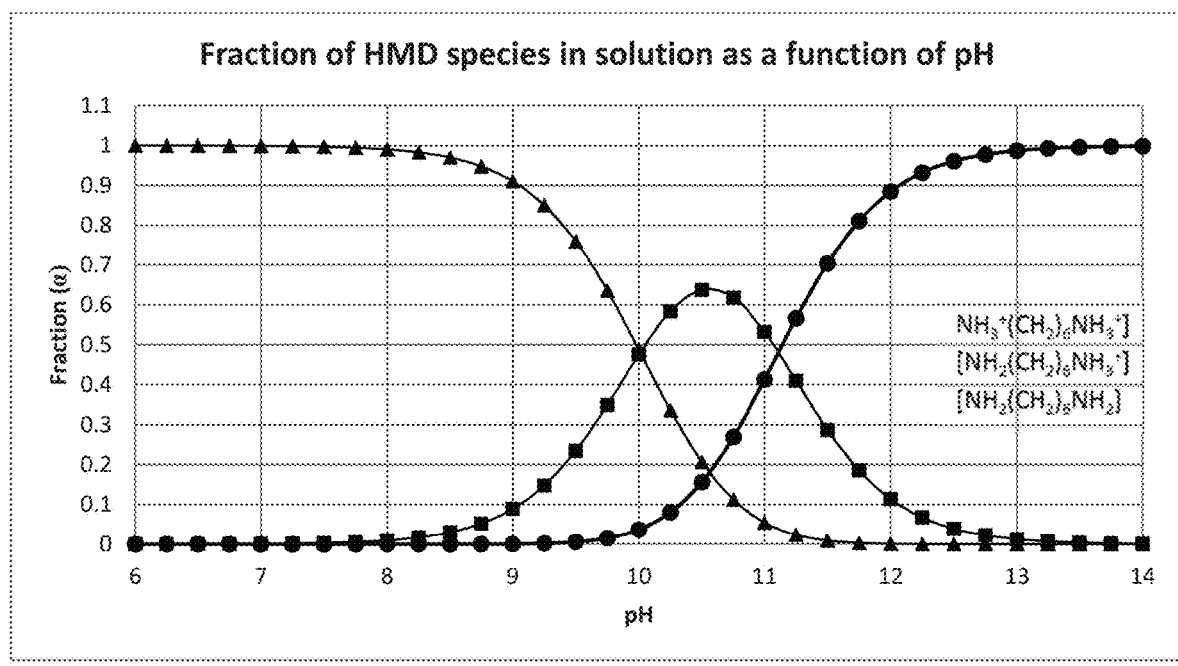

FIG. 31 shows a graphical representation of concentration of HMD species as a function of pH.

Figure 32:
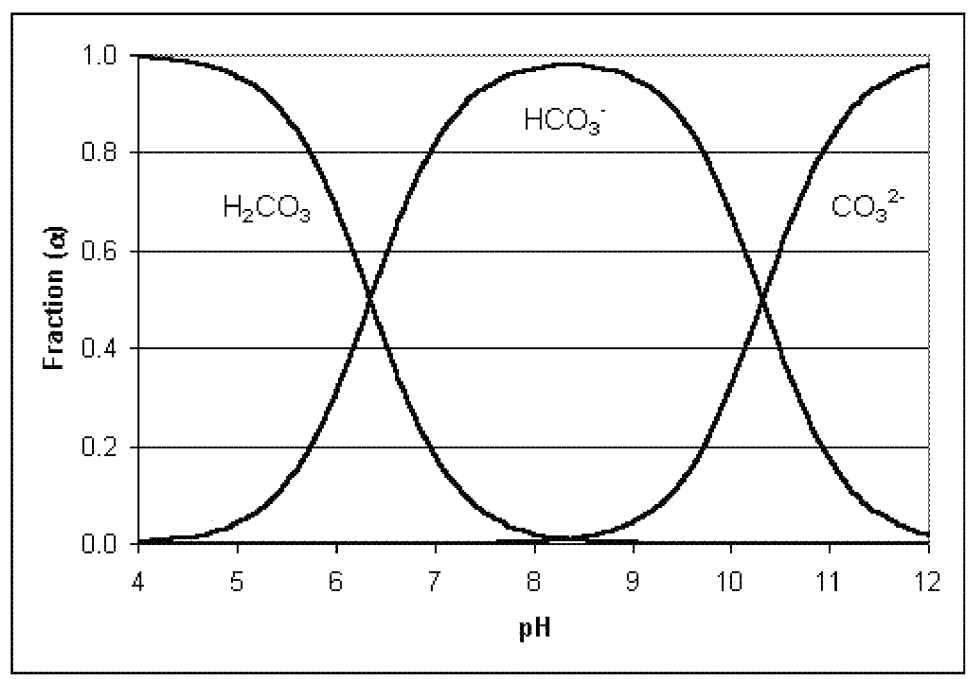

FIG. 32 shows a graphical representation of carbonate species as a function of pH.

Figure 33:
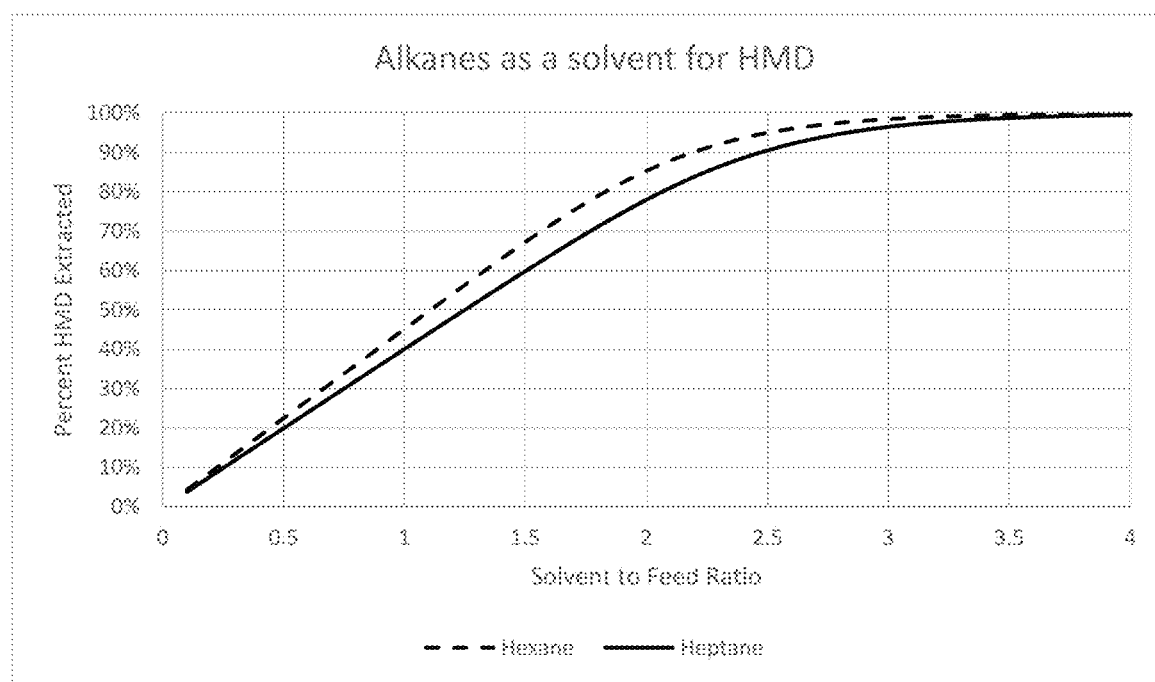

FIG. 33 shows a graphical representation of alkanes as solvents for HMD recovery.

Figure 34:
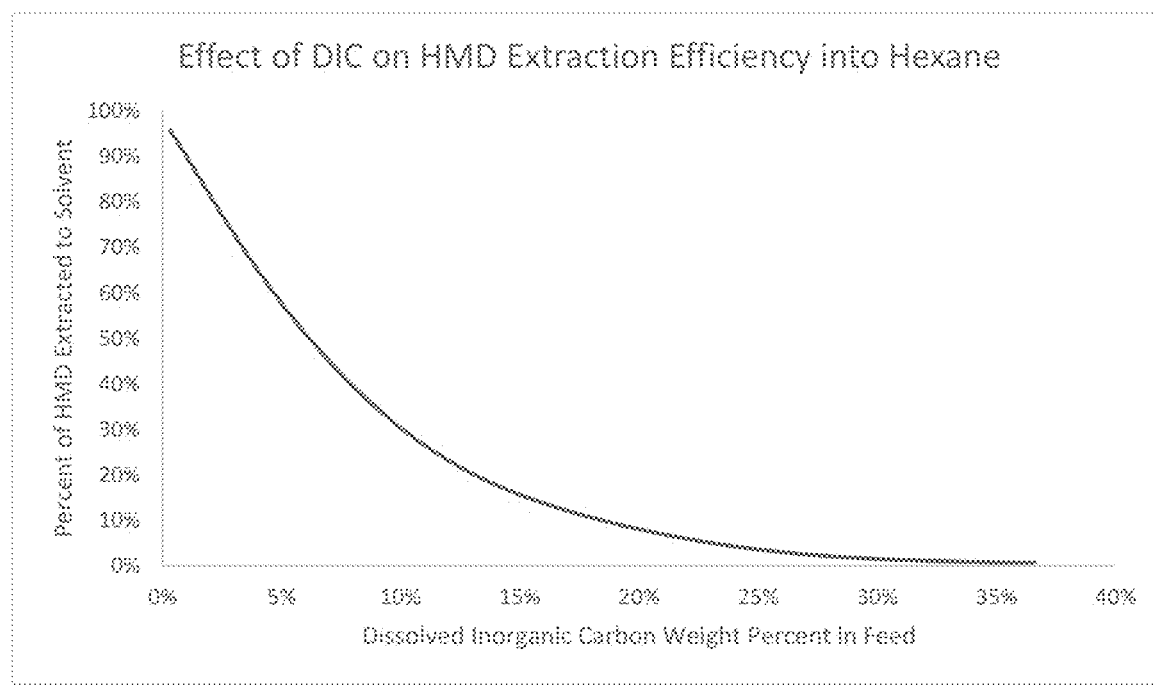

FIG. 34 shows a graphical representation of the effect of DIC on HMD extraction efficiency into hexane.

Figure 35:
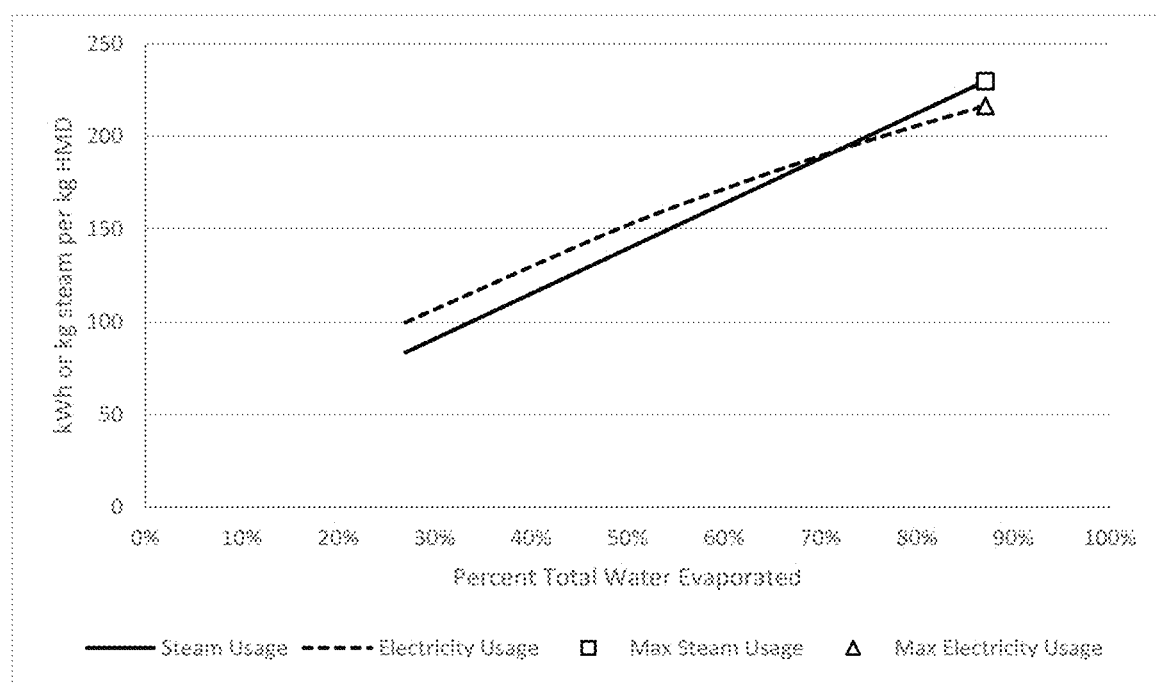

FIG. 35 shows a graphical representation of steam and electricity usages as a function of total water removed when no stripping column is present.

Figure 36:
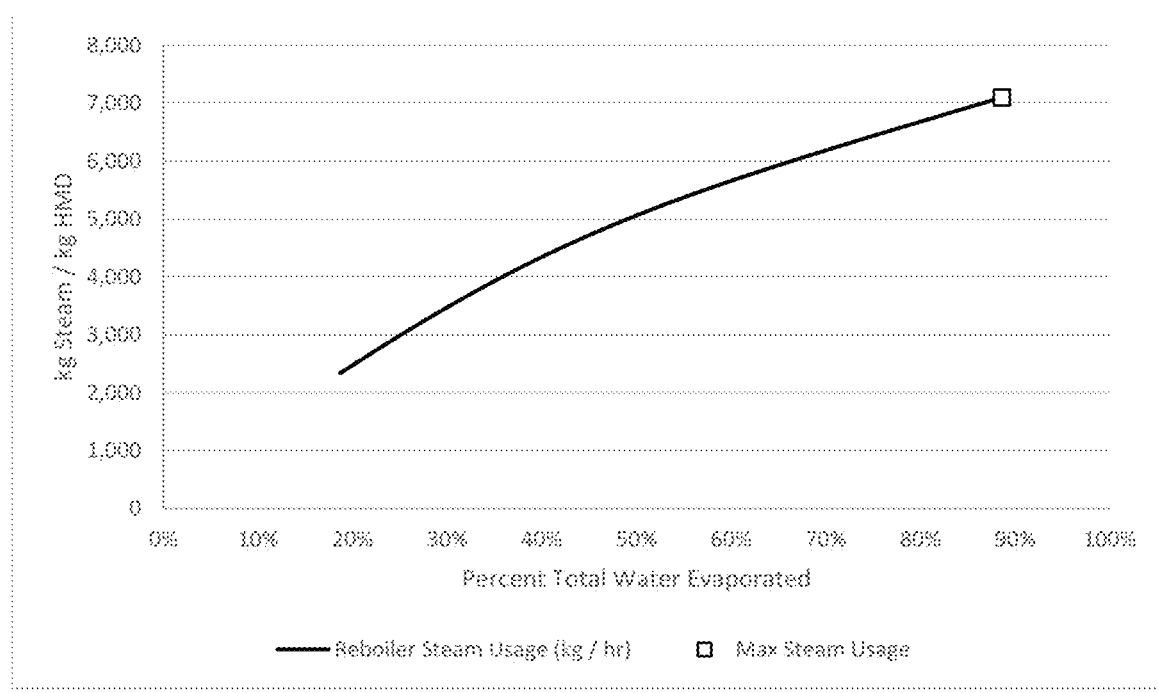

FIG. 36 shows a graphical representation of steam usage in a stripping column when no evaporator used.

DETAILED DESCRIPTION

Disclosed is a process for the production and isolation of a diamine. As referred here, "diamines" include C2 to C7 methylene segments such as hexamethylenediamine (HMD), cadaverine, putrescine, ethylenediamine and heptamethylenediamine, for example. The diamines can have carbon content of C2-C7, C3-C7, preferably C4-C7 or even C4-C12 or C2-C12. It should be understood that for ease of reading, HMD may be described in detail but the disclosed process is applicable to any of the diamines such as cadaverine, putrescine, ethylenediamine and heptamethylenediamine.

Hexamethylenediamine also referred to as 1,6-diaminohexane or 1,6-hexanediamine (abbreviated as HMD) has the chemical formula H2N(CH2)6NH2. HMD is an important raw material in the chemical industry. HMD is used, for example, in the preparation of polyamides, polyureas or polyurethanes and copolymers of these materials.

Cadaverine, also referred to as 1,5-diaminopentane is used as a monomer for polyamine production. Engineered microorganisms suitable for fermentative production of cadaverine have been reported. For example, a method to produce and recover a bio-based amine (e.g. cadaverine) is reported in U.S. Pat. No. 8,906,653 and in the literature by Kind et al. "From zero to hero—Production of bio-based nylon from renewable resources using engineered *Corynebacterium glutamicum*," (Metabolic Engineering, 25 (2014) pp. 113-123) and Kind et al. "Systems-wide metabolic pathway engineering in *Corynebacterium glutamicum* for bio-based production of diaminopentane," (Metabolic Engineering 12 (2010)341-351). These reported processes involve active neutralization of a fermentation broth or cultured medium with an inorganic acid (e.g. sulfuric acid). After fermentation, the cultured medium or broth is alkalized with a strong base to deprotonate the amine, which is then extracted with an organic solvent and subsequently distilled. In these processes, copious amounts of unwanted salt by-products are produced with the amine.

In another method, lysine carbonate prepared in vitro is enzymatically decarboxylated to produce cadaverine carbonate with addition of a dicarboxylic acid salt to maintain suitable pH for the decarboxylation reaction, followed by concentration to generate cadaverine and cadaverine-dicarboxylic acid salt, as reported in International Patent Application Publication No. WO 2006/123778. In still another method, lysine carbonate prepared in vitro is enzymatically decarboxylated to produce cadaverine carbonate which is thermally treated and then distilled to provide cadaverine as reported in International Patent Application Publication No. WO 2010/002000.

Putrescine, also referred to as 1,4-diaminobutane is used as a monomer for polyamine production. Engineered microorganisms suitable for fermentative production of putrescine have been reported. See, for example, Schneider et al. "Improving putrescine production by *Corynebacterium glutamicum* by fine-tuning ornithine transcarbamoylase activity using a plasmid addition system," (Appl Microbiol Biotechnol. 2012; 95(1):169-78); and U.S. Patent Application Publication No. 20140004577A1 "Microorganisms for producing putrescine and method for producing putrescine using same."

Heptamethylenediamine, also referred to as 1,7-diaminoheptane, is used as a monomer for polyamine production. Engineered microorganisms suitable for fermentative production of putrescine have been reported. See, for example International Patent Application Publication No. WO2014105790A2, "Methods of producing 7-carbon chemicals via c1 carbon chain elongation associated with coenzyme b synthesis."

Ethylenediamine is used as a monomer for polyamine production as well as a precursor to other chemicals. Engineered microorganisms for fermentative production of ethylenediamine have been reported. See for example International Patent Application Publication No. WO2014049382A2, "Ethylenediamine fermentative production by a recombinant microorganism."

Hexamethylenediamine also referred to as 1,6-diaminohexane or 1,6-hexanediamine (abbreviated as HMD) has the chemical formula $H_2N(CH_2)_6NH_2$. HMD is an important raw material in the chemical industry. HMD is used, for example, in the preparation of polyamides, polyureas or polyurethanes and copolymers of these materials. Cadaverine, also referred to as 1,5-diaminopentane is used as a monomer for polyamine production. Putrescine, also referred to as 1,4-diaminobutane is used as a monomer for polyamine production. Heptamethylenediamine, also referred to as 1,7-diaminoheptane, is used as a monomer for polyamine production. Ethylenediamine is used as a monomer for polyamine production as well as a precursor to other chemicals. Engineered microorganisms for fermentative production of these compounds and other diamines or their immediate precursors have been reported. Typically, processes for their fermentation and isolation require acids and bases that generate salt by-products.

During the fermentation process, which utilizes carbon dioxide, at least one or more of diamine carbonate, diamine bicarbonate, and/or diamine bis-bicarbonate (referred to herein as the diamine "Carbonates") and, optionally diamine carbamate or diamine biscarbamate (referred to herein as the diamine "Carbamates", are produced. The disclosed process further provides increased yields of the diamines and improves the purification of the desired diamine using organic solvent-based extraction.

Figure 1:
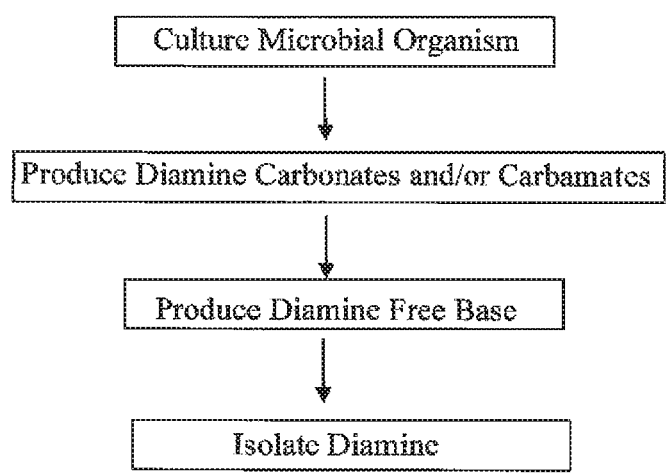
FIG. 1 is a flow chart illustrating one embodiment of the invention of preparing a diamine.

FIG. 1 schematically illustrates one embodiment of the invention that includes the process steps of culturing a microbial organism, using the cultured microbial organism to produce one or more HMD-Carbonates and/or HMD Carbamates, producing an HMD neutral-charge or free base having the formula H2N—(CH2)6-NH2 and having a higher solubility in hydrophobic organic solvents compared the HMD salts or HMD Carbonates and/or Carbamates, and isolating the HMD neutral-charge or HMD free base.

Figure 2:
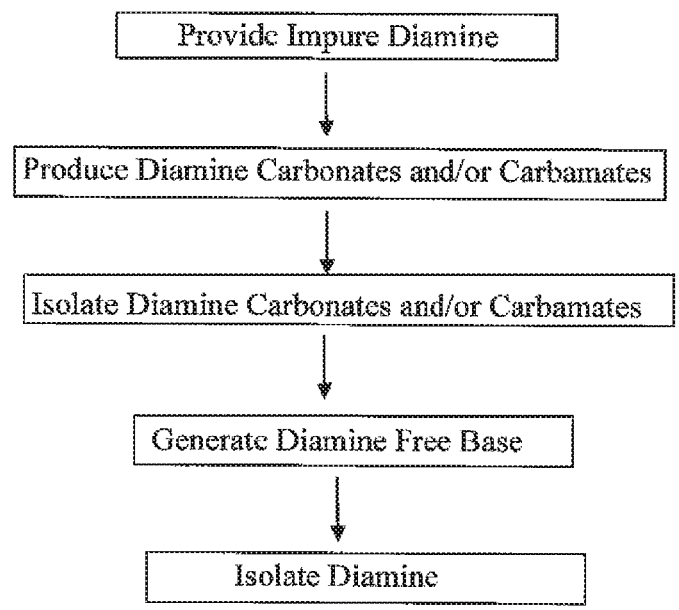
FIG. 2 is a flow chart illustrating another embodiment of the invention of preparing diamine.

FIG. 2 schematically illustrates another embodiment of the invention that includes the process steps of providing an impure, biosynthetic source of HMD, producing one or more HMD-Carbonates and/or Carbamates that are charged compounds in the presence of CO2, isolating or separating the HMD Carbonates and/or Carbamates from undesired byproducts or materials, producing an HMD neutral-charge or HMD free base compound having the formula H2N(CH2)6NH2 and having a higher solubility in hydrophobic organic solvents compared to the charged HMD Carbonates and/or Carbamates, and isolating the HMD neutral-charge or HMD free base.

Figure 3:
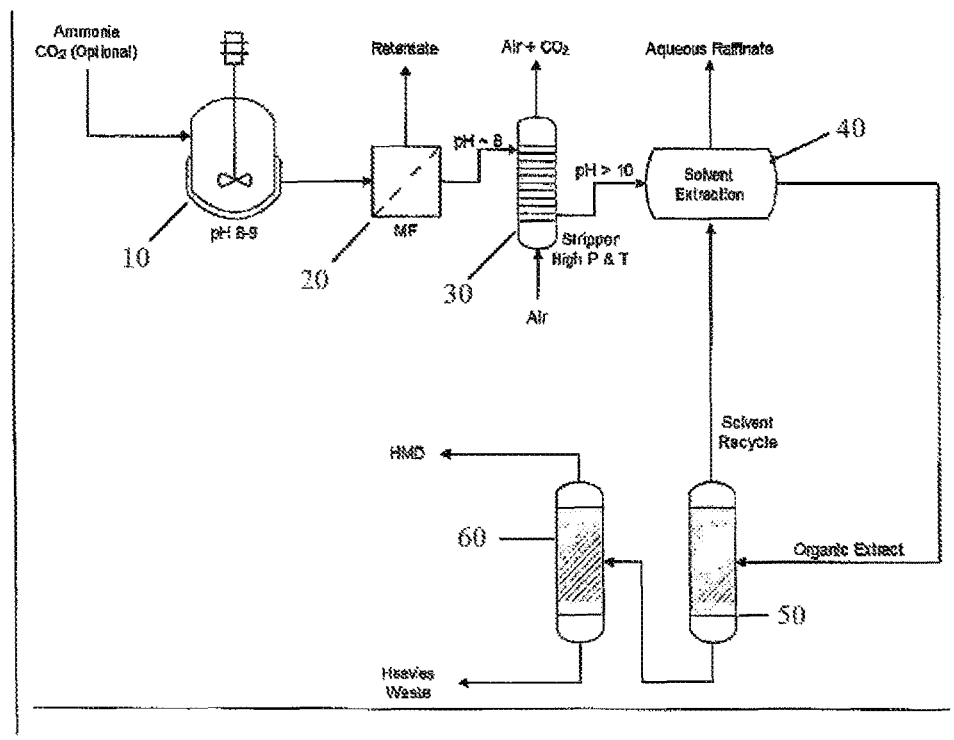
FIG. 3 is a schematic flow chart illustrating another embodiment of the invention of a fermentation process to prepare diamine.

FIG. 3 schematically illustrates an embodiment of a fermentation system that may be used to produce HMD. A genetically engineered microorganism is cultured or grown in reaction vessel 10 in a suitable culture or fermentation medium comprising a nitrogen source and a carbon source. In one embodiment of the invention, the typical culture or fermentation medium and growth conditions are set out below in Example 3. During the fermentation of the genetically engineered microorganism to produce the desired diamine (e.g. HMD), carbon dioxide is used to control the pH of the cultured medium. The carbon dioxide used may be produced metabolically by the microorganism, artificially or added from an external source. In an embodiment, the growth condition of the microorganism and the concentration of CO2 in the culture or fermentation medium are controlled so that the pH is maintained at a predetermined level during selected times during the fermentation cycle. Over the course of the fermentation process, the pH will rise from about neutral to a stable pH of 8.5 due to, for example, the buffer created by HMD and carbon dioxide. Upon completion of the fermentation or when HMD-Carbonates and/or Carbamates are produced, the cells may be removed (e.g. by membrane filtration 20) to separate the crude or impure aqueous solution containing charged HMD-Carbonate and/or Carbamate materials, such as HMD salts, from undesired by-products that will be contained in the retentate. After at least cell removal, the filtered, aqueous fermentation solution containing at least charged HMD-Carbonates and/or Carbamates materials can be stripped of carbon dioxide with inert gas or steam via steam stripping. Steam can be added from an external source, or generated "in situ" by boiling the broth under elevated temperature and pressure in reactor 30. Removal of CO2 will generate neutrally-charged or free base HMD in aqueous solution. By removing the carbon dioxide, the pH of the solution is raised to a point where solvent extraction can be used to remove HMD in its free base form. The neutral-charged or free base HMD may be extracted from the aqueous solution in extractor 40 which separates the organic components from the aqueous raffinate. The organic components containing at least solvent and HMD can be separated in distillation column and the distilled HMD can be further purified by distillation in distillation column 60. Recovered CO2 from reactor 30 and the recovered solvent from distillation column may be recycled in the described process to improve process and economic properties of the illustrated fermentation process.

Culturing a microorganism in medium under suitable conditions and for a sufficient period of time results in the formation of one or more diamine Carbonates and/or Carbamates. The produced compounds in the cultured medium include at least 40% Carbonates and/or Carbamates in the cultured medium. In other embodiments, the Carbonates and/or Carbamates can be at least 50%, 60%, 70%, 80, 90% or 99.9% in the cultured medium. As defined above, this means that desired diamine (e.g. HMD) carbonates or carbamates comprise at least 40% or more of all carbonates and/or carbamates in the cultured medium.

Culture Medium

Depending on the desired microorganism or strain to be used, the appropriate culture medium may be used. For example, descriptions of various culture media may be found in "Manual of Methods for General Bacteriology" of the American Society for Bacteriology (Washington D.C., USA, 1981). As used here, "medium" as it relates to the growth source refers to the starting medium be it in a solid or liquid form. "Cultured medium", on the other hand and as used here refers to medium (e.g. liquid medium) containing microbes that have been fermentatively grown and can include other cellular biomass. The medium generally includes one or more carbon sources, nitrogen sources, inorganic salts, vitamins and/or trace elements.

Exemplary carbon sources include sugar carbons such as sucrose, glucose, galactose, fructose, mannose, isomaltose, xylose, pannose, maltose, arabinose, cellobiose and 3-, 4-, or 5-oligomers thereof. Other carbon sources include alcohol carbon sources such as methanol, ethanol, glycerol, formate and fatty acids. Still other carbon sources include carbon sources from gas such as synthesis gas, waste gas, methane, CO, $CO_2$ and any mixture of CO, $CO_2$ with $H_2$. Other carbon sources can include renewal feedstocks and biomass. Exemplary renewal feedstocks include cellulosic biomass, hemicellulosic biomass and lignin feedstocks.

In some embodiments, culture conditions include anaerobic or substantially anaerobic growth or maintenance conditions. Exemplary anaerobic conditions have been described previously and are well known in the art. Exemplary anaerobic conditions for fermentation processes are disclosed, for example, in U.S. Patent Application Publication No 2009/0047719, filed Aug. 10, 2007. Any of these conditions can be employed with the microbial organisms as well as other anaerobic conditions well known in the art.

The culture conditions can include, for example, liquid culture procedures as well as fermentation and other large scale culture procedures. As described herein, particularly useful yields of the products can be obtained under anaerobic or substantially anaerobic culture conditions.

An exemplary growth condition for achieving, hexamethylenediamine includes anaerobic culture or fermentation conditions. In certain embodiments, the microbial organism can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an N2/CO2 mixture or other suitable non-oxygen gas or gases.

The culture conditions can be scaled up and grown continuously for manufacturing hexamethylenediamine. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of, hexamethylenediamine. Generally, and as with non-continuous culture procedures, the continuous and/or near-continuous production of hexamethylenediamine will include culturing a hexamethylenediamine producing organism on sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, the desired microorganism can be cultured for hours, if suitable for a particular application. It is to be understood that the continuous and/or near-continuous culture conditions also can include all time intervals in between these exemplary periods. It is further understood that the time of culturing the microbial organism is for a sufficient period of time to produce a sufficient amount of product for a desired purpose.

Fermentation procedures are well known in the art. Briefly, fermentation for the biosynthetic production of hexamethylenediamine can be utilized in, for example, fed-batch fermentation and batch separation; fed-batch fermentation and continuous separation, or continuous fermentation and continuous separation. Examples of batch and continuous fermentation procedures are well known in the art.

The culture medium at the start of fermentation may have a pH of about 5 to about 7. The pH may be less than 11, less than 10, less than 9, or less than 8. In other embodiments the pH may be at least 2, at least 3, at least 4, at least 5, at least 6, or at least 7. In other embodiments, the pH of the medium may be about 6 to about 9.5; 6 to about 9, about 6 to 8 or about 8 to 9.

CO2 Sources and Species

As noted above, to produce the desired diamine (e.g. HMD) and to control pH of the culture medium CO2 is added. The source of CO2 can take the form of CO2, carbonate, bicarbonate or carbonic acid, for example. In one embodiment, CO2 may be externally added to the cultured medium. In other embodiments, CO2 may be produced by the microorganism such as by respiration or as a by-product. For example, the respiration CO2 may be formed from the conversion of the tricarboxylic acid (TCA) cycle, via the glyoxylate shunt, the pentose phosphate pathway (e.g. gnd (6-phosphogluconate dehydrogenase that converts 6-phosphogluconate to ribuloase-5-phosphate and $CO_2$)) or the Entner Duodoroff pathways. In other embodiments, the by-product CO2 may be formed from acetate, ethanol, succinate, 3-oxoadipate or 3-hydroxyadipate.

Culturing the microorganism under suitable conditions and sufficient periods of time also results in the microorganism forming one or more CO2 sources that include 002, carbonate, bicarbonate or carbonic acids. In one embodiment, the microorganism forms CO2 stoichiometrically with the diamine.

Stoichiometric CO2 as referred here is the amount of CO2 associated with the formation of the product from a given substrate based on the stoichiometry. One exemplary stoichiometry for the production of HMD from glucose is:

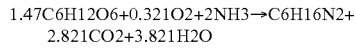

1.47$C_6H_{12}O_6$+0.32$1O_2$+2$NH_3$→$C_6H_{16}N_2$+ 2.821$CO_2$+3.821$H_2O$

The stoichiometric CO2 amount produced per mole of HMD is 2.821 moles. Any CO2 produced higher than this amount is either produced by respiration or byproduct formation.

Some sources of respiratory CO2 are the TCA cycle, glyoxylate shunt, pentose phosphate pathway (e.g. zwf) and the Entner-Duodoroff pathway among others. These pathways produce NAD(P)H that can then be used via the electron transport chain to form ATP. Byproduct CO2 is defined as the CO2 produced due to the formation of byproducts. For example, 2 moles of acetate are produced from every mole of glucose and this is associated with the release of 2 moles of CO2. Therefore, the byproduct CO2 associated with the formation of each mole of acetate is 1 mole.

In another example, the production of HMD from methanol can have multiple stoichiometries, depending upon whether only the oxidative TCA branch is used to make HMD, compared if both the oxidative and the reductive TCA branches are used to make HMD

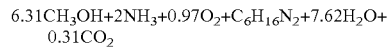

6.31$CH_3OH$+2$NH_3$+0.97$O_2$+$C_6H_{16}N_2$+7.62$H_2O$+ 0.31$CO_2$

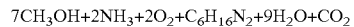

7$CH_3OH$+2$NH_3$+2$O_2$+$C_6H_{16}N_2$+9$H_2O$+$CO_2$

In the case where CO2 is used to drop the pH (e.g. to 7), the solubility of the medium towards CO2 may be enhanced by raising the back pressure at the top of the fermentor to at least 2, but not exceeding 10 bar to increase the solubility of carbon dioxide. In other embodiments, the temperature may be lowered to enhance solubility of the medium for 002. In one embodiment, the temperature is lowered below 37° C. to increase the solubility of 002.

In one embodiment, a microorganism producing the diamine is cultured in a liquid medium in a fermenter, wherein an inlet gas including carbon dioxide is fed into the fermenter and the back pressure at the top of the fermentor is raised to at least 2, but not exceeding 10 bar to increase the solubility of carbon dioxide.

In another embodiment, the process for the fermentative production of a diamine, wherein a microorganism producing the diamine is cultured in a liquid medium in a fermenter, wherein an inlet gas including carbon dioxide is fed into the fermenter and the temperature is lowered below 37° C. to increase the solubility of CO2.

In some embodiments, an enzyme carbonic anhydrase (CA) may be added to the fermentation broth or medium to catalyze or enhance the formation of diamine Carbonates and/or diamine Carbamates (e.g. HMDA Carbonates) by increasing the amount or rate of gaseous CO2 converted to soluble ion, thus a greater amount or availability of soluble ion is available to the diamine or HMD.

Carbonic anhydrase catalyzes a reversible reaction. In the forward reaction, CA combines carbon dioxide with water:

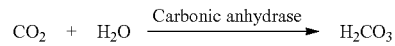

$$CO_2 + H_2O \xrightarrow{\text{Carbonic anhydrase}} H_2CO_3$$

and H2CO3 dissociates to form bicarbonate (HCO3-) and a proton. In the reverse, reaction, CA combines bicarbonate and a proton to provide carbon dioxide and water. Therefore, the reversible reaction, in particular the reverse reaction can be used to strip or release the CO2 after the DA carbonate is formed. In some embodiments, the CA may be used to hydrate CO2 in the form of bicarbonate and proton, which in turn may be converted to a DA. Depending on the direction of the reaction, certain suitable conditions can be selected that favor the absorption of carbon dioxide into a solution (e.g., via hydration of carbon dioxide to bicarbonate) and/or the desorption of carbon dioxide from a solution (e.g., via dehydration of bicarbonate to carbon dioxide and water).

The carbonic anhydrase may be provided exogenously by directly providing the CA to the fermentation solution or may be introduced via a microorganism capable of producing carbonic anhydrase. Carbonic anhydrase may also be provided as a recombinant or engineered CA. The recombinant CA may be part of a microorganism that includes a diamine pathway (e.g. HMD synthesis pathway) or may be introduced by another microorganism capable of CA expression. The microorganism's native CA may be used, for example by overexpressing it or engineering it to be excreted into the fermentation broth or solution or be secreted into the microorganism's periplasm. The CA may be of the EC 4.2.1.1. enzyme class. The CA may be that of an *Escherichia*, for example Can gene or b1026 (KEGG designation) or other host strain, including strains listed herein. In some embodiments the CA may be obtained from the genus *Methanobacterium, Desulfovirbio, Methanosarcina, Thiomicrospira, Acetobacterium, Clostridium, Methylobacterium, Rhizobium, Rhodobacter, Rhodospirillum, Staphylococcus, Methanococcus, Methanosaeta, Methanospirillum, Sulfolobus.* (Smith et al., 1999 PNAS 96(26):15184-15189.

Exemplary organisms from which the CA may be obtained include *Neisseria gonorrhoeae* (Jo et al., 2013 Appl. Environ. Microbiol. 79(21):6697-6705), *Methanosarcina, Thiomicrospira, Acetobacterium woodii, Clostridium thermoaceticum, Methylobacterium extorquens, Rhizobium meffloti, Rhodobacter capsulatus, Rhodobacter sphaeroides, Rhodospirillum rubrum, Staphylococcus aureus, Methanococcus jannaschii, Methanosaeta concilii, Methanosarcina barkeri, Methanosarcina thermophila, Methanospirillum hungateii, Sulfolobus solfataricus.* (Smith et al., 1999 PNAS 96(26):15184-15189. The CA may be obtained from *Neisseria gonorrhoeae* (Jo et al., 2013 Appl. Environ. Microbiol. 79(21):6697-6705). In some embodiments, a carbonic anhydrase of a *Neisseria gonorrhoeae* may be engineered for periplasmic expression in *E. coli* as reported Jo et al., 2013 Appl. Environ. Microbiol. 79(21): 6697-6705

In some embodiments, the gene encoding a β type CA may be obtained from the genus *Desulfovirbio* such as *Desulfovirbio fructosivorans, Desulfovirbio* Tom C, *Desulfovirbio magneticus, Desulfovirbio alcholivorans*. In still other embodiments, the CA may be obtained from the genus *Desulfomonile* such as *Desulfomonile tiedjei, Methanobacterum* such as *Methanobacterium thermoautotrophicum, Metanoacina* such as *Metanoacina thermophilia, Thiomicrospira* such as *Thiomicrospira crunogena.*

In other embodiments, the CA may be used as shown in Table A below:

TABLE A

| Sequence Identifiers | % Identity | Sequence |
|---|---|---|
| gi\|506426310\|ref\| WP_015946029.1\|;gi\| 218758438\|gb\| ACL09337. 1\| | 100.0 | [Desulfovibrio vulgaris str. 'Miyazaki F' MRLRFLSALFLVVAMVGTALAGS TGPGIGPDEALQRLKEGNARFVA ETPTRQNLSAKRLATSQHGQTPY ATILSCADSRAPVELIFDEGVGD LFVIRVAGNVAATDEVGTAEYGA DHLNVPLLVVMGHTQCGAVTAVV QGAEVHGSIPMLVAPIVPAVTAV EKSNPKHDRAALVPKVIEANVWQ AIDDTMRQSPIIRARVAAGKLKV VGAIYHIDDGKVEWLGEHPMQAR LLNYTSGPAKAHR |
| gi\|496399538\|ref\| WP_009108528.1\|;gi\| 385733492\|gb\| EIG53690.1\| | 55.1 | [Desulfovibrio sp. U5L] MKRFLAATATMAFLLAMCTAVLA SSGGPEVSADEALSRLKEGNTRF VSQANVAPHQDAARRHETATGGQ HPFATVLSCADSRAPVEVLFDQG VGDLFVVRVAGNVAATDEIGTIE YGAEHLGVPLVVVLAHTKCGAVT AVVKNEPVTENIGKLVAPIVPAV KGVKARFAASDVNEIISRSIEAN MWQAVSDIYAKSPMLKKMAADGK IKVVGALYDIDSGEVHWFGEHPS EGNLLDN |
| gi\|760112986\|ref\| WP_043794941.1\| | 59.9 | [Desulfovibrio fructosivorans] MKRAFAAFAAAVFVAATCALALA SSAGPGLTSDEALAKLKEGNDRY VAKASVAPRRDAARRHETATGGQ HPFATVLACSDSRVPVEVVFDQG VGDIFVVRVAGNVAATDEIGTME YGAEHLGVPLIVVMGHTKCGAVS AVVKNEPVTENIGKLVAPIVPAV KSVKARFATANTDELIAKSIEAN VWQAISDIYAKSPLIKKMAAAGK VKVVGALYDIDSGEVHWLGEHPN NAILLGK |
| gi\|302490589\|gb\| EFL50494.1\| | 59.9 | [Desulfovibrio fructosivorans JJ] MMKRAFAAFAAAVFVAATCALAL ASSAGPGLTSDEALAKLKEGNDR YVAKASVAPRRDAARRHETATGG QHPFATVLACSDSRVPVEVVFDQ GVGDIFVVRVAGNVAATDEIGTM EYGAEHLGVPLIVVMGHTKCGAV SAVVKNEPVTENIGKLVAPIVPA VKSVKARFATANTDELIAKSIEA NVWQAISDIYAKSPLIKKMAAAG KVKVVGALYDIDSGEVHWLGEHP NNAILLGK |

TABLE A-continued

| Sequence Identifiers | % Identity | Sequence |
|---|---|---|
| gi\|759946892\|ref\|WP_043631526.1\| | 58.4 | [Desulfovibrio sp. TomC] MRRNMTAMTVVIWTLCMATTALAFSGGAGITADEALSRLKEGNTRFVAGAAVTPRQDAARRHETTVGGQHPFATVLACADSRVPVEAIVDQGVGDVFVVRVAGNVANTDEIGTIEYGAEHLGVPLVVVLGHTKCGAVTAVVKGEHVTENIGKLVAPIVPAVAGVKNRFASADLDELINRSIEANVWQSISDMYANSPLLKKMAADGKLKVVGALYDIDSGDIHWLGEHPSNAKLLGN |
| gi\|732991830\|gb\|KHK04204.1\| | 58.3 | [Desulfovibrio sp. TomC] MTVVIWILCMATTALAFSGGAGITADEALSRLKEGNTRFVAGAAVTPRQDAARRHETTVGGQHPFATVLACADSRVPVEAIVDQGVGDVFVVRVAGNVANTDEIGTIEYGAEHLGVPLVVVLGHTKCGAVTAVVKGEHVTENIGKLVAPIVPAVAGVKNRFASADLDELINRSIEANVWQSISDMYANSPLLKKMAADGKLKVVGALYDIDSGDIHWLGEHPSNAKLLGN |
| gi\|493978453\|ref\|WP_006921438.1\|;gi\|409981683\|gb\|EKO38218.1\| | 55.7 | [Desulfovibrio magneticus] MKRFVTAFAGAVITISMAGAAMAFSGGAGISADEALARLKEGNTRYVAGAAVTPRQDAARRHETATGGQHPFVSVLSCADSRVPVETVFDQGIGDVFVIRVAGNVANTDEIGTIEYGAEHLGTPLVLVMAHTKCGAVTAVVKGEHVTENIGKLVAPIVPAVASVKSRFATDDVNELINRSIEANMWQAIADMYAKSPLLKKMAADGKIKVVGALYDIDSGEVHWFGEHPSNANLLGK |
| gi\|496471458\|ref\|WP_009180303.1\|;gi\|357581548\|gb\|EHJ46881.1\| | 54.7 | [Desulfovibrio sp. FW1012B] MKRFLAATATMAFLLAMCTAVLASSGGSEVSADEALSRLKEGNTRFVSQANVAPHQDAARRHETATGGQHPFATVLSCADSRAPVEVLFDQGVGDLFVVRVAGNVAATDEIGTIEYGAEHLGVPLVVVLAHTKCGAVTAVVKNEPVTENIGKLVAPIVPAVKGIKARFAASDVNEIISRSIEANMWQAISDIYAKSPMLKKMAADGKIKVVGALYDIDSGEVRWFGEHPSEGSLLDN |
| gi\|752616536\|ref\|WP_041285901.1\| | 53.8 | [Desulfomonile tiedjei] MEAFMKKIAVLFSVICMLGSVFSWAADPAATVSPEEAVKLLKEGNGRFIAGTSQHPNNDLQRRNTTAAQGQHPFVTVLSCSDSRVPVEVLFDRGVGDIFVIRVAGNVANGDEVGSIEYAVDHLGTPLLVILGHTKCGAVTAVVQSAELLGNIIPIGKSIFPAVVAAKKSNPKASGDALINDAIKANVWQAIEDIYRTSPITAARVKSGKLKVVGALYDIESGNVSWLGSHPKEGGLLSDKGH |
| gi\|390622030\|gb\|AFM23237.1\| | 53.8 | [Desulfomonile tiedjei DSM 6799] MKKIAVLFSVICMLGSVFSWAADPAATVSPEEAVKLLKEGNGRFIAGTSQHPNNDLQRRNTTAAQGQHPFVTVLSCSDSRVPVEVLFDRGVGDIFVIRVAGNVANGDEVGSIEYAVDHLGTPLLVILGHTKCGAVTAVVQSAELLGNIIPIGKSIFPAVVA |

TABLE A-continued

| Sequence Identifiers | % Identity | Sequence |
|---|---|---|
| | | AKKSNPKASGDALINDAIKANVW QAIEDIYRTSPITAARVKSGKLK VVGALYDIESGNVSWLGSHPKEG GLLSDKGH |
| gi\|657653962\|ref\| WP_029458402.1\| | 58.8 | [*Desulfovibrio alcoholivorans*] MKRLFTATTMLALLLACCALALA SSGGPGLTADEALAKLKEGNMRY VAQASVAPHQDAARRHETATDGQ HPFATILSCADSRVPLEIIFDQG VGDIFAVRVAGNVAAVDEIGTME YGAEHLGVPLIVVLGHTKCGAVT AVVKNEPVTENIGQLVAPIVPAV KSVKSRFASASLDELINKSIEAN VWQAVSDIYAKSPLLKKMAAAGK VKVVGALYDIDSGKVQWFGEHPS NASLLGK |
| gi\|506341077\|ref\| WP_015860796.1\|;gi\| 239796622\|dbj\| BAH75611.1 | 54.9 | [*Desulfovibrio magneticus*] MKRFVAAFAGAVITFSMAGAAMA FSGGAGISADEALARLKEGNTRY VAGAAVTPRQDAARRHETATGGQ HPFVSVLSCADSRVPVETVFDQG IGDVFVIRVAGNVANTDEIGTIE YGTEHLGTPLVVVLAHTKCGAVT AVVKGEHVTENIGKLVAPIVPAV ASVKSRFASGDLNELINRSIEAN MWQAIADMYAKSPLLKKMAADGK IKVVGALYDIDSGDVHWFGEHPS NANLIGK |
| *Escherichia coli* str. K-12 substr, MG1655]yadF | | *Escherichia coli* str. K-12 substr, (MG1655]MKDIDTLISNNALWS KMLVEEDPGFFEKLAQAQKPRFL WIGCSDSRVPAERLTGLEPGELF VHRNVANLVIHTDLNCLSVVQYA VDVLEVEHIIICGHYGCGGVQAA VENPELGLINNWLLHIRDIWFKH SSLLGEMPQERRLDTLCELNVME QVYNLGHSTIMQSAWKRGQKVTI HGWAYGIHDGLLRDLDVTATNRE TLEQRYRHGISNLKLKHANHK |
| >b0339; NP_414873.1; GI:16128324] CynT | | *Escherichia coli* MKEIIDGFLK FQREAFPKRE ALFKQLATQQ SPRTLFISCS DSRLVPELVT QREPGDLFVI RNAGNIVPSY GPEPGGVSAS VEYAVAALRV SDIVICGHSN CGAMTAIASC QCMDHMPAVS HWLRYADSAR VVNEARPHSD LPSKAAAMVR ENVIAQLANL QTHPSVRLAL EEGRIALHGW VYDIESGSIA AFDGATRQFV PLAANPRVCA IPLRQPTAA |
| GI:157878699 | | *Neisseria gonorrhoeae* HTHWGYTGHD SPESWGNLSE EFRLCSTGKN QSPVNITETV SGKLPAIKVN YKPSMVDVEN NGHTIQVNYP EGGNTLTVNG RTYTLKQFHF HVPSENQIKG RTFPMEAHFV HLDENKQPLV LAVLYEAGKT NGRLSSIWNV MPMTAGKVKL NQPFDASTLL PKRLKYYRFA GSLTTPPCTE GVSWLVLKTY DHIDQAQAEK FTRAVGSENN RPVQPLNARV VIE |

The CA may be encoded by *Desulfovibrio vulgaris*. *Desulfovibrio vulgaris* which has unique properties of having high activity in 4.2 M N-methyldiethanolamine (MDEA) at elevated temperatures and pH >10. The *D. vulgaris* CA has been evolved to be active at 100° C. for long periods of time (8 weeks) in high concentrations of MDEA for use in carbon capture technology (Alvizo, et. al. 2014 PNAS 111(46): 16436-16441). In some embodiments, the engineered CA is from *Desulfovibrio vulgaris* (GenBank accession ACL09337.1 GI:218758438). In some embodiments, the *Desulfovibrio vulgaris* str "Miyazaki F" carbonic anhydrase has amino acid substitution to stabilize the carbonic anhydrase activity at elevated temperatures and alkaline pH by including one or more substitutions identified as: A56S, T3OR, A40L, A84Q, G120R, T139M, K37R, E68AQ, A95V, Q119M, N145WFC, N213E, A219T, R31P, Q43M, V70I, H124T, H148T, V157A, M170F, H44L, M129F, S144R, Y49F, S126N, D196S, P136R, P174E, D195A, G89A, D96E, V100T, A121Q, A181K, M207A, S216D.

In some embodiments, a CA is encoded by *E. coli* (EG10176 (EcoCyc), or EG12319 (EcoCyc), Can gene, b1026 (KEGG designation)).

The disclosed enzymes may also be in the form of fusion proteins in which the recombinant or engineered CA are fused to antibody tags (e.g. myc epitope), purification sequences (e.g. His tags for binding to metals and cell localization signals (e.g. secretion or excretion signal). To aid in the expression of the desired protein into periplasmic space, a secretion signal may be use such as a Sec tag or Tat tag. In preferred embodiments the CA is excreted into the media rather than secreted to the periplasmic space. In some embodiments, the secretion or excretion signal is fused to the N-terminus of the protein by genetically encoding the secretion tag as a fusion to the carbonic anhydrase DNA sequence to aid expression into the periplasmic space or extracellularly excreted from the microorganism (e.g. *E coli*). In another embodiment, CA may be fused to an *E. coli* protein OmpF that is transported (excreted) to the culture medium (Nagahari et al., 1985 The EMBO J. 4(13A):3589-3592; Jeong and Lee, 2002 Appl. Environ. Microbiol. 68:4979-4985). In still another embodiment CA may be fused to the *E. coli* protein YebF which as been shown to support protein export to the culture medium, which has an unknown function, but is an extracellular protein (Zhang et al., 2006 Nat. Biotech. 24:100-10). An N-terminal secretion signal peptide tag is identified using SignalP 4.1 Server (http://www.cbs.dtu.dk/services/SignalP/).

The carbonic anhydrase may be provided by a genetically engineered microorganism in the fermentation broth. In other embodiments, the carbonic anhydrase is provided by a genetically engineered microorganism that produces the DA, optionally excreted to the broth, and optionally present in the microorgansim's periplasm. In other embodiments, the carbonic anhydrase is a native gene or enzyme, optionally engineered for secretion to the broth, and optionally engineered for secretion to the microorganism's periplasmic space.

In some embodiments, the CA may be excreted into the fermentation broth, and in other embodiments, the CA may be present in the microorgansim's periplasm.

Depending on the direction of the reaction or the speed of the reaction, in some embodiments the native CA gene (e.g. *E. coli* coded CA) sequence may be overexpressed, for example by modifying its promoter, and or engineered with a secretion or excretion peptide or fusion.

In some embodiments, variants of the CA that are capable of carrying out the forward and/or reverse reactions are contemplated. The variant can be a homolog, ortholog, paralogs or genetically engineered, for example increased alkaline pH and heat stability.

CA having an improved property (e.g., thermal stability, solvent stability, and/or base stability) that allows them to enhance the forward and/or reverse reaction may be selected for and used. In some embodiments, CA variants that are active and/or stable at high concentration of DA (e.g. HMD) may be selected for and used. In other embodiments, CA and variants thereof that are active and/or stable at high concentrations of C2 to C7 methylene segments such as hexamethylenediamine (HMD), cadaverine, putrescine, ethylenediamine and heptamethylenediamine may selected and used.

Depending on the conditions selected, the CA may be a thermostable CA or may be a alkaline pH stable CA, or both. Preferably the alkaline pH is about pH 8-13. In some embodiments, the pH may range from pH 8-13, pH 8.5 to 13, pH 9-13, pH 10-13, pH 8-12, pH 8.5-12, pH 9-12, pH 8-11, pH 8.5-11, pH 9-11, pH 10-11 and pH 10-12. Temperature and basic pH stability can be useful if the CA is used in the step or steps for release of $CO_2$ from the DA Carbonate or Carbamate. This step can result in increase in pH as $CO_2$ is released and free base formed. Additionally in some embodiments temperatures above room temperature and above typical fermentation temperatures may be used to facilitate release of $CO_2$.

Depending on whether the forward reaction or the reverse reaction is favored, the fermentation broth may be provided with CA enzymes that have different activity. In some embodiments, the CA may have optimal activity for the forward reaction and in other embodiments the CA enzyme may have optimal activity for the reverse reaction. In some embodiments, a mixture of different enzymes having varying optimal activities and/or improved properties as disclosed herein may be used.

In some embodiments, the method can be carried out wherein the carbonic anhydrase has the improved property at least 1.2-fold, at least 1.3-fold, at least 1.5-fold, at least 2-fold, at least 3-fold, at least 4-fold, at least 5-fold, at least 10-fold, or at least 25-fold increased activity of hydrating carbon dioxide or dehydrating bicarbonate under suitable conditions. Accordingly, in some embodiments, the suitable conditions used in the method can comprise a concentration of the carbonic anhydrase polypeptide of from about 0.1 g/L to about 10 g/L, about 0.25 g/L to about 7.5 g/L, about 0.5 g/L to about 5 g/L, less than 10 g/L, less than about 5 g/L, or less than about 2.5 g/L.

In some embodiments, the CA may be provided exogenously. In other embodiments, the CA enzyme may be provided directly into the broth or fermentation solution. In some embodiments, the CA is provided by a genetically engineered microorganism in the fermentation broth or solution, where the CA can be excreted into the broth or may be present in the microorganism's periplasm. In other embodiments, the enzyme may be provided immobilized on particles. Recombinant carbonic anhydrase polypeptide may be immobilized on a surface, for example wherein the enzyme is linked to the surface of a solid-phase particle in the solution. Methods for linking (covalently or non-covalently) enzymes to solid-phase particles (e.g., porous or non-porous beads, or solid supports) such that they retain activity for use in bioreactors are well-known in the art. Methods for treating a gas stream using immobilized enzymes are described in e.g., U.S. Pat. No. 6,143,556, U.S. patent publication no. 2007/0004023 A1, and PCT publications WO98/55210A1, WO2004/056455A1, and WO2004/028667A1, each of which is hereby incorporated by reference herein.

Accordingly, in some embodiments, the methods for enhancing the release of $CO_2$ from a solution of DA Carbonates or DA Carbamates can be carried out where the engineered carbonic anhydrase polypeptide is immobilized on a surface, for example where the enzyme is linked to the surface of a solid-phase particle (e.g., beads). In some embodiments, the methods using immobilized polypeptides can be carried out where the method further includes a step of isolating or separating the immobilized carbonic anhydrase from the broth or fermentation solution. After separating the immobilized carbonic anhydrase from the broth or fermentation solution, the broth or fermentation solution can be treated to conditions that may inactivate the enzyme, e.g., desorption of $CO_2$ at high temperatures. Further, the separately retained immobilized enzyme can be added to another solution and reused. $CO_2$:DA Ratios Under the disclosed process, the microorganism (e.g. genetically engineered microorganism) forms $CO_2$ and DA (e.g. HMD) in the ratio of about 0.05 to 1 to about 5 to 1 to about 7:1. Other suitable ratios include 0.2 to 1 to about 3 to 1. In other embodiments, the ratio of $CO_2$ to DA (e.g. HMD) include about 0.05 to 1 to about 3 to 1; about 0.05 to 1 to about 2.5 to 1; about 0.05 to 1 to about 2 to 1; about 0.05 to 1 to about 1.5 to 1; about 0.05 to 1 to about 1 to 1.

The disclosed ratios may be determined by measuring the $CO_2$ in the form of the total dissolved inorganic carbon (DIC) in the cultured medium. The DIC, which include the Carbonates and/or Carbamates may be measured, for example by the "Handbook of Methods for the Analysis of the Various Parameters of the Carbon Dioxide System in Sea Water." Prepared for the U.S. Department of Energy, Special Research Grant Program 89-7A: Global survey of carbon dioxide in the oceans. Version 2—September 1994 Edited by Andrew G. Dickson & Catherine Goyet (referred to as the Handbook). For example, the DIC may be measured by the "SOP 2: Determination of total dissolved inorganic carbon in sea water, p. 1-18" on pages 38-55 of the Handbook.

In other embodiments, the fraction of DIC, which is DIC over Total Dissolved Counter Anions (TDCA) may be measured. The TDCA is the sum of DIC and other anions. The other anions (e.g., $Cl^-$, $SO^{-2}$, $PO_4^{-3}$, $NO_3^-$, $NO_2^-$) other than the DIC can be determined using any suitable method such as ion exchange chromatography. For example, a commercially available ion exchange chromatography by DIONEX with conductivity detector (and ion suppressor) may be used.

The produced compounds in the cultured medium include have a DIC/TDCA value of at least 40%. In other embodiments, the DIC percentage can be at least 50%, 60%, 70%, 80, 90% or 99.9% in the cultured medium. In some embodiments, the DIC is at least 40%, 50%, 60%, 70%, 80, 90% or 99.9% of TDCA in the cultured medium at pH 9.

Fermentation pH

As noted above, the starting culture medium may have a pH of about 5 to about 7. As the microorganism grows on the culture medium and produces the desired diamine (e.g. HMD-Carbonates and/or HMD Carbamates) and before the diamine Carbonates and/or Carbamates are converted to the diamine free base, the pH of the cultured medium may be less than 11, less than 10, less than 9, or less than 8. In other embodiments the pH may be at least 2, at least 3, at least 4, at least 5, at least 6, or at least 7. In other embodiments, the pH of the medium may be about 6 to about 9.5; about 6 to about 9, about 6 to about 8, about 6.5 to about 7.5, about 7.5 to about 9.5 or about 8 to about 9.

While the medium (i.e. the starting medium) may be adjusted with inorganic acids, bases or buffers to adjust pH, the cultured medium is substantially free of buffer, substantially free of inorganic or organic acid, or externally added inorganic or organic acid. As used here, "substantially free" relates to the cultured medium. In other words, salts, buffers, acids (not including $CO_2$) or bases may be used to control pH of the starting medium. If such salts, buffers, acids (not including $CO_2$) or bases are used to adjust pH fluctuations as fermentation and growth of the organism progresses, minimal amounts are used. But the salts, buffers, acids (not including $CO_2$) or bases are not used to neutralize the diamine Carbonate and/or Carbamate. It should be understood the microorganism will produce by-products such as acetates, succinates, other salts and/or organic acids. Adjusting pH during fermentation is by the use of carbon dioxide that may be added externally or generated by the microorganism's growth.

Release of $CO_2$ & Diamine Free Base

Once the diamine-Carbonates and/or Carbamates are formed, the diamine is obtained by converting to diamine free base, e.g. HMD free base. In some embodiments, the DA-Carbonates and/or Carbamates are first separated from the microorganism in the cultured medium before converting to DA free base. Examples of converting DA-Carbonates and/or Carbamates to DA free base include by heat, vacuum, ion exchange or electrodialysis. In one embodiment, the diamine is an HMD free base that may be converted by releasing carbon dioxide. In some embodiments, a carbonic anhydrase enzyme (as described more fully above in the context of the forward reaction) may be provided to enhance the release of carbon dioxide from a solution of DA Carbonates or DA Carbamates by converting a bicarbonate and/or carbonate ions to carbon dioxide. In such embodiments, the enzymes may be provided exogenously, for example, as an engineered enzyme that may be part of a microorganism or exogenously added. In some embodiments, the engineered CA may be engineered to be excreted into the fermentation broth or fermentation solution. In other embodiments, the engineered CA may be engineered to be in the microorganism's periplasm. In some embodiments, the DA-Carbonates and/or Carbamates are first separated from the microorganism in the cultured medium before converting to DA free base. In such embodiments, the CA may be provided by exogenously adding the CA. In other embodiments, the CA may be immobilized. In other embodiments, the CA is part of an engineered microorganism capable of providing carbonic anhydrase activity. In other embodiments, the carbonic anhydrase activity is provided by an engineered microorganism that includes a DA synthesis pathway such as a HMD synthesis pathway and the carbonic anhydrase activity.

If heat is used to convert diamine Carbonates and/or Carbamates (e.g. HMD) to diamine free base, the temperatures include greater than 70° C., greater than 80° C. or greater than 105° C. In some embodiments, the temperature may be greater than 200° C. In still other embodiments, the temperature may be about 315° C. In some embodiments, the temperature is less than 315° C., less than 250° C. or less than 215° C. In still other embodiments, the temperature may be greater than 20° C., greater than 30° C., or greater than 40° C. and where a vacuum is used. In some embodiments, the diamine Carbonates and/or Carbamates converted to free base at temperatures disclosed above may be HMD. CA may also be added to the heating step to enhance the release of carbon dioxide from a solution of DA Carbonates or DA Carbamates by converting a bicarbonate and/or carbonate ions to carbon dioxide and free base. Accordingly, in some embodiments, CA having an improved property (e.g., thermal stability, solvent stability, improved stability or activity in high concentrations of DA and/or base stability) that favors the reverse reaction is provided. Thus, in some embodiments the method of carbonic anhydrase catalyzed reverse reaction may be carried out at a temperature greater than 70° C., greater than 80° C. or greater than 105° C. In some embodiments, the temperature may be greater than 200° C. In still other embodiments, the temperature may be about 315° C. In some embodiments, the temperature is less than 315° C., less than 250° C. or less than 215° C. In still other embodiments, the temperature may be greater than 20° C., greater than 30° C., or greater than 40° C. and where a vacuum is used, greater than 70° C., greater than 80° C. or greater than 105° C. In some embodiments, the temperature may be greater than 200° C. In still other embodiments, the temperature may be about 315° C. In some embodiments, the temperature is less than 315° C., less than 250° C. or less than 215° C. In still other embodiments, the temperature may be greater than 20° C., greater than 30° C., or greater than 40° C. and where a vacuum is used.

Conversion may also be carried out in a vacuum such as lower than atmospheric pressure (e.g. 0.01 to 1 atm). In other embodiments, the pressure may include pressure of about 1 to about 10 bar (within the vessel, not the inlet air pressure) or about 1 to about 3 bar. When temperature and pressure are used in combination, the pressure may be from about 1 to about 3 bar. In some embodiments, the temperature is less than 315, less than 250 or less than 215.

The released CO2 may be recycled back into the system (e.g. into the cultured medium).

Other examples of converting diamine-Carbonates and/or Carbamates (e.g. HMD) to diamine free base (e.g. HMD free base) include sparging with gas (e.g. air, or inert gas such as nitrogen or helium) or steam stripping. The steam can be added from an external source, or generated in situ by boiling the broth. In some embodiments converting diamine (e.g. HMD) Carbonates and/or Carbamates to free base include by heat and sparging with gas. In one embodiment, stripping may be carried out at a pressure of about 1 to about 10 bar. In some embodiments, the converting step can result in about at least 20% to about at least 99% diamine free base. In other embodiments, the converting step can result in about at least about 20-30%, 30-40%, or 40-50%.

When sufficient heat is added to generate steam from the medium in situ in a stripping column, both water and carbon dioxide can be removed in sufficient amounts to obtain a solution concentrated in diamine (e.g. HMD) free base that allows efficient subsequent diamine recovery. In some embodiments, CA is also added to enhance the release of carbon dioxide from a solution of DA Carbonates or DA Carbamates by converting a bicarbonate and/or carbonate ions to carbon dioxide. Increasing the efficiency of CO2 removal from the DA Carbonate salt solution (e.g. HMD-bicarbonate salt solution) can lower purification costs by reducing the size of the stripping column.

In some embodiments, the diamine recovered as diamine free base can be greater than 40% or greater than 50%. In still other embodiments, the diamine recovered can be greater than 50% in free base form from the stripping step under ambient pressure, air sparge, and high temperature (e.g. less than 315° C., less than 215° C., or around 115° C.).

The addition of strong base (e.g. sodium or calcium hydroxide) may be added to raise the pH after diamine (e.g. HMD) free base is generated and CO2 is removed, thereby improving the extraction. If calcium hydroxide is used, a carbonate precipitate will form, which can then be separated from the liquid phase.

Solids Removal Prior to Conversion

Before converting the diamine (e.g. HMO) Carbonates and/or Carbamates to the diamine free base, solids can be separated from the cultured medium. Such solids may include cells and other biomass by products and impurities from the cultured medium. The resultant liquid fraction may be enriched in the diamine (e.g. HMD) Carbonates and/or Carbamates.

Separation may be achieved by centrifugation, filtration, rotary drum or combinations thereof. Exemplary centrifugation may be by a disc-stack centrifuge or decanter or solid bowl centrifuge. It should be understood that any combination of centrifugation types or configurations and number of centrifugations may be used to achieve the desired solids separation from the culture medium. If solids are not separable by centrifugation or additional separation is required, separation by filtration may be used. Filtration may be achieved by ultrafiltration.

Water Reduction or Removal

In some embodiments, water may be removed or reduced after the solids removal and prior to conversion. Any known suitable process for water removal or reduction may be used such as for example, evaporation, reverse osmosis, or electrodialysis.

In other embodiments, water may be removed prior to the step of isolating the diamine free base. One benefit of removing water before the isolation step can be an increase in pH. Methods to reduce or remove water as disclosed above in connection with water reduction or removal after solids removal and prior to conversion can also be used. The amount of water removal (e.g. upper limit of water removal) can depend on the solubility limit of a medium component or byproduct or the diamine salt or carbamate. In one embodiment, the water removal is dependent on whether it prevents insolubility of a medium component or byproduct, including the diamine salt or carbamate Evaporation may be carried out with multiple effects evaporator, thermal vapor recompression or mechanical vapor recompression. An evaporator is a heat exchanger in which a liquid is boiled to give a vapor that is also a low pressure steam generator. This steam can be used for further heating in another evaporator called another "effect." Thus, for example, two evaporators can be connected so that the vapor line from one is connected to the steam chest of the other providing a two, or double-effect evaporator. This configuration can be propagated to a third evaporator to create a triple-effect evaporator, for example.

Figure 4:
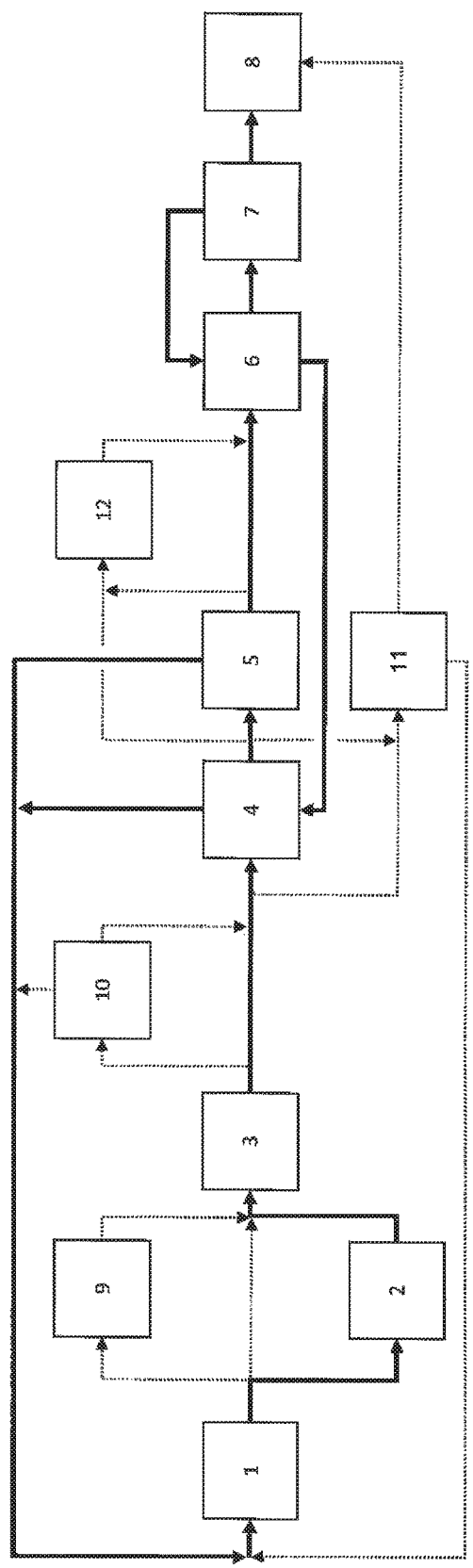
FIG. 4 is a block diagram of steps in an embodiment for preparing and processing a diamine. The numbers in each box are as follows.

In one embodiment, the amount of water removed is 10 wt percent. The removed water can be further recovered and recycled such as in the culturing process of step a) or as shown in FIG. 4.

Simultaneous Removal of Water and Carbon Dioxide

Water removal or reduction allows for a smaller solvent extraction column and less solvent, and the removal of carbon dioxide enables alkalization of the diamine composition (e.g. filtration permeate) to increase solvent extraction efficiency. In one embodiment described above, an evaporator is employed to remove sufficient water (and also enables removal of CO2) followed by a stripping column to remove any residual carbon dioxide (and can also remove water). Simultaneous removal of water and carbon dioxide in a single step to a point sufficient for subsequent extraction has the benefit of reducing costs and downtime associated with multiple steps. Accordingly, in another embodiment described above, a single step or unit operation is used to remove sufficient water and carbon dioxide (e.g. DIC) to enhance downstream diamine recovery, such as by solvent extraction. Accordingly, a step or unit operation (e.g. water evaporator or stripping column) and its associated costs of equipment, maintenance, use and risk of downtime may be absent or reduced. In one embodiment, the simultaneous water and carbon dioxide removal enhances the downstream recovery of HMD.

Water removal will also enable carbon dioxide stripping. Conditions for water removal can allow sufficient carbon dioxide removal obviating a need for a separate CO2 removal step. Thus in one embodiment the simultaneous removal of water and CO2 is effectively achieved by either a stripping unit or an evaporator unit. For example, an evaporator, e.g. a multi-effect evaporator, a mechanical vapor recompressor, can be used to remove sufficient water and carbon dioxide to obtain a solution concentrated in diamine free base that allows efficient subsequent diamine recovery. For example, in FIG. 4, step 4 or 5 can be absent when the retained step achieves sufficient removal of both water and carbon dioxide. As demonstrated in the Examples, use of an evaporator step can be advantageous compared to a stream stripping step.

It should be understood that the carbonic anhydrase may be present in a step or steps for releasing carbon dioxide and generating free DA base to enhance the release of carbon dioxide from a solution of DA Carbonates or DA Carbamates. In some embodiments, the CA may be present in the water removal or evaporation step, in other embodiments, the CA may be present in the CO2 stripping step, and in still other embodiments, the CA may be present in both the water removal or evaporation step and the CO2 stripping step.

Isolation of Diamine Free Base

Once converted, the DA (e.g. HMD) free base may be isolated from the cultured medium by extraction with an organic solvent. The isolated DA is separated from the organic solvent by a process such as distillation. Exemplary extraction solvents include alcohols, amines, ethers, alkanes and ketones. Exemplary extraction alcohols include C4 to C8 monohydric alcohols. In some embodiments, the extraction alcohols include hexanol, particularly 1-hexanol, isopentanol, or cyclohexanol, toluene or ethyl ether or mixtures thereof. Alkanes are suitable solvents as demonstrated in the Examples, particularly when HMD is the diamine. Alkanes, specifically hexane, may be used because of their extremely low water solubility. Hexane extracted little if any water and provided reasonable recovery of the available free base. Alkanes are therefore suitable solvents for use in recovery of diamine free base (e.g. HMD). Suitable alkanes include C5-C12, linear or branched. In one embodiment, both the diamine to be extracted and the alkane selected as solvent may have the same number of carbon atoms. Heptane is another suitable alkane, especially for HMD, which is further supported by the in silico modeling study below. Isomers of hexane and heptane are suitable. Hexane isomers are 2-methylpentane, 3-methylpentane, 2,2-dimethylbutane, and 2,3-dimethylbutane. Heptane isomers are 2-methylhexane, 3-methylhexane, 2,2-dimethylpentane, 2,3-dimethylpentane, 2,4-dimethylpentane, 3,3-dimethylpentane, 3-ethylpentane and 2,2,3-trimethylbutane. In some embodiments, the DA (e.g. HMD) free based can be directly distilled from the cultured medium.

Any suitable solvent may be used. In some embodiments, the solvent can have boiling points higher than HMD free base or desired diamine free base, lower than water or any boiling point in between HMD free base (or desired diamine free base) and water (an intermediate boiling point).

The DA (e.g. HMD) free base can be isolated from the medium or a DA-enriched fraction (e.g. when solids and/or water is removed before isolating) using an extraction solvent to provide an aqueous phase and a DA-free-base-containing organic phase.

The organic phase (extract) can include at least 10%, at least 20%, at least 30%, at least 40%, or at least 50% by weight DA (e.g. HMD) in free base, Carbonate, and/or Carbamate form, but predominantly in free base form. Depending on the number of extractions, in some embodiments, the DA (e.g. HMD) in the extract can be greater than 90% by weight.

The amount of DA free base that is extracted is about greater than 90% by weight. In some embodiments, the DA free base is HMD free base that is greater than 90% by weight.

The efficiency of solvent extraction of diamine, e.g. HMD, free base increases with decrease in carbon dioxide concentration such as DIC as shown in the Examples. A decrease in carbon dioxide results in higher pH and higher concentration of recoverable free base form. In some embodiments, the aqueous diamine solution prior to solvent extraction contains no detectable carbon dioxide, less than 0.01% carbon dioxide, less than 0.1%, 0.2%, 0.3%, 0.4%, 0.5% or 1% or less than 5% carbon dioxide. In some embodiments, the aqueous diamine solution prior to solvent extraction contains no detectable DIC, less than 0.01% DIC, less than 0.1%, 0.2%, 0.3%, 0.4%, 0.5% or 1% or less than 5% DIC. In other embodiments, the aqueous DA solution prior to solvent extraction contains no detectable DIC, less than 0.01% DIC, less than 0.1%, 0.2%, 0.3%, 0.4%, 0.5% or 1% or less than 5% DIC.

In one embodiment, CO2 produced stoichiometrically with DA, e.g. HMD, by an enzymatic pathway is used to neutralize DA, e.g. HMD, to maintain pH suitable for fermentation, generally a pH about 9 or lower. If desired or needed, further pH control can be achieved by supplementing with CO2 produced by the microbe as a by-product (e.g. shunt pyruvate to formate to CO2) or with an external source of CO2. The external CO2 can be purchased or can be CO2 recycled from the fermentation/isolation process. Due to the presence of CO2 during fermentation HMD carbonate, HMD bis-bicarbonate, HMD bicarbonate and a small amount of HMD carbamate and HMD biscarbamate are formed. At the end of fermentation, cells are optionally removed, and the culture medium is treated under pressure to degrade the HMD carbonate or carbamate compounds (or DA carbonate or carbamate compounds) releasing, for example, gaseous CO2 and creating free base HMD (neutral form 2HN—(CH2)6-NH2) (or DA free base) that increases the pH of the cultured medium. The free base or neutral HMD (or DA) may be isolated via solvent extraction. During the process, the released CO2 may be recycled. In one embodiment, the disclosed process does not require the use of acids to control pH and subsequent addition of base to neutralize the acids to generate solvent extractable free base HMD (or DA).

In another embodiment of the process, the culture or cultured medium is thermally treated by heating to reflux temperature, for example either batch wise or continually, for example to 90-110° C. at atmospheric pressure, or to a higher temperature at overpressure.

In another embodiment of the process, DA (e.g. HMD) is extracted with an organic solvent having a miscibility gap with water and stable at alkaline pH, such as in particular a polar, more specifically dipolar protic, organic solvent. Suitable solvents are as disclosed above.

In one embodiment, DA (e.g. HMD) extraction is and/or subsequent phase separation is carried out batchwise at elevated temperature.

The cultured medium, before or after removing the microbial organisms may be thickened or concentrated by known methods, such as, for example, with the aid of a rotary evaporator, thin-film evaporator, falling film evaporator, by reverse osmosis or by nanofiltration. If necessary, salts which may have precipitated due to the concentration procedure may be removed, for example by filtration or centrifugation. This concentrated cultured medium can then be worked up in the manner as disclosed herein to obtain DA (e.g. HMD). For the work up in accordance with the disclosed process, such a concentration procedure is feasible, but not absolutely necessary.

According to an embodiment, DA (e.g. HMD) is extracted from the cultured medium with the aid of an organic solvent. The organic solvent may have, for example, a miscibility gap with water and stable at alkaline pH, such as in particular a polar, dipolar protic, organic solvent. Suitable solvents are in particular cyclic or open-chain, optionally branched alkanols having from 3 to 8 carbon atoms, in particular n- and iso-propanol, n-, sec- and iso-butanol, or cyclohexanol, and also n-pentanol, n-hexanol-n-heptanol, n-octanol, 2-octanol and the mono- or polybranched isomeric forms thereof.

In one embodiment, the extraction and/or subsequent phase separation are carried out batchwise at an elevated temperature which is limited by the boiling points of water and of the extractant or of possibly forming azeotropes. Using for example, the extractant n-butanol extraction and phase separation could be carried out, for example, at about 25-90° C. or, preferably, at 40-70° C. For extraction, the two phases are stirred until the partition equilibrium has been established, for example over a period of from 10 seconds to 2 hours, or 5 to 15 min. The phases are then left to settle until they have separated completely; this takes for example, from 10 seconds to 5 hours, for example 15 to 120 or 30 to 90 minutes, in particular also at a temperature in the range from about 25-90° C. or 40-70° C. in the case of n-butanol.

In further embodiments, DA (e.g. HMD) is extracted from the cultured medium continuously in a multi-stage process (for example in mixer-settler combinations) or continuously in an extraction column.

One of skill in the art may establish the configuration of the extraction columns which can be employed according to the disclosed process for the phases to be separated in each case as part of optimization routines. Suitable extraction columns are in principle those without power input or those with power input, for example pulsed columns or columns with rotating internals. The skilled worker may also, as part of routine work, select in a suitable manner types and materials of internals, such as sieve trays, and column trays, to optimize phase separation. The basic theories of liquid-liquid extraction of small molecules are well known (cf. e.g. H.-J. Rehm and G. Reed, Eds., (1993), Biotechology, Volume 3 Bioprocessing, Chapter 21, VCH, Weinheim). The configuration of industrially applicable extraction columns is described, for example, in Lo et al., Eds., (1983) Handbook of Solvent Extraction, John Wiley & Sons, New York. Explicit reference is made to the disclosure of the textbooks above.

After phase separation, DA (e.g. HMD) is isolated and purified from the DA-containing extract phase in a manner known per se. Possible measures of recovering DA (e.g. HMD) are in particular, without being limited thereto, distillation, precipitation as salt with suitable organic or inorganic acids, or combinations of such suitable measures.

Distillation

Distillation may be carried out continuously or batchwise. A single distillation column or a plurality of distillation columns coupled to one another may be used. Configuring the distillation column apparatus and establishing the operational parameters are the responsibilities of the skilled worker. The distillation columns used in each case may be designed in a manner known per se (see e.g. Sattler, Thermische Trennverfahren [Thermal separation methods], 2nd Edition 1995, Weinheim, p. 135ff; Perry's Chemical Engineers Handbook, 7th Edition 1997, New York, Section 13). Thus, the distillation columns used may have separation-effective internals, such as separation trays, e.g. perforated trays, bubble-cap trays or valve trays, arranged packings, e.g. sheet-metal or fabric packings, or random beds of packings. The number of plates required in the column(s) used and the reflux ratio are essentially governed by the purity requirements and the relative boiling position of the liquids to be separated, with the skilled worker being able to ascertain the specific design and operating data by known methods.

In some embodiments, the distillation step substantially removes water and solvent. The temperature of distillation can be below 170 degrees C., below 160 degrees C., below 150 degrees C., or below 140 Degrees C.

Precipitation as salt may be achieved by adding suitable organic or inorganic acids, for example sulfuric acid, hydrochloric acid, phosphoric acid, acetic acid, formic acid, carbonic acid, oxalic acid, etc. In another preferred embodiment, an organic dicarboxylic acid is used, forming a salt which can be used, either directly or after purification, for example by recrystallization, in a subsequent polycondensation to give the polyamide. More specifically, such dicarboxylic acids are C4-C12-dicarboxylic acids.

The organic DA (e.g. HMD) phase produced in the extraction procedure may also be worked up chromatographically. For chromatography, the DA phase is applied to a suitable resin, for example a strongly or weakly acidic ion exchanger (such as Lewatit 1468 S, Dowex Marathon C, Amberlyst 119 Wet or others), with the desired product or the contaminants being partially or fully retained on the chromatographic resin. These chromatographic steps may be repeated, if necessary, using the same or other chromatographic resins. The skilled worker is familiar with selecting the appropriate chromatographic resins and their most effective application. The purified product may be concentrated by filtration or ultrafiltration and stored at an appropriate temperature.

The identity and purity of the compound(s) isolated may be determined by known technologies. These include high performance liquid chromatography (HPLC), gas chromatography (GC), spectroscopic methods, staining methods, thin layer chromatography, NIRS, enzyme assay or microbiological assays. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al.

(1987) Applications of HPLC in Biochemistry in: Laboratory Techniques in Biochemistry and Molecular Biology, Vol. 17.

The disclosed process may include various combinations of steps or processes as depicted in FIG. 4. Referring to FIG. 4, the system and steps include:

1. A fermentor or any vessel in which a microorganism may be cultured or grown in a suitable medium under suitable conditions and for a sufficient period of time to form one or more of diamine Carbonates and/or Carbamates in a cultured medium in the presence of carbon dioxide, carbonate, bicarbonate or carbonic acid.
2. Microbiol Heat Kill/Conversion: Many processes require inactivation of the microbial culture post-fermentation. Once the diamine Carbonates and/or Carbamates are formed, they may be converted to the free base where CO2 is released if sterilization/heat kill step occurs at elevated temperatures.
3: Solids removal: The solids from the cultured medium may be optionally removed before the diamine Carbonates and/or Carbamates are converted to release CO2.
4: Conversion (all possible ways to release CO2). The released CO2 may be recycled to fermentor.
5: Water Removal: removing water from the DA free base mixture, and optional recycling water and/or carbon dioxide to the fermentor;
6: Solvent Extraction, extracting the DA mixture with organic solvent in an extractor to form an organic phase DA solution and aqueous raffinate, and optionally recycling the aqueous raffinate to the conversion step;
7: Purification: Involves distillation which optionally recycles organic solvent back to the solvent extraction step, and purification could involve more distillation columns to purify the diamine and other steps to remove color forming compounds and the like.
8: Purified DA: the resulting purified DA free base from the steps above;
9: Optional Microbiol Heat Kill, where no CO2 is released
10: Optional water removal, recycle of water and possible CO2 if released removing water from the Carbonates and/or Carbamates mixture, and optional recycling water and/or carbon dioxide to the fermentor;
11: Optional direct purification from aqueous phase with or without release of CO2, could involve distillation, ion exchange, electrodialysis, and other suitable processes or steps. Possible to recycle water and CO2 if produced in these steps: optionally directly converting the Carbonates and/or Carbamates from the cultured medium to form a DA free base mixture, and optionally releasing of water and/or carbon dioxide that may be recycled to the fermentor;
12: Alkalization (NaOH or CaOH) or other steps to remove Carbonates from HMD (Ion exchange, electrodialysis, etc.): adding an aqueous base to the remove the Carbonates and/or Carbamates from the DA free base mixture.

Referring to FIG. 4, some of the various combinations of steps are as follows:
1, 2, 3, 4, 5, 6, 7, 8
1, 3, 4, 5, 6, 7, 8
1, 9, 3, 4, 5, 6, 7, 8
1, 2, 3, 10, 4, 5, 6, 7, 8
1, 3, 10, 4, 5, 6, 7, 8
1, 9, 3, 10, 4, 5, 6, 7, 8
1, 2, 3, 10, 11, 8
1, 3, 10, 11, 8
1, 9, 3, 10, 11, 8
1, 2, 3, 11, 8
1, 3, 11, 8
1, 9, 3, 11, 8
1, 2, 3, 4, 11, 8
1, 2, 3, 10, 4, 11, 8
1, 3, 10, 4, 11, 8
1, 3, 4, 11, 8
1, 9, 3, 4, 11, 8
1, 9, 3, 10, 4, 11, 8
1, 2, 3, 4, 12, 6, 7, 8
1, 2, 3, 10, 4, 12, 6, 7, 8
1, 3, 4, 12, 6, 7, 8
1, 3, 10, 4, 12, 6, 7, 8
1, 9, 3, 4, 12, 6, 7, 8
1, 9, 3, 10, 4, 12, 6, 7, 8
1, 2, 3, 4, 5, 12, 6, 7, 8
1, 2, 3, 10, 4, 5, 12, 6, 7, 8
1, 3, 4, 5, 12, 6, 7, 8
1, 3, 10, 4, 5, 12, 6, 7, 8
1, 9, 3, 4, 5, 12, 6, 7, 8
1, 9, 3, 10, 4, 5, 12, 6, 7, 8

The disclosed process can be applied in principle using any diamine-containing cultured medium (e.g. HMD-containing cultured medium). There are also in principle no limitations whatsoever regarding the microorganisms employed in the culturing or fermentation. The microorganism may be naturally occurring microorganisms; microorganisms improved by means of mutation and selection, and recombinantly produced or genetically engineered microorganisms, such as bacteria and fungi. These microorganisms are capable either of producing a DA or DA derivative, HMD and/or HMD derivatives such as HMD carbonate or HMD bicarbonate. More specifically, a recombinant organism employed is capable of DA biosynthesis, e.g. HMD biosynthesis via the HMD pathways ("HMD pathway") discussed below and as disclosed in U.S. Pat. No. 8,377,680, or other references cited herein, which disclosures are hereby incorporated by reference in its entirety.

In some embodiments, the genetically engineered microorganism that has a DA pathway including at least one exogenous nucleic acid encoding at least one enzyme of the DA pathway can also include an exogenous nucleic acid encoding a carbonic anhydrase enzyme. In other embodiments, the genetically engineered microorganism has a DA synthesis pathway, preferably an HMD synthesis pathway, with at least two exogenous nucleic acids encoding at least one enzyme of the DA synthesis pathway, preferably HMD synthesis pathway, and a carbonic anhydrase enzyme or variant expressed in a sufficient amount to produce at least one DA Carbonates and/or DA Carbamates, preferably HMD Carbonates and/or Carbamates, compound. In other embodiments, the genetically engineered microorganism has a DA synthesis pathway, preferably an HMD synthesis pathway, with at least two exogenous nucleic acids encoding at least one enzyme of the DA synthesis pathway, preferably the HMD synthesis pathway, and a carbonic anhydrase enzyme or variant expressed in a sufficient amount to produce at least one or more DA free base, preferably HMD free base, and carbon dioxide. It should be understood that a process for a diamine production can include the genetically engineered microorganisms as discussed above and that has a DA pathway, preferably HMD synthesis pathway, and a carbonic anhydrase enzyme or variant expressed in a sufficient amount to produce at least one DA Carbonates and/or DA Carbamates, preferably HMD Carbonates and/or Carbamates, compound or that can produce, at least one or more DA free base, preferably HMD free base, and carbon dioxide or both.

Exemplary HMD synthesis pathways include pathways depicted in FIGS. 10, 11, 13, 20, 21, 22, 24, 25 and 26. Disclosed are various pathways for the production of HMD. For example, the HMD pathways include the following:

a) steps depicted as A-N of FIG. 13.
b) steps A/L/N/C of FIG. 13.
c) steps M/N/C of FIG. 13.
d) steps D/E/F/G/H of FIG. 13).
e) steps D/I/J/G/H of FIG. 13).
f) steps D/E/K/J/G of FIG. 13
g) steps A-H of FIG. 15
h) steps A/B/C/D/E/R/S of FIG. 16
i) steps A/B/F/G/D/E/R/S of FIG. 16
j) steps A/B/H/I/D/E/R/S of FIG. 16
k) steps A/B/C/AB/Z/R/S of FIG. 16
l) steps A/B/H/I/AB/Z/R/S of FIG. 16
m) steps A/B/F/G/AB/Z/R/S of FIG. 16
n) steps A/B//J/O/P/Q/S of FIG. 16
o) steps A/B/J/M/N/P/Q/S of FIG. 16
p) steps A/B/J/K/UP/Q/S of FIG. 16
q) steps A/B/J/O/Z/R/S of FIG. 16
r) steps A/B/J/K/L/Z/R/S of FIG. 16
s) steps A/B/J/M/N/Z/R/S of FIG. 16
t) steps A/B/J/T/W/Q/S of FIG. 16
u) steps A/B/J/T/U/X/Q/S of FIG. 16
v) steps A/B/J/TN/Y/Q/S of FIG. 16
w) steps A-G of FIG. 17
x) steps O/C or D/P/G/H of FIG. 19
y) Steps A/B/C/G/H/I/J/K/UM of FIG. 21.
z) steps K/L/H of FIG. 21
aa) steps I/J/H of FIG. 21
bb); steps I/G/C of FIG. 21
cc) steps A/B/C of FIG. 21
dd) steps A/M/H of FIG. 21
ee) steps A/B/C of FIG. 22
ff) steps A/E/F/G/AA of FIG. 20

Any of the disclosed HMD synthesis pathways may be used to generate a genetically engineered microorganism that produces the pathway, pathway intermediate or product as desired. For example, the genetically engineered microorganism can have a HMD pathway including at least one exogenous nucleic acid encoding at least one enzyme of the HMD synthesis pathway expressed in a sufficient amount to produce at least one HMD Carbonates and/or Carbamates compound. The genetically engineered microorganism can have a HMD pathway including at least two, at least three, at least four, at least five, at least six, at least seven, at least eight, at least nine, at least ten, or at least eleven exogenous nucleic acids encoding enzymes of the HMD synthesis pathway. The exogenous nucleic acids can encode, for example, polypeptides, where the polypeptide is an enzyme or protein that can convert desired substrates, intermediates and produce products of the desired HMD synthesis pathways.

In some embodiments, the genetically engineered microorganism that has a HMD pathway including at least one exogenous nucleic acid encoding at least one enzyme of the HMD can also include an exogenous nucleic acid encoding a carbonic anhydrase enzyme.

For example, the HMD synthesis pathway may include intermediates such as 3-oxoadipyl-CoA, adipate semialdehyde, 6-aminocaproate (6-ACA), 6-ACA semialdehyde, 2-aminopimelate, 3, 6-dihydroxyhexanoyl-CoA and homolysine.

In some embodiments, the HMD synthesis pathway may include enzymes such as 3-oxoadipyl-CoA thiolase, 6-ACA transaminase or dehydrogenase, 6-aminocaproyl-CoA reductase, 6-ACA reductase, adipyl-CoA reductase, adipate reductase, 6-hydroxy 3-oxohexanoyl-CoA dehydrogenase, 2-aminopimelate decarboxylase, and homolysine decarboxylase.

In other embodiments, the HMD synthesis pathway may include an enzyme and substrate-product pair such as 3-oxoadipyl-CoA thiolase that acts on succinyl-CoA and acetyl-CoA to make 3-oxoadipyl-CoA, 6-ACA transaminase that acts on adipyl-CoA to form 6-ACA, 6-aminocaproyl-CoA reductase that acts on 6-aminocaproyl-CoA to form 6-ACA semialdehyde, 6-ACA reductase that acts on 6-ACA and converts it directly to 6-ACA semialdehyde, adipyl-CoA reductase that acts on adipyl-CoA to form adipate semialdehyde, adipate reductase that acts on adipate and converts it directly to adipate semialdehyde, 6-hydroxy 3-oxohexanoyl-CoA dehydrogenase that reduces 6-hydroxy 3-oxohexanoyl-CoA to form 3,6-dihydroxy hexanoyl-CoA, 2-aminopimelate decarboxylase that decarboxylates 2-aminopimelate to form 6-ACA, and homolysine decarboxylase that decarboxylates homolysine to form HMDA.

In some embodiments, a microorganism may produce the desired diamine (e.g. HMD) via a desired synthesis pathway that may include the following:

(a) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 6-ACA transferase or synthetase and 6-ACA-CoA reductase, or 6-ACA reductase, HMDA transaminase or dehydrogenase;

(b) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 6-ACA reductase, HMDA transaminase or dehydrogenase;

(c) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA transferase, hydrolase or transferase, adipate reductase, 6-ACA transaminase or dehydrogenase, 6-ACA transferase or synthetase, 6-ACA-CoA reductase, HMDA transaminase or dehydrogenase;

(d) 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA transferase, hydrolase or transferase, adipate reductase, 6-ACA transaminase or dehydrogenase, 6-ACA reductase, HMDA transaminase or dehydrogenase;

(e) 3-oxoadipyl-CoA thiolase, 3-oxoadipate dehydrogenase, 3-hydroxyadipate dehydratase, 5-carboxy-2-pentenoate reductase, adipate reductase, 6-ACA transaminase or dehydrogenase, 6-ACA transferase or synthetase, 6-ACA-CoA reductase, HMDA transaminase or dehydrogenase;

(f) 3-oxoadipyl-CoA thiolase, 3-oxoadipate dehydrogenase, 3-hydroxyadipate dehydratase, 5-carboxy-2-pentenoate reductase, adipate reductase, 6-ACA transaminase or dehydrogenase, 6-ACA reductase, HMDA transaminase or dehydrogenase;

(g) 3-oxoadipyl-CoA thiolase, 3-oxoadipate dehydrogenase, 3-hydroxyadipate dehydratase, 5-carboxy-2-pentenoate reductase, adipyl-CoA transferase, hydrolase or transferase, adipyl-CoA reductase, 6-ACA transaminase or dehydrogenase, 6-ACA transferase or synthetase, 6-ACA-CoA reductase, HMDA transaminase or dehydrogenase;

(h) 3-oxoadipyl-CoA thiolase, 3-oxoadipate dehydrogenase, 3-hydroxyadipate dehydratase, 5-carboxy-2-pentenoate reductase, adipyl-CoA transferase, hydrolase or transferase, adipyl-CoA reductase, 6-ACA transaminase or dehydrogenase, 6-ACA reductase, HMDA transaminase or dehydrogenase;

(i) an 4-hydroxy-2-oxoheptane-I,7-dioate (HODH aldolase); an 2-oxohept-4-ene-I,7-dioate (OHED) hydratase; an OHED formate-lyase and a pyruvate formate-lyase activating enzyme or OHED dehydrogenase; a 2,3-dehydroadipyl-CoA reductase; an adipyl-CoA dehydrogenase; or an adipate semialdehyde aminotransferase or an adipate semialdehyde oxidoreductase (aminating);

(j) a β-ketothiolase or an acetyl-CoA carboxylase and an acetoacetyl-CoA synthase, a 3-hydroxyacyl-CoA dehydrogenase or a 3-oxoacyl-CoA reductase, an enoyl-CoA hydratase, and a trans-2-enoyl-CoA reductase for producing hexanoyl-CoA, one or more of a thioesterase, an aldehyde dehydrogenase, or a butanal dehydrogenase, said host producing hexanal or hexanoates; one or more of a monooxygenase, an alcohol dehydrogenase, an aldehyde dehydrogenase, a 6-hydroxyhexanoate dehydrogenase, a 5-hydroxypentanoate dehydrogenase, a 4-hydroxybutyrate dehydrogenase, a 6-oxohexanoate dehydrogenase, or a 7-oxoheptanoate dehydrogenase, said host producing adipic acid or adipate semialdehyde; one or more of a monooxygenase, a transaminase, a 6-hydroxyhexanoate dehydrogenase, a 5-hydroxypentanoate dehydrogenase, a 4-hydroxybutyrate dehydrogenase, and an alcohol dehydrogenase, said host producing 6-aminohexanoate; one or more of a carboxylate reductase, a w-transaminase, a deacetylase, a N-acetyl transferase, or an alcohol dehydrogenase. Such pathway is disclosed in U.S. Patent Application Publication No. 20140186902;

(k) acetyltransferase or thiolase to form 6-hydroxy-3-oxo-hexanoyl-CoA, 6-hydroxy-3-oxo-hexanoyl-CoA dehydrogenase, 3,4-dihydroxyhexanoyl-CoA dehydratase, 6-hydroxy-2-hexenoyl-CoA reductase, 6-hydroxy-hexanoyl-CoA hydrolase to form 6-ACA, 6-hydroxy-caproate dehydrogenase and transaminase to form HMDA. Such pathway is disclosed in International Application Publication No. WO 2014/047407A1;

(l) homocitrate synthase, a homoaconitase and a homoisocitrate dehydrogenase to form 2-ketopimelate, 2-keto decarboxylase catalyzing the conversion of α-ketopimelate to adipate semialdehyde, 2-aminotransferase catalyzes the conversion of α-ketopimelate to 2-aminopimelate, 2-aminopimelate decarboxylase to decarboxylate 2-aminopimelate and form 6-ACA, aldehyde dehydrogenase catalyzes the conversion of 6-ACA to 6-aminohexanal and the aminotransferase catalyzes the conversion of 6-aminohexanal to 6-hexamethylenediamine. Such pathway is disclosed in International Application Publication No. in WO/2010/068944; and (m) glutamyl-CoA transferase and/or ligase, beta-ketothiolase, 3-oxo-6-aminopimeloyl-CoA oxidoreductase, 3-hydroxy-6-aminopimeloyl-CoA dehydratase, 6-amino-7-carboxyhept-2-enoyl-CoA reductase, 6-aminopimeloyl-CoA reductase (aldehyde forming), 2-amino-7-oxoheptanoate aminotransferase and/or aminating oxidoreductase, homolysine decarboxylase, 6-aminopimeloyl-CoA hydrolase, transferase and/or ligase, 2-aminopimelate decarboxylase. Such pathway is disclosed in International Application Publication No. WO 2010/129936

In some embodiments, the HMD synthesis pathway includes at least one enzyme and the nucleic acids encoding such one or more enzymes for 3-oxoadipyl-CoA thiolase, 3-oxoadipyl-CoA dehydrogenase, 3-hydroxyadipyl-CoA dehydratase, 5-carboxy-2-pentenoyl-CoA reductase, adipyl-CoA reductase, 6-ACA transaminase or dehydrogenase, 3-oxoadipyl-CoA:acyl CoA transferase, 3-oxoadipate dehydrogenase, 3-hydroxyadipate dehydratase, 5-carboxy-2-pentenoate reductase, adipyl-CoA transferase, ligase, or hydrolase, 6-ACA transferase or synthetase, 6-ACA-CoA reductase, HMDA transaminase or dehydrogenase, adipate reductase, 6-ACA transaminase or dehydrogenase, or 6-ACA reductase.

Suitable microorganisms that can be used as a host to include one or more exogenous nucleic acids of the HMD synthesis pathways include for example prokaryotes such as bacteria, and eukaryotes such as, fungus (e.g. yeast) or any other microorganisms applicable to fermentation processes or that can tolerate pH conditions below pH 4.

In some embodiments, the genetically engineered microorganism *Escherichia, Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*, the genus *Alkaliphilus, Methylobacterium, Methyloversatilis, Methylococcus, Methylocystis* and *Hyphomicrobium* the order Saccharomycetales, family Saccharomycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccharomycetaceae, including the genus *Schizosaccharomyces*; the order Eurotiales, family Trichocomaceae, including the genus *Aspergillus*; and the order Mucorales, family Mucoraceae, including the genus *Rhizopus*.

In other embodiments the genetically engineered microorganism comprises non-limiting species of host bacteria include *Escherichia coli, Klebsiella oxytoca, Anaerobiospirillum succiniciproducens, Actinobacillus succinogenes, Mannheimia succiniciproducens, Rhizobium etli, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida, Bacillus pseudofirmus, Bacillus halodurans, Bacillus alcalophilus, Clostridium paradoxum, Saccharomyces cerevisiae, Schizosaccharomyces pombe, Hansenula polymorpha, Pichia methanolica, Candida boidinii, Kluyveromyces lac-* tis, *Kluyveromyces marxianus, Aspergillus terreus, Aspergillus niger, Pichia pastoris, Rhizopus arrhizus, Rhizopus oryzae, Yarrowia lipolytica,* and *Issatchenkia orientalis.* Some alkaliphiles are: *Bacillis pseudofirmus, Bacillus halodurans, Bacillus alcalophilus, Clostridium paradoxum, Arthrospira platensis, Bacillus clausii, Oceanobacillus iheyensis, Alkaliphilus metalliredigens, Alkaliphilus oremlandii, Bacillus selentireducens, Desulfovibrio alkaliphiles, Dethiobacter alkaliphiles, Thioalkalivibrio* sp., *Natranaerobius thermophilus, Alkalilimnicola ehrlichii,* and *Desulfonatronospira thiodismutans.*

In some embodiments, the species of fungi or yeast can be selected from *Saccharomyces cerevisiae, Schizosaccharomyces pombe, Hansenula polymorpha, Pichia methanolica, Candida boidinii, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and *Issatchenkia orientalis* and the like.

In some embodiments, the genetically engineered microorganism is *Escherichia coli, Corynebacterium glutamicum, Bacillus subtilis, Pseudomonas putida, Bacillis pseudofirmus, Bacillus halodurans, Bacillus alcalophilus, Clostridium paradoxum, Saccharomyces cerevisiae.*

For example, *E. coli* is a particularly useful host organism since it is a well characterized microbial organism suitable for genetic engineering. Other particularly useful host organisms include yeast such as *Saccharomyces cerevisiae.* In some embodiments, genetically engineered microorganisms are modified that have improved alkali tolerance.

Alkali tolerance can be introduced into organisms that are not typically alkali-tolerant using adaptive evolution. Cells are grown under increasingly higher pH conditions till they have adapted their cellular mechanisms to grow optimally at the desired high pH (alkaline pH). Typically, small volumes of cells, still growing in exponential phase, are transferred to a fresh medium at a predetermined pH till they have reached a certain biomass concentration. These cells are then diluted into a fresh medium where an incrementally higher pH is maintained. This process selects for cells that are more fit to grow at the higher pH. The process of transferring small volume of exponentially growing cells into fresh medium at higher pH is continued till the cells have evolved to grow at the target pH level.

Adaptive evolution has been used to evolve strains to grow on non-natural substrates (Lee and Palsson, Appl Environ Microbiol. 2010 July; 76(13):4158-68, Adaptive evolution of *Escherichia coli* K-12 MG1655 during growth on a Nonnative carbon source, L-1,2-propanediol), for improved salt tolerance (Ketola and Hiltunen, Ecol Evol. 2014 October; 4:3901-8, Rapid evolutionary adaptation to elevated salt concentrations in pathogenic freshwater bacteria *Serratia marcescens*), for improved product tolerance (Kildegaard K R et al., Metab Eng. 2014 Sep. 28; 26C:57-66, Evolution reveals a glutathione-dependent mechanism of 3-hydroxypropionic acid tolerance), for growth at high temperature (Sandeberg et al., Mol Biol Evol. 2014 October; 31(10):2647-62, Evolution of *Escherichia coli* to 42° C. and subsequent genetic engineering reveals adaptive mechanisms and novel mutations), to evolve for fermentation under aerobic conditions (Portnoy et al., Appl Environ Microbiol. 2008 December; 74(24), Aerobic fermentation of D-glucose by an evolved cytochrome oxidase-deficient *Escherichia coli* strain) among several other objectives.

For example, one of the pathways entails the activation of 6-aminocaproate to 6-aminocaproyl-CoA by a transferase or synthase enzyme (FIG. 10, Step Q or R) followed by the spontaneous cyclization of 6-aminocaproyl-CoA to form caprolactam (FIG. 10, Step T). In other described pathways, the pathway entails the activation of 6-aminocaproate to 6-aminocaproyl-CoA (FIG. 10, Step Q or R), followed by a reduction (FIG. 10, Step U) and amination (FIG. 10, Step V or W) to form HMD. 6-Aminocaproic acid can alternatively be activated to 6-aminocaproyl-phosphate instead of 6-aminocaproyl-CoA. 6-Aminocaproyl-phosphate can spontaneously cyclize to form caprolactam. Alternatively, 6-aminocaproyl-phosphate can be reduced to 6-aminocaproate semialdehye, which can be then converted to HMD as depicted in FIGS. 10 and 11. In either case, the amination reaction must occur relatively quickly to minimize the spontaneous formation of the cyclic imine of 6-aminocaproate semialdehyde. Linking or scaffolding the participating enzymes represents a potentially powerful option for ensuring that the 6-aminocaproate semialdehyde intermediate is efficiently channeled from the reductase enzyme to the amination enzyme.

Another option for minimizing or even eliminating the formation of the cyclic imine or caprolactam during the conversion of 6-aminocaproic acid to HMD entails adding a functional group (for example, acetyl, succinyl) to the amine group of 6-aminocaproic acid to protect it from cyclization. This is analogous to ornithine formation from L-glutamate in *Escherichia coli*. Specifically, glutamate is first converted to N-acetyl-L-glutamate by N-acetylglutamate synthase. N-Acetyl-L-glutamate is then activated to N-acetylglutamyl-phosphate, which is reduced and transaminated to form N-acetyl-L-ornithine. The acetyl group is then removed from N-acetyl-L-ornithine by N-acetyl-L-ornithine deacetylase forming L-ornithine. Such a route is necessary because formation of glutamate-5-phosphate from glutamate followed by reduction to glutamate-5-semialdehyde leads to the formation of (S)-1-pyrroline-5-carboxylate, a cyclic imine formed spontaneously from glutamate-5-semialdehyde. In the case of forming HMD from 6-aminocaproic acid, the steps can involve acetylating 6-aminocaproic acid to acetyl-6-aminocaproic acid, activating the carboxylic acid group with a CoA or phosphate group, reducing, aminating, and deacetylating.

Note that 6-aminocaproate can be formed from various starting molecules. For example, the carbon backbone of 6-aminocaproate can be derived from succinyl-CoA and acetyl-CoA as depicted in FIG. 10 and also described in FIGS. 2, 3 and 8. Alternatively, 6-aminocaproate can be derived from alpha-ketoadipate, where alpha-ketoadipate is converted to adipyl-CoA (see FIG. 9), and adipyl-CoA is converted to 6-aminocaproate as shown in FIG. 10.

FIG. 11 provides two additional metabolic pathways to 6-aminocaproate or 6-aminocapropyl-CoA starting from 4-aminobutyryl-CoA and acetyl-CoA. The first route entails the condensation of 4-aminobutyryl-CoA and acetyl-CoA to form 3-oxo-6-aminohexanoyl-CoA (Step A) followed by a reduction (Step B), dehydration (Step C), and reduction (Step D) to form 6-aminocaproyl-CoA. 6-Aminocaproyl-CoA can be converted to 6-aminocaproate by a transferase (Step K), synthase (Step L), or hydrolase (Step M) enzyme. Alternatively, 6-aminocaproyl-CoA can be converted to caprolactam by spontaneous cyclization (Step Q) or to HMD following its reduction (Step N) and amination (Step O or P). The second pathway described in FIG. 11 entails the condensation of 4-aminobutyryl-CoA and acetyl-CoA to form 3-oxo-6-aminohexanoyl-CoA (Step A) which is then converted to 3-oxo-6-aminohexanoate by a transferase (Step E), synthase (Step F), or hydrolase (Step G). 3-Oxo-6-aminohexanoate is then reduced (Step H), dehydrated (Step I), and reduced (Step J) to form 6-aminocaproate.

The starting molecule, 4-aminobutyryl-CoA, can be formed from various common central metabolites. For example, glutamate can be decarboxylated to 4-aminobutyrate, which is then activated by a CoA-transferase or synthase to 4-aminobutyryl-CoA. Alternatively, succinate semialdehyde, formed from either the reduction of succinyl-CoA or the decarboxylation of alpha-ketoglutarate, can be transaminated to 4-aminobutyrate prior to activation by a CoA-transferase or synthase to form 4-aminobutyryl-CoA. It is noted that 4-aminobutyryl-CoA and several of the intermediates of the 4-aminobutyryl-CoA to 6-aminocaproyl-CoA pathway may spontaneously cyclize to their corresponding lactams. Thus, adding a protective functional group to the terminal amine group of 4-aminobutyryl-CoA and/or several of the amino-CoA intermediates can be used to minimize the formation of unwanted cyclic byproducts. In this case, the same general set of transformations depicted in FIG. 11 would apply, although two additional steps, for example, an acetylase and deacetylase, can be added to the pathway.

All transformations depicted in FIGS. 10-11 fall into the 12 general categories of transformations shown in Table 8. Below is described a number of biochemically characterized candidate genes in each category. Specifically listed are genes that can be applied to catalyze the appropriate transformations in FIGS. 10-11 when cloned and expressed.

TABLE 8

Enzyme types for conversion of succinyl-CoA, acetyl-CoA, and/or 4-aminobutyryl-CoA to 6-amino-caproate, caprolactam, and/or hexamethylenediamine. The first three digits of each label correspond to the first three Enzyme Commission number digits which denote the general type of transformation independent of substrate specificity.

| Label | Function |
| --- | --- |
| 1.1.1.a | Oxidoreductase (ketone to hydroxyl or aldehyde to alcohol) |
| 1.2.1.b | Oxidoreductase (acyl-CoA to aldehyde) |
| 1.3.1.a | Oxidoreductase operating on CH—CH donors |
| 1.4.1.a | Oxidoreductase operating on amino acids |
| 2.3.1.b | Acyltransferase |
| 2.6.1.a | Aminotransferase |
| 2.8.3.a | Coenzyme-A transferase |
| 3.1.2.a | Thiolester hydrolase (CoA specific) |
| 4.2.1.a | Hydro-lyase |
| 6.2.1.a | Acid-thiol ligase |
| 6.3.1.a/6.3.2.a | Amide synthases/peptide synthases |
| No enzyme required | Spontaneous cyclization |

1.1.1.a Oxidoreductases. Four transformations depicted in FIGS. 10 and 11 require oxidoreductases that convert a ketone functionality to a hydroxyl group. Step B in both FIGS. 10 and 11 involves converting a 3-oxoacyl-CoA to a 3-hydroxyacyl-CoA. Step H in both FIGS. 1 and 2 involves converting a 3-oxoacid to a 3-hydroxyacid.

Exemplary enzymes that can convert 3-oxoacyl-CoA molecules such as 3-oxoadipyl-CoA and 3-oxo-6-aminohexanoyl-CoA into 3-hydroxyacyl-CoA molecules such as 3-hydroxyadipyl-CoA and 3-hydroxy-6-aminohexanoyl-CoA, respectively, include enzymes whose natural physiological roles are in fatty acid beta-oxidation or phenylacetate catabolism. For example, subunits of two fatty acid oxidation complexes in E. coli, encoded by fadB and fadJ, function as 3-hydroxyacyl-CoA dehydrogenases (Binstock et al., Methods Enzymol. 71:403-411 (1981)). Furthermore, the gene products encoded by phaC in Pseudomonas putida U (Olivera et al., Proc. Natl. Acad. Sci. USA 95:6419-6424 (1998)) and paaC in Pseudomonas fluorescens ST (Di Gennaro et al., Arch. Microbiol. 188:117-125 (2007)) catalyze the reverse reaction of step B in FIG. 10, that is, the oxidation of 3-hydroxyadipyl-CoA to form 3-oxoadipyl-CoA, during the catabolism of phenylacetate or styrene. Note that the reactions catalyzed by such enzymes are reversible. In addition, given the proximity in E. coli of paaH to other genes in the phenylacetate degradation operon (Nogales et al., Microbiology 153:357-365 (2007)) and the fact that paaH mutants cannot grow on phenylacetate (Ismail et al., Eur. J. Biochem. 270:3047-3054 (2003)), it is expected that the E. coli paaH gene encodes a 3-hydroxyacyl-CoA dehydrogenase.

| Gene name | GI# | GenBank Accession # | Organism |
| --- | --- | --- | --- |
| fadB | 119811 | P21177.2 | Escherichia coli |
| fadJ | 3334437 | P77399.1 | Escherichia coli |
| paaH | 16129356 | NP_415913.1 | Escherichia coli |
| phaC | 26990000 | NP_745425.1 | Pseudomonas putida |
| paaC | 106636095 | ABF82235.1 | Pseudomonas fluorescens |

Additional exemplary oxidoreductases capable of converting 3-oxoacyl-CoA molecules to their corresponding 3-hydroxyacyl-CoA molecules include 3-hydroxybutyryl-CoA dehydrogenases. The enzyme from Clostridium acetobutylicum, encoded by hbd, has been cloned and functionally expressed in E. coli (Youngleson et al., J. Bacteriol. 171:6800-6807 (1989)). Additional gene candidates include Hbd1 (C-terminal domain) and Hbd2 (N-terminal domain) in Clostridium kluyveri (Hillmer et al., FEBS Lett. 21:351-354 (1972)) and HSD17B10 in Bos taurus (Wakil et al., J. Biol. Chem. 207:631-638 (1954)). Yet other gene candidates demonstrated to reduce acetoacetyl-CoA to 3-hydroxybutyryl-CoA are phbB from Zoogloea ramigera (Ploux et al., Eur. J. Biochem. 174:177-182 (1988)) and phaB from Rhodobacter sphaeroides (Alber et al., Mol. Microbiol 61:297-309 (2006)). The former gene candidate is NADPH-dependent, its nucleotide sequence has been determined (Peoples et al., Mol. Microbiol. 3:349-357 (1989)) and the gene has been expressed in E. coli. Substrate specificity studies on the gene led to the conclusion that it could accept 3-oxopropionyl-CoA as a substrate besides acetoacetyl-CoA (Ploux et al., supra).

| Gene name | GI# | GenBank Accession # | Organism |
| --- | --- | --- | --- |
| hbd | 18266893 | P52041.2 | Clostridium acetobutylicum |
| Hbd2 | 146348271 | EDK34807.1 | Clostridium kluyveri |
| Hbd1 | 146345976 | EDK32512.1 | Clostridium kluyveri |
| HSD17B10 | 3183024 | O02691.3 | Bos taurus |
| phbB | 130017 | P23238.1 | Zoogloea ramigera |
| phaB | 146278501 | YP_001168660.1 | Rhodobacter sphaeroides |

A number of similar enzymes have been found in other species of Clostridia and in Metallosphaera sedula (Berg et al., Science 318:1782-1786 (2007)).

| Gene name | GI# | GenBank Accession # | Organism |
| --- | --- | --- | --- |
| hbd | 15895965 | NP_349314.1 | Clostridium acetobutylicum |
| hbd | 20162442 | AAM14586.1 | Clostridium beijerinckii |
| Msed_1423 | 146304189 | YP_001191505 | Metallosphaera sedula |
| Msed_0399 | 146303184 | YP_001190500 | Metallosphaera sedula |
| Msed_0389 | 146303174 | YP_001190490 | Metallosphaera sedula |
| Msed_1993 | 146304741 | YP_001192057 | Metallosphaera sedula |

Various alcohol dehydrogenases represent good candidates for converting 3-oxoadipate to 3-hydroxyadipate (step H, FIG. 10) or 3-oxo-6-aminohexanoate to 3-hydroxy-6-aminohexanoate (step H, FIG. 11). Two such enzymes capable of converting an oxoacid to a hydroxyacid are encoded by the malate dehydrogenase (mdh) and lactate dehydrogenase (ldhA) genes in *E. coli*. In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional candidate for these steps is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismaiel et al., *J. Bacteriol.* 175:5097-5105 (1993) and *T. brockii* (Lamed et al., *Biochem. J.* 195:183-190 (1981); Peretz et al., *Biochemistry* 28:6549-6555 (1989)).

| Gene name | GI# | GenBank Accession # | Organism |
|---|---|---|---|
| mdh | 1789632 | AAC76268.1 | *Escherichia coli* |
| ldhA | 16129341 | NP_415898.1 | *Escherichia coli* |
| ldh | 113866693 | YP_725182.1 | *Ralstonia eutropha* |
| bdh | 177198 | AAA58352.1 | *Homo sapiens* |
| adh | 60592974 | AAA23199.2 | *Clostridium beijerinckii* |
| adh | 113443 | P14941.1 | *Thermoanaerobacter brockii* |

1.2.1.b Oxidoreductase (acyl-CoA to aldehyde). The transformations of adipyl-CoA to adipate semialdehyde (Step N, FIGS. 10) and 6-aminocaproyl-CoA to 6-aminocaproate semialdehyde (Step U, FIG. 10; Step N, FIG. 11) require acyl-CoA dehydrogenases capable of reducing an acyl-CoA to its corresponding aldehyde. Exemplary genes that encode such enzymes include the *Acinetobacter calcoaceticus* acr1 encoding a fatty acyl-CoA reductase (Reiser et al, *J. Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling et al., *J. Bacteriol.* 178:871-880 (1996)). SucD of *P. gingivalis* is another succinate semialdehyde dehydrogenase (Takahashi et al., *J. Bacteriol.* 182:4704-4710 (2000)). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:43-55 (1972); Koo et al., *Biotechnol Lett.* 27:505-510 (2005)).

| Gene name | GI# | GenBank Accession # | Organism |
|---|---|---|---|
| acr1 | 50086359 | YP_047869.1 | *Acinetobacter calcoaceticus* |
| acr1 | 1684886 | AAC45217 | *Acinetobacter baylyi* |
| acr1 | 18857901 | BAB85476.1 | *Acinetobacter* sp. Strain M-1 |
| sucD | 172046062 | P38947.1 | *Clostridium kluyveri* |
| sucD | 34540484 | NP_904963.1 | *Porphyromonas gingivalis* |
| bphG | 425213 | BAA03892.1 | *Pseudomonas* sp |
| adhE | 55818563 | AAV66076.1 | *Leuconostoc mesenteroides* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., supra; Thauer R. K., *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., supra; Berg et al., supra). A gene encoding a malonyl-CoA reductase from *Sulfolobus tokodaii* was cloned and heterologously expressed in *E. coli* (Alber et al., supra). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl Environ Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra).

| Gene name | GI# | GenBank Accession # | Organism |
|---|---|---|---|
| Msed_0709 | 146303492 | YP_001190808.1 | *Metallosphaera sedula* |
| mcr | 15922498 | NP_378167.1 | *Sulfolobus tokodaii* |
| asd-2 | 15898958 | NP_343563.1 | *Sulfolobus solfataricus* |
| Saci_2370 | 70608071 | YP_256941.1 | *Sulfolobus acidocaldarius* |
| Ald | 49473535 | AAT66436 | *Clostridium beijerinckii* |
| eutE | 687645 | AAA80209 | *Salmonella typhimurium* |
| eutE | 2498347 | P77445 | *Escherichia coli* |

1.3.1.a Oxidoreductase operating on CH—CH donors. Referring to FIG. 10, step D refers to the conversion of 5-carboxy-2-pentenoyl-CoA to adipyl-CoA by 5-carboxy-2-pentenoyl-CoA reductase. Referring to FIG. 11, step D refers to the conversion of 6-aminohex-2-enoyl-CoA to 6-aminocaproyl-CoA. Enoyl-CoA reductase enzymes are suitable enzymes for either transformation. One exemplary enoyl-CoA reductase is the gene product of bcd from *C. acetobutylicum* (Boynton et al., *J Bacteriol.* 178:3015-3024 (1996); Atsumi et al., *Metab. Eng.* 2008 10(6):305-311

(2008)(Epub Sep. 14, 2007), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli* resulting in an active enzyme (Hoffmeister et al., supra). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci et al., *FEBS Letters* 581:1561-1566 (2007)).

| Gene name | GI# | GenBank Accession # | Organism |
|---|---|---|---|
| bcd | 15895968 | NP_349317.1 | Clostridium acetobutylicum |
| etfA | 15895966 | NP_349315.1 | Clostridium acetobutylicum |
| etfB | 15895967 | NP_349316.1 | Clostridium acetobutylicum |
| TER | 62287512 | Q5EU90.1 | Euglena gracilis |
| TDE0597 | 42526113 | NP_971211.1 | Treponema denticola |

Step J of both FIGS. 10 and 11 requires a 2-enoate reductase enzyme. 2-Enoate reductases (EC 1.3.1.31) are known to catalyze the NAD(P)H-dependent reduction of a wide variety of α,β-unsaturated carboxylic acids and aldehydes (Rohdich et al., *J. Biol. Chem.* 276:5779-5787 (2001)). 2-Enoate reductase is encoded by enr in several species of *Clostridia* (Giese) et al., *Arch Microbiol* 135:51-57 (1983)) including *C. tyrobutyricum*, and *C. thermoaceticum* (now called *Moorella thermoaceticum*) (Rohdich et al., supra). In the published genome sequence of *C. kluyveri*, 9 coding sequences for enoate reductases have been reported, out of which one has been characterized (Seedorf et al., *Proc. Natl. Acad. Sci. USA*, 105:2128-2133 (2008)). The enr genes from both *C. tyrobutyricum* and *C. thermoaceticum* have been cloned and sequenced and show 59% identity to each other. The former gene is also found to have approximately 75% similarity to the characterized gene in *C. kluyveri* (Giese) et al., supra). It has been reported based on these sequence results that enr is very similar to the dienoyl CoA reductase in *E. coli* (fadH) (Rohdich et al., supra). The *C. thermoaceticum* enr gene has also been expressed in an enzymatically active form in *E. coli* (Rohdich et al., supra).

| Gene name | GI# | GenBank Accession # | Organism |
|---|---|---|---|
| fadH | 16130976 | NP_417552.1 | Escherichia coli |
| enr | 169405742 | ACA54153.1 | Clostridium botulinum A3 str |
| enr | 2765041 | CAA71086.1 | Clostridium tyrobutyricum |
| enr | 3402834 | CAA76083.1 | Clostridium kluyveri |
| enr | 83590886 | YR_430895.1 | Moorella thermoacetica |

1.4.1.a Oxidoreductase operating on amino acids. FIG. 10 depicts two reductive aminations. Specifically, step P of FIG. 10 involves the conversion of adipate semialdehyde to 6-aminocaproate and step W of FIG. 10 entails the conversion of 6-aminocaproate semialdehyde to hexamethylenediamine. The latter transformation is also required in FIG. 11, Step P.

Most oxidoreductases operating on amino acids catalyze the oxidative deamination of alpha-amino acids with NAD+ or NADP+ as acceptor, though the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., Nucleic. Acids Res. 11:5257-5266 (1983); Korber et al., J. Mol. Biol. 234:1270-1273 (1993)), gdh from *Thermotoga maritima* (Kort et al., Extremophiles 1:52-60 (1997); Lebbink et al., J. Mol. Biol. 280:287-296 (1998); Lebbink et al., J. Mol. Biol. 289:357-369 (1999)), and gdhA1 from *Halobacterium salinarum* (Ingoldsby et al., Gene. 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Stoyan et al., J. Biotechnol 54:77-80 (1997); Ansorge et al., Biotechnol Bioeng. 68:557-562 (2000)). The nadX gene from *Thermotoga maritime* encoding for the aspartate dehydrogenase is involved in the biosynthesis of NAD (Yang et al., J. Biol. Chem. 278:8804-8808 (2003)).

| Gene name | GI# | Accession # | Organism |
|---|---|---|---|
| gdhA | 118547 | P00370 | Escherichia coli |
| gdh | 6226595 | P96110.4 | Thermotoga maritima |
| gdhA1 | 15789827 | NP_279651.1 | Halobacterium salinarum |
| ldh | 61222614 | P0A393 | Bacillus cereus |
| nadX | 15644391 | NP_229443.1 | Thermotoga maritima |

The lysine 6-dehydrogenase (deaminating), encoded by the lysDH genes, catalyze the oxidative deamination of the ε-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989); Misono et al., supra), and *Achromobacter denitrificans* (Ruldeekulthamrong et al., *BMB. Rep.* 41:790-795 (2008)). Such enzymes are particularly good candidates for converting adipate semialdehyde to 6-aminocaproate given the structural similarity between adipate semialdehyde and 2-aminoadipate-6-semialdehyde.

| Gene name | GI# | GenBank Accession # | Organism |
|---|---|---|---|
| lysDH | 13429872 | BAB39707 | Geobacillus stearothermophilus |
| lysDH | 15888285 | NP_353966 | Agrobacterium tumefaciens |
| lysDH | 74026644 | AAZ94428 | Achromobacter denitrificans |

2.3.1.b Acyl transferase. Referring to FIG. 10, step A involves 3-oxoadipyl-CoA thiolase, or equivalently, succinyl CoA:acetyl CoA acyl transferase (β-ketothiolase). The gene products encoded by pcaF in *Pseudomonas* strain B13 (Kaschabek et al., *J. Bacteriol.* 184:207-215 (2002)), phaD in *Pseudomonas putida* U (Olivera et al., supra), paaE in *Pseudomonas fluorescens* ST (Di Gennaro et al., supra), and paaJ from *E. coli* (Nogales et al., supra) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the synthesis of 3-oxoadipyl-CoA. For example, the ketothiolase phaA from *R. eutropha* combines two molecules of acetyl-CoA to form acetoacetyl-CoA (Sato et al., *J Biosci Bioeng* 103:38-44 (2007)). Similarly, a 3-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. In addition to the likelihood of possessing 3-oxoadipyl-CoA thiolase activity, all such enzymes represent good candidates for condensing 4-aminobutyryl-CoA and acetyl-CoA to form 3-oxo-6-aminohexanoyl-CoA (step A, FIG. 11) either in their native forms or once they have been appropriately engineered.

| Gene name | GI# | GenBank Accession # | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| paaE | 106636097 | ABF82237.1 | *Pseudomonas fluorescens* |

2-Amino-4-oxopentanoate (AKP) thiolase or AKP thiolase (AKPT) enzymes present additional candidates for performing step A in FIGS. 10 and 11. AKPT is a pyridoxal phosphate-dependent enzyme participating in ornithine degradation in *Clostridium sticklandii* (Jeng et al., *Biochemistry* 13:2898-2903 (1974); Kenklies et al., *Microbiology* 145: 819-826 (1999)). A gene cluster encoding the alpha and beta subunits of AKPT (or -2 (ortA) and or -3 (ortB)) was recently identified and the biochemical properties of the enzyme were characterized (Fonknechten et al., *J. Bacteriol.* In Press (2009)). The enzyme is capable of operating in both directions and naturally reacts with the D-isomer of alanine. AKPT from *Clostridium sticklandii* has been characterized but its protein sequence has not yet been published. Enzymes with high sequence homology are found in *Clostridium difficile*, *Alkaliphilus metalliredigenes* QYF, *Thermoanaerobacter* sp. X514, and *Thermoanaerobacter tengcongensis* MB4 (Fonknechten et al., supra).

| Gene name | GI# | GenBank Accession # | Organism |
|---|---|---|---|
| ortA (α) | 126698017 | YP_001086914.1 | *Clostridium difficile* 630 |
| ortB (β) | 126698018 | YP_001086915.1 | *Clostridium difficile* 630 |
| Amet_2368 (α) | 150390132 | YP_001320181.1 | *Alkaliphilus metalliredigenes* QYF |
| Amet_2369 (β) | 150390133 | YP_001320182.1 | *Alkaliphilus metalliredigenes* QYF |
| Teth514_1478 (α) | 167040116 | YP_001663101.1 | *Thermoanaerobacter* sp. X514 |
| Teth514_1479 (β) | 167040117 | YP_001663102.1 | *Thermoanaerobacter* sp. X514 |
| TTE1235 (α) | 20807687 | NP_622858.1 | *Thermoanaerobacter tengcongensis* MB4 |
| thrC (β) | 20807688 | NP_622859.1 | *Thermoanaerobacter tengcongensis* MB4 |

2.6.1.a Aminotransferase. Step O of FIGS. 10 and 11 and Step V of FIG. 10 require transamination of a 6-aldehyde to an amine. These transformations can be catalyzed by gamma-aminobutyrate transaminase (GABA transaminase). One *E. coli* GABA transaminase is encoded by gabT and transfers an amino group from glutamate to the terminal aldehyde of succinyl semialdehyde (Bartsch et al., *J. Bacteriol.* 172:7035-7042 (1990)). The gene product of puuE catalyzes another 4-aminobutyrate transaminase in *E. coli* (Kurihara et al., *J. Biol. Chem.* 280:4602-4608 (2005)). GABA transaminases in *Mus musculus*, *Pseudomonas fluorescens*, and *Sus scrofa* have been shown to react with 6-aminocaproic acid (Cooper, *Methods Enzymol.* 113:80-82 (1985); Scott et al., *J. Biol. Chem.* 234:932-936 (1959)).

| Gene name | GI# | GenBank Accession # | Organism |
|---|---|---|---|
| gabT | 16130576 | NP_417148.1 | *Escherichia coli* |
| puuE | 16129263 | NP_415818.1 | *Escherichia coli* |
| abat | 37202121 | NP_766549.2 | *Mus musculus* |
| gabT | 70733692 | YP_257332.1 | *Pseudomonas fluorescens* |
| abat | 47523600 | NP_999428.1 | *Sus scrofa* |

Additional enzyme candidates include putrescine aminotransferases or other diamine aminotransferases. Such enzymes are particularly well suited for carrying out the conversion of 6-aminocaproate semialdehyde to hexamethylenediamine. The *E. coli* putrescine aminotransferase is encoded by the ygjG gene and the purified enzyme also was able to transaminate cadaverine and spermidine (Samsonova et al., *BMC Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonova et al., supra; Kim, K. H., *J Biol Chem* 239:783-786 (1964)). A putrescine aminotransferase with higher activity with pyruvate as the amino acceptor than alpha-ketoglutarate is the spuC gene of *Pseudomonas aeruginosa* (Lu et al., *J Bacteriol* 184:3765-3773 (2002)).

| Gene name | GI# | GenBank Accession # | Organism |
|---|---|---|---|
| ygjG | 145698310 | NP_417544 | *Escherichia coli* |
| spuC | 9946143 | AAG03688 | *Pseudomonas aeruginosa* |

1. Yet additional candidate enzymes include beta-alanine/alpha-ketoglutarate aminotransferases which produce malonate semialdehyde from beta-alanine (WO08027742). The gene product of SkPYD4 in *Saccharomyces kluyveri* was also shown to preferentially use beta-alanine as the amino group donor (Andersen et al., *FEBS. J.* 274:1804-

1817 (2007)). SkUGA1 encodes a homologue of *Saccharomyces cerevisiae* GABA aminotransferase, UGA1 (Ramos et al., *Eur. J. Biochem.*, 149:401-404 (1985)), whereas SkPYD4 encodes an enzyme involved in both β-alanine and GABA transamination (Andersen et al., supra). 3-Amino-2-methylpropionate transaminase catalyzes the transformation from methylmalonate semialdehyde to 3-amino-2-methylpropionate. This enzyme has been characterized in *Rattus norvegicus* and *Sus scrofa* and is encoded by Abat (Tamaki et al, *Methods Enzymol*, 324:376-389 (2000)).

| Gene name | GI# | GenBank Accession # | Organism |
|---|---|---|---|
| SkyPYD4 | 98626772 | ABF58893.1 | *Saccharomyces kluyveri* |
| SkUGA1 | 98626792 | ABF58894.1 | *Saccharomyces kluyveri* |
| UGA1 | 6321456 | NP_011533.1 | *Saccharomyces cerevisiae* |
| Abat | 122065191 | P50554.3 | *Rattus norvegicus* |
| Abat | 120968 | P80147.2 | *Sus scrofa* |

2.8.3.a Coenzyme-A transferase.-CoA transferases catalyze reversible reactions that involve the transfer of a CoA moiety from one molecule to another. For example, step E of FIG. 10 is catalyzed by a 3-oxoadipyl-CoA transferase. In this step, 3-oxoadipate is formed by the transfer of the CoA group from 3-oxoadipyl-CoA to succinate, acetate, or another CoA acceptor. Step E of FIG. 11 entails the transfer of a CoA moiety from another 3-oxoacyl-CoA, 3-oxo-6-aminohexanoyl-CoA. One candidate enzyme for these steps is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272: 25659-25667 (1997)) and *Bacillus subtilis* (Stols et al., *Protein. Expr. Purif.* 53:396-403 (2007)).

| Gene name | GI# | GeneBank Accession # | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

A 3-oxoacyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)).

| Gene name | GI# | Accession # | Organism |
|---|---|---|---|
| atoA | 2492994 | P76459.1 | *Escherichia coli* K12 |
| atoD | 2492990 | P76458.1 | *Escherichia coli* K12 |
| actA | 62391407 | YP_226809.1 | *Corynebacterium glulamicum* ATCC 13032 |
| cg0592 | 62389399 | YP_224801.1 | *Corynebacterium glutamicum* ATCC 13032 |
| ctfA | 15004866 | NP_149326,1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

The above enzymes may also exhibit the desired activities on adipyl-CoA and adipate (FIG. 10, step K) or 6-aminocaproate and 6-aminocaproyl-CoA (FIG. 10, step Q; FIG. 2, step K). Nevertheless, additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J. Biochem.* 212:121-127 (1993); Sohling et al., *J. Bacteriol.* 178:871-880 (1996)).

| Gene name | GI# | GeneBank Accession # | Organism |
|---|---|---|---|
| cat1 | 729048 | P38946.1 | *Clostridium kluyveri* |
| cat2 | 172046066 | P38942.2 | *Ctostridium kluyveri* |
| cat3 | 146349050 | EDK35586.1 | *Clostridium ktuyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)).

| Gene name | GI# | GeneBank Accession # | Organism |
|---|---|---|---|
| gctA | 559392 | CAA57199.1 | *Acidaminococcus fermentans* |
| gctB | 559393 | CAA57200.1 | *Acidaminococcus fermentans* |

3.1.2.a Thiolester hydrolase (CoA specific). Several eukaryotic acetyl-CoA hydrolases have broad substrate specificity and thus represent suitable candidate enzymes for hydrolyzing 3-oxoadipyl-CoA, adipyl-CoA, 3-oxo-6-aminohexanoyl-CoA, or 6-aminocaproyl-CoA (Steps G and M of FIGS. 10 and 11). For example, the enzyme from Rattus norvegicus brain (Robinson et al., Biochem. Biophys. Res. Commun. 71:959-965 (1976)) can react with butyryl-CoA, hexanoyl-CoA and malonyl-CoA.

| Gene name | GI# | GenBank Accession # | Organism |
|---|---|---|---|
| acot12 | 18543355 | NP_570103.1 | Rattus norvegicus |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., J Biol Chem. 269:14248-14253 (1994)). Genes encoding this enzyme include hibch of Rattus norvegicus (Shimomura et al., supra; Shimomura et al., Methods Enzymol. 324:229-240 (2000)) and Homo sapiens (Shimomura et al., supra). Candidate genes by sequence homology include hibch of Saccharomyces cerevisiae and BC 2292 of Bacillus cereus.

| Gene name | GI# | GenBank Accession # | Organism |
|---|---|---|---|
| hibch | 146324906 | Q5XIE6.2 | Rattus norvegicus |
| hibch | 146324905 | Q6NVY1.2 | Homo sapiens |
| hibch | 2506374 | P28817.2 | Saccharomyces cerevisiae |
| BC_2292 | 29895975 | AP09256 | Bacillus cereus |

Yet another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J. BioL Chem. 280:38125-38132 (2005)) and the closest E. coli homolog, tesB, which can also hydrolyze a broad range of CoA thiolesters (Naggert et al., J Biol Chem 266:11044-11050 (1991)). A similar enzyme has also been characterized in the rat liver (Deana R., Biochem Int 26:767-773 (1992)).

| Gene name | GI# | GenBank Accession # | Organism |
|---|---|---|---|
| tesB | 16128437 | NP_414986 | Escherichia coli |
| acot8 | 3191970 | CAA15502 | Homo sapiens |
| acot8 | 51036669 | NP_570112 | Rattus norvegicus |

Other potential E. coli thiolester hydrolases include the gene products of tesA (Bonner et al., J Biol Chem 247:3123-3133 (1972)), ybgC (Kuznetsova et al., FEMS Microbiol Rev 29:263-279 (2005); Zhuang et al., FEBS Lett 516:161-163 (2002)), paaI (Song et al., J Biol Chem 281:11028-11038 (2006)), and ybdB (Leduc et al., J Bacteriol 189:7112-7126 (2007)).

| Gene name | GI# | GenBank Accession # | Organism |
|---|---|---|---|
| tesA | 16128478 | NP_415027 | Escherichia coli |
| ybgC | 16128711 | NP_415264 | Escherichia coli |
| paaI | 16129357 | NP_415914 | Escherichia coli |
| ybdB | 16128580 | NP_415129 | Escherichia coli |

6.3.1.a/6.3.2.a amide synthases/peptide synthases. The direct conversion of 6-aminocaproate to caprolactam (Step S, FIG. 10; Step R, FIG. 11) requires the formation of an intramolecular peptide bond. Ribosomes, which assemble amino acids into proteins during translation, are nature's most abundant peptide bond-forming catalysts. Nonribosomal peptide synthetases are peptide bond forming catalysts that do not involve messenger mRNA (Schwarzer et al., Nat. Prod. Rep. 20:275-287 (2003)). Additional enzymes capable of forming peptide bonds include acyl-CoA synthetase from Pseudomonas chlororaphis (Abe et al., J Biol Chem 283:11312-11321 (2008)), gamma-Glutamylputrescine synthetase from E. coli (Kurihara et al., J Biol Chem 283:19981-19990 (2008)), and beta-lactam synthetase from Streptomyces clavuligerus (Bachmann et al., Proc Natl Acad Sci USA 95:9082-9086 (1998); Bachmann et al., Biochemistry 39:11187-11193 (2000); Miller et al., Nat. Struct. Biol 8:684-689 (2001); Miller et al., Proc Natl Acad Sci USA 99:14752-14757 (2002); Tahlan et al., Antimicrob. Agents. Chemother. 48:930-939 (2004)).

| Gene name | GI# | GenBank Accession # | Organism |
|---|---|---|---|
| acsA | 60650089 | BAD90933 | Pseudomonas chlororaphis |
| puuA | 87081870 | AAC74379 | Escherichia coli |
| bls | 41016784 | Q9R8E3 | Streptomyces clavuligerus |

4.2.1.a Hydrolyase. Most dehydratases catalyze the α,β-elimination of water. This involves activation of the α-hydrogen by an electron-withdrawing carbonyl, carboxylate, or CoA-thiol ester group and removal of the hydroxyl group from the β-position. Enzymes exhibiting activity on substrates with an electron-withdrawing carboxylate group are excellent candidates for dehydrating 3-hydroxyadipate (FIG. 10, Step I) or 3-hydroxy-6-aminohexanoate (FIG. 11, Step I).

For example, fumarase enzymes naturally catalyze the reversible dehydration of malate to fumarate. E. coli has three fumarases: FumA, FumB, and FumC that are regulated by growth conditions. FumB is oxygen sensitive and only active under anaerobic conditions. FumA is active under microaerobic conditions, and FumC is the only active enzyme in aerobic growth (Tseng et al., J Bacteriol 183:461-467 (2001); Woods et al., Biochim Biophys Acta 954:14-26 (1988); Guest et al., J Gen Microbiol 131:2971-2984 (1985)). Additional enzyme candidates are found in Campylobacter jejuni (Smith et al., Int. J Biochem. Cell Biol 31:961-975 (1999)), Thermus thermophilus (Mizobata et al., Arch. Biochem. Biophys. 355:49-55 (1998)) and Rattus norvegicus (Kobayashi et al., J Biochem. 89:1923-1931 (1981)). Similar enzymes with high sequence homology include fumI from Arabidopsis thaliana and fumC from Corynebacterium glutamicum. The MmcBC fumarase from Pelotomaculum thermopropionicum is another class of fumarase with two subunits (Shimoyama et al., FEMS Microbiol Lett 270:207-213 (2007)).

| Gene name | GI# | GeneBank Accession # | Organism |
|---|---|---|---|
| fumA | 81175318 | P0AC33 | Escherichia coli |
| fumB | 33112655 | P14407 | Escherichia coli |
| fumC | 120601 | P05042 | Escherichia coli |
| fumC | 9789756 | O69294 | Campylobacter jejuni |
| fumC | 3062847 | BAA25700 | Thermus thermophilus |
| fumH | 120605 | P14408 | Rattus norvegicus |

| Gene name | GI# | GeneBank Accession # | Organism |
|---|---|---|---|
| fum1 | 39931311 | P93033 | Arabidopsis thaliana |
| fumC | 39931596 | Q8NRN8 | Corynebacterium glutamicum |
| MmcB | 147677691 | YP_001211906 | Pelotomaculum thermopropionicum |
| MmcC | 147677692 | YP_001211907 | Pelotomaculum thermopropionicum |

Two additional dehydratase candidates are 2-(hydroxymethyl)glutarate dehydratase and dimethylmaleate hydratase, enzymes studied for their role in nicontinate catabolism in *Eubacterium barkeri* (formerly *Clostridium barkeri*) (Alhapel et al., *Proc Natl Acad Sci USA* 103:12341-6 (2006)). 2-(Hydroxymethyl)glutarate dehydratase is a [4Fe-4S]-containing enzyme that dehydrates 2-(hydroxymethyl)glutarate to 2-methylene-glutarate. This enzyme is encoded by hmd in *Eubacterium barkeri* (Alhapel et al., supra). Similar enzymes with high sequence homology are found in *Bacteroides capillosus, Anaerotruncus colihominis*, and *Natranaerobius thermophilius*. These enzymes are homologous to the alpha and beta subunits of [4Fe-45]-containing bacterial serine dehydratases (e.g., *E. coli* enzymes encoded by tdcG, sdhB, and sdaA).

| Gene name | GI# | GenBank Accession # | Organism |
|---|---|---|---|
| hmd | 86278275 | ABC88407.1 | Eubacterium barkeri |
| BACCAP_02294 | 154498305 | ZP_02036683.1 | Bacteroides capillosus |
| ANACOL_02527 | 167771169 | ZP_02443222.1 | Anaerotruncus colihominis DSM 17241 |
| NtherDRAFT_2368 | 169192667 | ZP_02852366.1 | Natranaerobius thermophilus JW/NM-WN-LF |

Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel et al., supra; Kollmann-Koch et al., *Hoppe Seylers. Z. Physiol Chem.* 365:847-857 (1984)).

| Gene name | GI# | GenBank Accession # | Organism |
|---|---|---|---|
| dmdA | 86278276 | ABC88408 | Eubacterium barkeri |
| dmdB | 86278277 | ABC88409.1 | Eubacterium barkeri |

An additional enzyme candidate is 2-methylmalate dehydratase, also called citramalate hydrolyase, a reversible hydrolyase that catalyzes the alpha, beta elimination of water from citramalate to form mesaconate. This enzyme has been purified and characterized in *Clostridium tetanomorphum* (Wang et al., *J. BioL Chem.* 244:2516-2526 (1969)). The activity of this enzyme has also been detected in several bacteria in the genera *Citrobacter* and *Morganella* in the context of the glutamate degradation VI pathway (Kato et al., *Arch. Microbiol* 168:457-463 (1997)). Genes encoding this enzyme have not been identified in any organism to date.

Enzymes exhibiting activity on substrates with an electron-withdrawing CoA-thiol ester group adjacent to the α-hydrogen are excellent candidates for dehydrating 3-hydroxyadipyl-CoA (FIG. 10, Step C) or 3-hydroxy-6-aminohexanoyl-CoA (FIG. 11, Step C). The enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)). The paaA and paaB from *P. fluorescens* catalyze analogous transformations (Olivera et al., *Proc. Natl. Acad. Sci. USA* 95:6419-6424 (1998)). Lastly, a number of *Escherichia coli* genes have been shown to demonstrate enoyl-CoA hydratase functionality including maoC (Park et al., *J. Bacteriol.* 185:5391-5397 (2003)), paaF (Ismail et al., supra; Park et al., *Appl. Biochem. Biotechnol* 113-116: 335-346 (2004); Park et al., *Biotechnol Bioeng* 86:681-686 (2004)) and paaG (Ismail et al., supra; Park et al., *Appl. Biochem. Biotechnol* 113-116:335-346 (2004); Park et al., *Biotechnol Bioeng* 86:681-686 (2004)). Crotonase enzymes are additional candidates for dehydrating the required 3-hydroxyacyl-CoA molecules depicted in FIGS. 10 and 11. These enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus, Acidianus*, and *Metallosphaera*. Exemplary genes encoding crotonase enzymes can be found in *C. acetobutylicum* (Boynton et al., supra), *C. kluyveri* (Hillmer et al., *FEBS Lett.* 21:351-354 (1972)), and *Metallosphaera sedula* (Berg et al., supra) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Roberts et al., *Arch. Microbiol* 117:99-108 (1978); Agnihotri et al., *Bioorg. Med. Chem.* 11:9-20 (2003); Conrad et al., *J Bacteriol.* 118:103-111 (1974)).

| Gene name | GI# | GenBank Accession # | Organism |
|---|---|---|---|
| paaA | 26990002 | NP_745427.1 | Pseudomonas fluorescens |
| paaB | 26990001 | NP_745426.1 | Pseudomonas fluorescens |
| phaA | 106636093 | ABF82233.1 | Pseudomonas putida |
| phaB | 106636094 | ABF82234.1 | Pseudomonas putida |
| maoC | 16129348 | NP_415905.1 | Escherichia coli |
| paaF | 16129354 | NP_415911.1 | Escherichia coli |
| paaG | 16129355 | NP_415912.1 | Escherichia coli |
| crt | 15895969 | NP_349318.1 | Clostridium acetobutylicum |
| crt1 | 153953091 | YP_001393856 | Clostridium kluyveri DSM 555 |

6.2.1.a Acid-thiol ligase. Steps F, L, and R of FIG. 10 and Steps F and L of FIG. 11 require acid-thiol ligase or synthetase functionality (the terms ligase, synthetase, and synthase are used herein interchangeably and refer to the same enzyme class). Exemplary genes encoding enzymes likely to carry out these transformations include the sucCD genes of *E. coli* which naturally form a succinyl-CoA synthetase complex. This enzyme complex naturally catalyzes the formation of succinyl-CoA from succinate with the concaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA.

| Gene name | GI# | GenBank Accession # | Organism |
|---|---|---|---|
| sucC | 16128703 | NP_415256.1 | Escherichia coli |
| sucD | 1786949 | AAC73823.1 | Escherichia coli |

Additional exemplary CoA-ligases include the rat dicarboxylate-CoA ligase for which the sequence is yet uncharacterized (Vamecq et al., Biochemical Journal 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178(14):4122-4130 (1996)). Additional candidate enzymes are acetoacetyl-CoA synthetases from Mus musculus (Hasegawa et al., Biochim Biophys Acta 1779:414-419 (2008)) and Homo sapiens (Ohgami et al., Biochem Pharmacol 65:989-994 (2003)) which naturally catalyze the ATP-dependant conversion of acetoacetate into acetoacetyl-CoA.

| Gene name | GI | GenBank Accession # | Organism |
|---|---|---|---|
| phl | 77019264 | CAJ15517.1 | Penicillium chrysogenum |
| phlB | 152002983 | ABS19624.1 | Penicillium chrysogenum |
| paaF | 22711873 | AAC24333.2 | Pseudomonas putida |
| bioW | 50812281 | NP_390902.2 | Bacillus subtilis |
| AACS | 21313520 | NP_084486.1 | Mus musculus |
| AACS | 31982927 | NP_0764172 | Homo sapiens |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from Archaeoglobus fulgidus, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., J Bacteriol 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen et al., Arch Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen et al., supra). The enzymes from A. fulgidus, H. marismortui and P. aerophilum have all been cloned, functionally expressed, and characterized in E. coli (Musfeldt et al., supra; Brasen et al., supra).

| Gene name | GI | GenBank Accession # | Organism |
|---|---|---|---|
| AF1211 | 11498810 | NP_070039.1 | Archaeoglobus fulgidus DSM 4304 |
| scs | 55377722 | YP_135572.1 | Haloarcula marismortui ATCC 43049 |
| PAE3250 | 18313937 | NP_560604.1 | Pyrobaculum aerophilum str. IM2 |

Yet another option is to employ a set of enzymes with net ligase or synthetase activity. For example, phosphotransadipylase and adipate kinase enzymes are catalyzed by the gene products of buk1, buk2, and ptb from C. acetobutylicum (Walter et al., Gene 134:107-111 (1993); Huang et al., J. Mol. Microbiol. Biotechnol. 2:33-38 (2000)). The ptb gene encodes an enzyme that can convert butyryl-CoA into butyryl-phosphate, which is then converted to butyrate via either of the buk gene products with the concomitant generation of ATP.

| Gene name | GI# | GenBank Accession # | Organism |
|---|---|---|---|
| ptb | 15896327 | NP_349676 | Clostridium acetobutylicum |
| buk1 | 15896326 | NP_349675 | Clostridium acetobutylicum |
| buk2 | 20137415 | Q97II1 | Clostridium acetobutylicum |

No enzyme required—Spontaneous cyclization. 6-Aminocaproyl-CoA will cyclize spontaneously to caprolactam, thus eliminating the need for a dedicated enzyme for this step. A similar spontaneous cyclization is observed with 4-aminobutyryl-CoA which forms pyrrolidinone (Ohsugi et al., J Biol Chem 256:7642-7651 (1981)).

Microbiol organisms may also be generated that are capable of producing hexamethylenediamine from acetyl-CoA and succinyl-CoA and as shown in FIG. 10 that starts from acetyl-CoA and succinyl-CoA. E. coli provides a good host for generating a non-naturally occurring microorganism capable of producing hexamethylenediamine. While E. coli may be used to describe this pathway, it should be understood that any microorganism can be adapted to generate such pathway. To generate an E. coli strain engineered to produce hexamethylenediamine, nucleic acids encoding the requisite enzymes are expressed in E. coli using well known molecular biology techniques (see, for example, Sambrook, supra, 2001; Ausubel, supra, 1999). In particular, the paaJ (NP-415915.1), paaH (NP-415913.1), and maoC (NP-415905.1) genes encoding the 3-oxoadipyl-CoA thiolase, 3-oxoadipyl-CoA reductase, and 3-hydroxyadipyl-CoA dehydratase activities, respectively, are cloned into the pZE13 vector (Expressys, Ruelzheim, Germany) under the PA1/lacO promoter. In addition, the bcd (NP-349317.1) and eftAB (NP-349315.1 and NP-349316.1) genes encoding 5-carboxy-2-pentenoyl-CoA reductase activity are cloned into the pZA33 vector (Expressys, Ruelzheim, Germany) under the PA1/lacO promoter. Lastly, the acrI (YP-047869.1), gabT (NP-417148.1), bioW (NP-390902.2), and ygjG (NP-417544) genes encoding adipyl-CoA reductase (aldehyde forming), 6-aminocaproyl-CoA reductase (aldehyde forming), 6-aminocaproic acid transaminase, 6-aminocaproyl-CoA synthase, and hexamethylenediamine transaminase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for hexamethylenediamine synthesis.

In other examples, hexamethylenediamine can be produced via a pathway for converting acetyl-CoA and 4-aminobutyryl-CoA to 6-Aminocaproyl-CoA Another pathway to produce hexamethylenediamine is from acetyl-CoA and 4-aminobutyryl-CoA.

The paaJ (NP-415915.1), paaH (NP-415913.1), and maoC (NP-415905.1) genes encoding the 3-oxo-6-aminohexanoyl-CoA thiolase, 3-oxo-6-aminohexanoyl-CoA reductase, 3-hydroxy-6-aminohexanoyl-CoA dehydratase activities, respectively, can be cloned into the pZE13 vector (Expressys, Ruelzheim, Germany) under the PA1/lacO promoter. In addition, the bcd (NP-349317.1), etfAB (NP-349315.1 and NP-349316.1), acrI (YP-047869.1), and ygjG (NP-417544) genes encoding 6-aminohex-2-enoyl-CoA reductase, 6-aminocaproyl-CoA reductase (aldehyde forming), and hexamethylenediamine transaminase activities are cloned into the pZA33 vector (Expressys, Ruelzheim, Germany) under the PA1/lacO promoter. Lastly, the sucD (NP-904963.1), gabT (NP-417148.1), and cat2 (P38942.2) genes encoding succinyl-CoA reductase (aldehyde forming), GABA transaminase, and 4-aminobutyryl-CoA/acyl-CoA transferase activities are cloned into a third compatible plasmid, pZS23, under the PA1/lacO promoter, to increase the availability of 4-aminobutyryl-CoA. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for hexamethylenediamine synthesis.

Hexamethylenediamine may also be produced from 6-Aminocaproate (6-ACA). This pathway involves activation of the acid group by phosphorylation and/or acylation. Acetylation of the terminal amino group provides protection from spontaneous cyclization of pathway intermediates.

Several pathways for producing HMD from 6-aminocaproate are detailed in FIG. 13. All routes entail activation of the carboxylic acid group, followed by reduction and transamination. In three routes, 6-aminocaproate is activated directly while in other routes, the terminal amine group is protected by N-acetylation to prevent spontaneous cyclization.

In one route, 6-aminocaproate is phosphorylated to 6-AHOP by 6-aminocaproate kinase (FIG. 13, Step A). 6-AHOP is then reduced to 6-aminocaproic semialdehyde (FIG. 13, Step B) and subsequently transaminated (FIG. 13, Step C) by an aminotransferase or an aminating oxidoreductase.

Alternately, 6-AHOP is converted to 6-aminocaproyl-CoA by an acyltransferase (FIG. 13, Step L). 6-Aminocaproyl-CoA is then reduced to 6-aminocaproic semialdehyde by a CoA-dependent aldehyde dehydrogenase (FIG. 13, Step N). HMD is then formed by transamination of 6-aminocaproic semialdehyde by an aminotransferase or aminating oxidoreductase (FIG. 13, Step C).

In yet another route, 6-aminocaproate is first activated to a CoA derivative by a CoA transferase or CoA ligase (FIG. 13, Step M). The product, 6-aminocaproyl-CoA, may spontaneously cyclize, or be converted to 6-aminocaproic semialdehyde by an aldehyde-forming CoA-dependent aldehyde dehydrogenase (FIG. 13, Step N). 6-Aminocaproic semialdehyde is converted to HMD by an aminotransferase or an aminating oxidoreductase (FIG. 13, Step C).

Additional routes proceed from 6-acetamidohexanoate, the acetylated product of 6-aminocaproate N-acetyltransferase. 6-Acetamidohexanoate is converted to 6-acetamidohexanal by different routes (described below). In the final two steps of these routes, 6-acetamidohexanal is first converted to 6-acetamidohexanamine by an aminotransferase or an aminating oxidoreductase (FIG. 13, Step G). 6-Acetamidohexanamine is subsequently converted to HMD by an amide hydrolase or an N-acetyltransferase (FIG. 13, Step H).

In one route, 6-acetamidohexanoate is phosphorylated by 6-acetamidohexanoate kinase (FIG. 13, Step E). The product, 6-AAHOP, is reduced to form 6-acetamidohexanal (FIG. 13, Step F), which is then converted to HMD as described above.

In another route, 6-acetamidohexanoate is activated to 6-acetamidohexanoyl-CoA by a CoA transferase or CoA ligase (FIG. 13, Step I). The CoA derivative is then reduced to 6-acetamidohexanal by an aldehyde-forming CoA-dependent oxidoreductase (FIG. 13, Step J). 6-acetamidohexanal is then converted to HMD as described above.

Alternately, 6-acetamidohexanoate is phosphorylated to 6-AAHOP (FIG. 13, Step E) and subsequently converted to 6-acetamidohexanoyl-CoA by an acyltransferase (FIG. 13, Step K). 6-Acetamidohexanoyl-CoA is then reduced to HMD as described previously.

The transformations depicted in FIGS. 12 and 13 fall into the general categories of transformations shown in Table 9. Below is described a number of biochemically characterized genes in each category. Specifically listed are genes that can be applied to catalyze the appropriate transformations in FIGS. 12-13 when properly cloned and expressed.

Table 9 shows the enzyme types useful to convert common central metabolic intermediates into 6-aminocaproate and hexamethylenediamine. The first three digits of each label correspond to the first three Enzyme Commission number digits which denote the general type of transformation independent of substrate specificity.

TABLE 9

| LABEL | FUNCTION |
|---|---|
| 1.2.1.b | Oxidoreductase (acyl-CoA to aldehyde) |
| 1.2.1.c | Oxidoreductase (2-ketoacid to acyl-CoA) |
| 1.2.1.d | Oxidoreductase (phosphonic acid to aldehyde) |
| 1.3.1.a | Oxidoreductase (alkene to alkane) |
| 1.4.1.a | Oxidoreductase (ketone or aldehyde to amino) |
| 2.3.1.a | Acyltransferase (transferring CoA to phospho) |
| 2.3.1.c | Acyltransferase (N-acetyltransferase) |
| 2.3.1.d | Acyltransferase (formate C-acyltransferase) |
| 2.6.1.a | Aminotransferase |
| 2.7.2.a | Phosphotransferase (carboxy acceptor) |
| 2.8.3.a | Coenzyme-A transferase |
| 3.5.1.a | Hydrolase (acting on linear amides) |
| 4.1.1.a | Carboxy-lyase |
| 4.1.2.a | Aldehyde-lyase |
| 4.2.1.a | Hydro-lyase |
| 6.2.1.a | Acid-thiol ligase |

1.2.1.b Oxidoreductase (acyl-CoA to aldehyde). The transformations of 6-acetamidohexanoyl-CoA to 6-acetamidohexanal (FIG. 13, Step J) and 6-aminocaproyl-CoA to 6-aminocaproic semialdehyde (FIG. 13, Step N) are catalyzed by CoA-dependent oxidoreductase enzyme in the EC class 1.2.1. Adipyl-CoA is converted to adipate semialdehyde by adipyl-CoA oxidoreductase, an enzyme with similar functionality (FIG. 12, Step O). Succinic semialdehyde dehydrogenase, an enzyme that forms FIG. 12 precursor succinic semialdehyde from succinyl-CoA, is also a CoA-dependent oxidoreductase. Oxidoreductases in the EC class 1.2.1.—are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *Journal of Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinic semialdehyde dehydrogenase encoded by the sucD gene in *Clostridium kluyveri* (Sohling and Gottschalk, *J. Bacteriol.* 178:871-880 (1996)). SucD of *P. gingivalis* is another succinic semialdehyde dehydrogenase (Takahashi et al., *J. Bacteriol.* 182:4704-4710 (2000)). The acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:43-55 (1972); and Koo et al., *Biotechnol Lett.* 27:505-510 (2005)).

| Gene name | GI# | GenBank Accession # | Organism |
|---|---|---|---|
| acr1 | 50086359 | YP_047869.1 | *Acinetobacter calcoaceticus* |
| acr1 | 1684886 | AAC45217 | *Acinetobacter baylyi* |
| acr1 | 18857901 | BAB85476.1 | *Acinetobacter* sp. Strain M-1 |
| sucD | 172046062 | P38947.1 | *Clostridium kluyveri* |
| sucD | 34540484 | NP_904963.1 | *Porphyromonas gingivalis* |
| bphG | 425213 | BAA03892.1 | *Pseudomonas* sp |
| adhE | 55818563 | AAV66076.1 | *Leuconostoc mesenteroides* |

An additional enzyme that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); and Thauer, R. K., *Science.* 318:1732-1733 (2007)). The enzyme utilizes NADPH as a cofactor and has been characterized in Metallosphaera and *Sulfolobus* sp (Alber et al., *J. Bacteriol.* 188:8551-8559 (2006); and Hugler et al., *J. Bacteriol.* 184:2404-2410 (2002)). The enzyme is encoded by Msed_0709 in Metallosphaera sedula (Alber et al., *J. Bacteriol.* 188:8551-8559 (2006); and Berg et al., *Science.* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WIPO Patent Application WO/2007/141208 Kind Code: A2). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl Environ Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., *Appl Environ Microbiol* 65:4973-4980 (1999)).

| Gene name | GI# | GenBank Accession # | Organism |
|---|---|---|---|
| Msed_0709 | 146303492 | YP_001190808.1 | *Metallosphaera sedula* |
| mcr | 15922498 | NP_378167.1 | *Sulfolobus tokodaii* |
| asd-2 | 15898958 | NP_343563.1 | *Sulfolobus solfataricus* |
| Saci_2370 | 70608071 | YP_256941.1 | *Sulfolobus acidocaldarius* |
| Ald | 49473535 | AAT66436 | *Clostridium beijerinckii* |
| eutE | 687645 | AAA80209 | *Salmonella typhimurium* |
| eutE | 2498347 | P77445 | *Escherichia coli* |

1.2.1.c Oxidoreductase (2-ketoacid to acyl-CoA). Several transformations in FIG. 12 require conversion of a 2-ketoacid to an acyl-CoA (Steps L, P and Q) by an enzyme in the EC class 1.2.1. Such reactions are catalyzed by multi-enzyme complexes that catalyze a series of partial reactions which result in acylating oxidative decarboxylation of 2-keto-acids. Exemplary enzymes include 1) branched-chain 2-keto-acid dehydrogenase, 2) alpha-ketoglutarate dehydrogenase, and 3) the pyruvate dehydrogenase multi-enzyme complex (PDHC). Each of the 2-keto-acid dehydrogenase complexes occupies key positions in intermediary metabolism, and enzyme activity is typically tightly regulated (Fries et al., *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (i.e. larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al., Appl. Environ. Microbiol. 73:1766-1771 (2007); Kim et al., J. Bacteriol. 190: 3851-3858 (2008); and Zhou et al., Biotechnol. Lett. 30:335-342 (2008)). For example, the inhibitory effect of NADH can be overcome by engineering an H322Y mutation in the E3 component (Kim et al., J. Bacteriol. 190:3851-3858 (2008)). Structural studies of individual components and how they work together in complex provide insight into the catalytic mechanisms and architecture of enzymes in this family (Aevarsson et al., Nat. Struct. Biol. 6:785-792 (1999); and Zhou et al., Proc. Natl. Acad. Sci. U.S. A 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, Curr. Top. Bioenerg. 10:217-278 (1980)). Encoded by genes sucA, sucB and lpd in *E. coli*, AKGD gene expression is downregulated under anaerobic conditions and during growth on glucose (Park et al., Mol. Microbiol. 15:473-482 (1995)). Although the substrate range of AKGD is narrow, structural studies of the catalytic core of the E2 component pinpoint specific residues responsible for substrate specificity (Knapp et al., J. Mol. Biol. 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al., Mol. Gen. Genet. 234:285-296 (1992)). In yeast, the LPD1 gene encoding the E3 component is regulated at the transcriptional level by glucose (Roy and Dawes, J. Gen. Microbiol. 133:925-933 (1987)). The E1 component, encoded by KGD1, is also regulated by glucose and activated by the products of HAP2 and HAP3 (Repetto and Tzagoloff, Mol. Cell. Biol. 9:2695-2705 (1989)). The AKGD enzyme complex, inhibited by products NADH and succinyl-CoA, is well-studied in mammalian systems, as impaired function of has been linked to several neurological diseases (Tretter and dam-Vizi, Philos. Trans. R. Soc. Lond B Biol. Sci. 360:2335-2345 (2005)).

| Gene name | GI# | GenBank Accession # | Organism |
|---|---|---|---|
| sucA | 16128701 | NP_415254.1 | Escherichia coli |
| sucB | 16128702 | NP_415255.1 | Escherichia coli |
| lpd | 16128109 | NP_414658.1 | Escherichia coli |
| odhA | 51704265 | P23129.2 | Bacillus subtilis |
| odhB | 129041 | P16263.1 | Bacillus subtilis |
| pdhD | 118672 | P21880.1 | Bacillus subtilis |
| KGD1 | 6322066 | NP_012141.1 | Saccharomyces cerevisiae |
| KGD2 | 6320352 | NP_010432.1 | Saccharomyces cerevisiae |
| LPD1 | 14318501 | NP_116635.1 | Saccharomyces cerevisiae |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al., Eur. J. Biochem. 213:1091-1099 (1993)), *Rattus norvegicus* (Namba et al., J. Biol. Chem. 244:4437-4447 (1969)) and *Pseudomonas putida* (Sokatch et al., J. Bacteriol. 148:647-652 (1981)). In *Bacillus subtilis* the enzyme is encoded by genes pdhD (E3 component), bfmBB (E2 component), bfmBAA and bfmBAB (E1 component) (Wang et al., Eur. J. Biochem. 213:1091-1099 (1993)). In mammals, the complex is regulated by phosphorylation by specific phosphatases and protein kinases. The complex has been studied in rat hepatocites (Chicco et al., J. Biol. Chem. 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al., Nat. Struct. Biol. 6:785-792 (1999); and Mattevi et al., Science. 255:1544-1550 (1992)) and the enzyme complex has been studied (Sokatch et al., J. Bacteriol. 148:647-652 (1981)). Transcription of the *P. putida* BCKAD genes is activated by the gene product of bkdR (Hesslinger et al., Mol. Microbiol. 27:477-492 (1998)). In some organisms including *Rattus l norvegicus* (Paxton et al., Biochem. J. 234:295-303 (1986)) and *Saccharomyces cerevisiae* (Sinclair et al., Biochem. Mol. Biol. int. 31: 911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, Biochemistry. 33:12879-12885 (1994)).

| Gene name | GI# | GenBank Accession # | Organism |
|---|---|---|---|
| bfmBB | 16079459 | NP_390283.1 | Bacillus subtilis |
| bfmBAA | 16079461 | NP_390285.1 | Bacillus subtilis |
| bfmBAB | 16079460 | NP_390284.1 | Bacillus subtilis |
| pdhD | 118672 | P21880.1 | Bacillus subtilis |
| lpdV | 118677 | P09063.1 | Pseudomonas putida |
| bkdB | 129044 | P09062.1 | Pseudomonas putida |
| bkdA1 | 26991090 | NP_746515.1 | Pseudomonas putida |
| bkdA2 | 26991091 | NP_746516.1 | Pseudomonas putida |
| Bckdha | 77736548 | NP_036914.1 | Rattus norvegicus |
| Bckdhb | 158749538 | NP_062140.1 | Rattus norvegicus |
| Dbt | 158749632 | NP_445764.1 | Rattus norvegicus |
| Dld | 40786469 | NP_955417.1 | Rattus norvegicus |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, J Biol Chem. 256:815-822 (1981); Bremer, Eur. J Biochem. 8:535-540 (1969); and Gong et al., J Biol Chem. 275:13645-13653 (2000)). As mentioned previously, enzyme engineering efforts have improved the *E. coli* PDH enzyme activity under anaerobic conditions (Kim et al., Appl. Environ. Microbiol. 73:1766-1771 (2007); Kim et al., J. Bacteriol. 190:3851-3858 (2008)); and Zhou et al., Biotechnol. Lett. 30:335-342 (2008)). In contrast to the *E. coli* PDH, the *B. subtilis* complex is active and required for growth under anaerobic conditions (Nakano et al., J. Bacteriol. 179:6749-6755 (1997)). The *Klebsiella pneumoniae* PDH, characterized during growth on glycerol, is also active under anaerobic conditions (Menzel et al., J. Biotechnol. 56:135-142 (1997)). Crystal structures of the enzyme complex from bovine kidney (Zhou et al., Proc. Natl. Acad. Sci. U.S. A 98:14802-14807 (2001)) and the E2 catalytic domain from *Azotobacter vinelandii* are available (Mattevi et al., Science. 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al., Biochem. J. 234:295-303 (19861.

| Gene name | GI# | GenBank Accession # | Organism |
|---|---|---|---|
| aceE | 16128107 | NP_414656.1 | Escherichia coli |
| aceF | 16128108 | NP_414657.1 | Escherichia coli |
| lpd | 16128109 | NP_414658.1 | Escherichia coli |
| pdhA | 3123238 | P21881.1 | Bacillus subtilis |
| pdhB | 129068 | P21882.1 | Bacillus subtilis |
| pdhC | 129054 | P21883.2 | Bacillus subtilis |
| pdhD | 118672 | P21880.1 | Bacillus subtilis |
| ace | 152968699 | YP_001333808.1 | Klebsiella pneumonia |
| aceF | 152968700 | YP_001333809.1 | Klebsiella pneumonia |
| lpdA | 152968701 | YP_001333810.1 | Klebsiella pneumonia |
| Pdha1 | 124430510 | NP_001004072.2 | Rattus norvegicus |
| Pdha2 | 16758900 | NP_446446.1 | Rattus norvegicus |
| Dlat | 78365255 | NP_112287.1 | Rattus norvegicus |
| Dld | 40786469 | NP_955417.1 | Rattus norvegicus |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodoxin as electron acceptors in lieu of NAD(P)H. While most enzymes in this family are specific to pyruvate as a substrate (POR) some 2-keto-acid:ferredoxin oxidoreductases have been shown to accept a broad range of 2-ketoacids as substrates including alpha-ketoglutarate and 2-oxobutanoate (Fukuda and Wakagi, *Biochim. Biophys. Acta* 1597:74-80 (2002); and Zhang et al., *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi, *Biochim. Biophys. Acta* 1597:74-80 (2002); and Zhang et al., *J. Biochem.* 120:587-599 (1996)). A plasmid-based expression system has been developed for efficiently expressing this protein in *E. coli* (Fukuda et al., *Eur. J. Biochem.* 268:5639-5646 (2001)) and residues involved in substrate specificity were determined (Fukuda and Wakagi, *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al., *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi, *Biochim. Biophys. Acta* 1597:74-80 (2002)). This class of enzyme is also interesting from an energetic standpoint, as reduced ferredoxin could be used to generate NADH by ferredoxin-NAD reductase (Petitdemange et al., *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment.

| Gene name | GI# | GenBank Accession # | Organism |
|---|---|---|---|
| ST2300 | 15922633 | NP_378302.1 | *Sulfolobus tokodaii* 7 |

1.2.1.d Oxidoreductase (phosphonic acid to aldehyde). The reduction of a phosphonic acid to its corresponding aldehyde is catalyzed by an oxidoreductase in the EC class 1.2.1. Steps B and F in FIG. 13 require such an enzyme for the reduction of 6-AHOP and 6-AAHOP to their corresponding aldehydes. These reactions are not catalyzed by known enzymes, but a similar reaction is catalyzed by aspartate semialdehyde dehydrogenase (ASD, EC 1.2.1.11): the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J. Mol. Biol.* 289:991-1002 (1999)) and the enzyme has been shown to accept the alternate substrate beta-3-methylaspartyl phosphate (Shames et al., *J. Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); and Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly and Devine, Microbiology 140 (Pt 5):1023-1025 (1994)) and other organisms.

| Gene name | GI# | GenBank Accession # | Organism |
|---|---|---|---|
| Asd | 16131307 | NP_417891.1 | *Escherichia coli* |
| Asd | 68249223 | YP_248335.1 | *Haemophilus influenzae* |
| Asd | 1899206 | AAB49996 | *Mycobacterium tuberculosis* |
| VC2036 | 15642038 | NP_231670 | *Vibrio cholera* |
| Asd | 210135348 | YP_002301787.1 | *Heliobacter pylori* |
| ARG5,6 | 6320913 | NP_010992.1 | *Saccharomyces cerevisiae* |
| argC | 16078184 | NP_389001.1 | *Bacillus subtilis* |

1.3.1.a Oxidoreductase (alkene to alkane). Several transformations fall into the category of oxidoreductases that reduce an alkene to an alkane (EC 1.3.1.-). For example, Steps C, G, K and N in FIG. 12, catalyzed by OHED reductase, 6-OHE reductase, 2-AHE reductase and 2,3-dehydroadipyl-CoA reductase, respectively, fall into this category. Enone reductase, alkenal reductase, and enoate reductase enzymes are suitable enzyme candidates for catalyzing the transformations of Steps C, G and K. Enoyl-CoA reductase enzymes catalyze the conversion of 2,3-dehydroadipyl-CoA to adipyl-CoA (Step N).

Enzymes with enone reductase activity have been identified in prokaryotes, eukaryotes and plants (Shimoda et al., Bulletin of the chemical Society of Japan 77:2269-2 (2004); and Wanner and Tressl, *Eur. J Biochem.* 255:271-278 (1998)). Two enone reductases from the cytosolic fraction of *Saccharomyces cerevisiae* were purified and characterized, and found to accept a variety of alkenals (similar to 6-OHE) and enoyl ketones (similar to OHED) as substrates (Wanner and Tressl, *Eur. J Biochem.* 255:271-278 (1998)). Genes encoding these enzymes have not been identified to date. Cell extracts of cyanobacterium *Synechococcus* sp. PCC7942 reduced a variety enone substrates to their corresponding alkyl ketones (Shimoda et al., Bulletin of the chemical Society of Japan 77:2269-2 (2004)). Genes have not been associated with this activity in this organism. Enone reductases in other organisms can also catalyze this transformation.

A recombinant NADPH-dependent enone reductase from *Nicotiana tabacum*, encoded by NtRed1, was functionally expressed and characterized in *E. coli* (Matsushima et al., Bioorganic Chemistry 36:23-28 (2008)). This reductase was functional on the exocyclic enoyl ketone pulegone (Matsushima et al., Bioorganic Chemistry 36:23-28 (2008)). An enzyme candidate in *S. cerevisiae* at the locus YML131W, bears 30% identity to NtRed1(evalue=1e-26). The amino acid sequence of NtRed1 shares significant homology with 2-alkenal reductase from *Arabidopsis thaliana*, zeta-crystallin homolog from *A. thaliana*, pulegone reductase from *Menthe piperita* and phenylpropenal alkene reductase from *Pinus taeda*. These enzymes are known to catalyze the reduction of alkenes of α,β-unsaturated ketones and aldehydes.

Another candidate enoate reductase is 3-oxoadipate oxidoreductase (maleylacetate reductase), an enzyme catalyzing the reduction of 2-maleylacetate (4-oxohex-2-enedioate) to 3-oxoadipate. The enzyme activity was identified and characterized in *Pseudomonas* sp. strain B13 (Kaschabek and Reineke, *J. Bacteriol.* 177:320-325 (1995); and Kaschabek. and Reineke, *J. Bacteriol.* 175:6075-6081 (1993)), and the coding gene was cloned and sequenced (Kasberg et al., *J. Bacteriol.* 179:3801-3803 (1997)). Candidate genes for 3-oxoadipate oxidoreductase include cicE gene from *Pseudomonas* sp. strain B13 (Kasberg et al., *J. Bacteriol.* 179:3801-3803 (1997)), macA gene from *Rhodococcus opacus* (Seibert et al., *J. Bacteriol.* 180:3503-3508

| Gene name | GI# | GenBank Accession # | Organism |
|---|---|---|---|
| NtRed1 | 6692816 | BAA89423 | *Nicotiana tabacum* |
| YML131W | 45269874 | AAS56318.1 | *Saccharomyces cerevisiae* |
| AtDBR1 | 15237888 | NP-197199 | *Arabidopsis thaliana* |
| P2 | 886430 | CAA89262 | *Arabidopsis thaliana* |
| PulR | 34559418 | AAQ75423 | *Menthe piperita* |
| PtPPDBR | 110816011 | ABG91753 | *Pinus taeda* |

2-Alkenal reductase catalyzes the reduction of α,β-unsaturated double bonds of aldehydes and ketones. A barley alkenal hydrogenase ALH1 was identified with activity for a range of α,β-unsaturated ketones and aldehydes including trans-2-nonenal, 2-hexenal, traumatin and 1-octene-3-one (Hambraeus and Nyberg, *J Agric. Food Chem.* 53:8714-8721 (2005)). The *Hordeum vulgare* ALH1 cDNA was cloned expressed in *E. coli* (Hambraeus and Nyberg, *J Agric. Food Chem.* 53:8714-8721 (2005)).

(1998)), and macA gene from *Ralstonia eutropha* (also known as *Cupriavidus necator*) (Seibert et al., *Microbiology* 150:463-472 (2004)).

| Gene name | GI# | GenBank Accession # | Organism |
|---|---|---|---|
| clcE | 3913241 | O30847.1 | *Pseudomonas* sp. strain B13 |
| macA | 7387876 | O84992.1 | *Rhodococcus opacus* |
| macA | 5916089 | AAD55886 | *Cupriavidus necator* |

| Gene name | GI# | GenBank Accession # | Organism |
|---|---|---|---|
| ALH1 | 62765876 | AAX99161 | *Hordeum vulgare* |
| ALH1 | 195652571 | ACG45753 | *Zea mays* |

2-Enoate reductase enzymes are known to catalyze the NAD(P)H-dependent reduction of a wide variety of α,β-unsaturated carboxylic acids and aldehydes (Rohdich et al., *J. Biol. Chem.* 276:5779-5787 (2001)). In the recently published genome sequence of *C. kluyveri*, 9 coding sequences for enoate reductases were reported, out of which one has been characterized (Seedorf et al., *Proc. Natl. Acad. Sci U.S. A* 105:2128-2133 (2008)). The enr genes from both *C. tyrobutyricum* and *M. thermoaceticum* have been cloned and sequenced and show 59% identity to each other. The former gene is also found to have approximately 75% similarity to the characterized gene in *C. kluyveri* (Giesel and Simon, *Arch. Microbiol* 135:51-57 (1983)). It has been reported based on these sequence results that enr is very similar to the dienoyl CoA reductase in E coil (fadH) (Rohdich et al., *J. Biol. Chem.* 276:5779-5787 (2001)). The *C. thermoaceticum* enr gene has also been expressed in a catalytically active form in *E. coli* (Rohdich et al., *J. Biol. Chem.* 276:5779-5787 (2001)).

Enoyl-CoA reductase enzymes are suitable enzymes for catalyzing the reduction of 2,3-dehydroadipyl-CoA to adipyl-CoA (FIG. 12, Step N). One exemplary enoyl-CoA reductase is the gene product of bcd from *C. acetobutylicum* (Atsumi et al., *Metab Eng* 10:305-311 (2008); and Boynton et al., *J. Bacteriol.* 178:3015-3024 (1996)), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli* resulting in an active enzyme (Hoffmeister et al., *J Biol. Chem.* 280:4329-4338 (2005)). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin, *Febs Letters* 581:1561-1566 (2007)).

| Gene name | GI# | GenBank Accession # | Organism |
|---|---|---|---|
| Enr | 169405742 | ACA54153.1 | *Clostridium botulinum* A3 str |
| Enr | 2765041 | CAA71086.1 | *Clostridium tyrobutyricum* |
| Enr | 3402834 | CAA76083.1 | *Clostridium kluyveri* |
| Enr | 83590886 | YP_430895.1 | *Moorella thermoacetica* |
| fadH | 16130976 | NP_417552.1 | *Escherichia coli* |

| Gene name | GI# | Accession # | Organism |
|---|---|---|---|
| Bcd | 15895968 | NP_349317.1 | *Clostridium acetobutylicum* |
| etfA | 15895966 | NP_349315.1 | *Clostridium acetobutylicum* |
| etfB | 15895967 | NP_349316.1 | *Clostridium acetobutylicum* |
| TER | 62287512 | Q5EU90.1 | *Euglena gracilis* |
| TDE0597 | 42526113 | NP_971211.1 | *Treponema denticola* |

Additional enoyl-CoA reductase enzyme candidates are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison and Harwood, Microbiology 151:727-736 (2005)). The genome of nitrogen-fixing soybean symbiont *Bradyrhizobium japonicum* also contains a pim operon composed of genes with high sequence similarity to pimC and pimD of *R. palustris* (Harrison and Harwood, *Microbiology* 151:727-736 (2005)).

| Gene name | GI# | GenBank Accession # | Organism |
|---|---|---|---|
| pimC | 39650632 | CAE29155 | Rhodopseudomonas palustris |
| pimD | 39650631 | CAE29154 | Rhodopseudomonas palustris |
| pimC | 27356102 | BAC53083 | Bradyrhizobium japonicum |
| pimD | 27356101 | BAC53082 | Bradyrhizobium japonicum |

An additional candidate is 2-methyl-branched chain enoyl-CoA reductase (EC 1.3.1.52), an enzyme catalyzing the reduction of sterically hindered trans-enoyl-CoA substrates. This enzyme participates in branched-chain fatty acid synthesis in the nematode *Ascarius suum* and is capable of reducing a variety of linear and branched chain substrates including 2-methylbutanoyl-CoA, 2-methylpentanoyl-CoA, octanoyl-CoA and pentanoyl-CoA (Duran et al., *J Biol. Chem.* 268:22391-22396 (1993)). Two isoforms of the enzyme, encoded by genes acad1 and acad, have been characterized.

| Gene name | GI# | GenBank Accession # | Organism |
|---|---|---|---|
| acad1 | 2407655 | AAC48316.1 | Ascarius suum |
| Acad | 347404 | AAA16096.1 | Ascarius suum |

1.4.1.a Oxidoreductase (ketone or aldehyde to amino). Oxidoreductases in the EC class 1.4.1 that convert an aldehyde or ketone to its corresponding amine group catalyze several biosynthetic steps in the disclosed pathways. In FIG. 12, the conversions of OHED to 2-AHE (Step J), 2-OHD to 2-AHD (Step H) and adipate semialdehyde to 6-aminocaproate (Step E) are catalyzed by OHED aminating oxidoreductase, 2-OHD aminating oxidoreductase and adipate semialdehyde aminating oxidoreductase. In FIG. 13, conversion of 6-aminocaproate semialdehyde to HMD (Step H) and 6-acetamidohexanal to 6-acetamidohexanamine (Step G), are also catalyzed by aminating oxidoreductases.

Most aminating oxidoreductases catalyze the reversible oxidative deamination of alpha-amino acids with NAD+ or NADP+ as acceptor, and the reactions are typically reversible. Exemplary enzymes include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al., *J. Mol. Biol.* 234:1270-1273 (1993); and McPherson et al., *Nucleic Acids Res.* 11:5257-5266 (1983)), gdh from *Thermotoga maritime* (Kort et al., *Extremophiles.* 1:52-60 (1997); Lebbink et al., *J Mol. BioL* 280:287-296 (1998); and Lebbink et al., *J Mol. Biol.* 289:357-369 (1999)), and gdhA1 from *Halobacterium salinarum* (Ingoldsby et al., *Gene* 349:237-244 (2005)) catalyze the reversible interconversion of glutamate to 2-oxoglutarate and ammonia, while favoring NADP(H), NAD(H), or both, respectively. The Idh gene of *Bacillus cereus* encodes the LeuDH protein that has a wide of range of substrates including leucine, isoleucine, valine, and 2-aminobutanoate (Ansorge and Kula, *Biotechnol Bioeng* 68:557-562 (2000); and Stoyan et al., *J Biotechnol.* 54:77-80 (1997)). The nadX gene from *Thermotoga* maritime encoding for the aspartate dehydrogenase is involved in the biosynthesis of NAD (Yang et al., *J Biol. Chem.* 278:8804-8808 (2003)).

| Gene name | GI# | GenBank Accession # | Organism |
|---|---|---|---|
| gdhA | 118547 | P00370 | Escherichia coli |
| Gdh | 6226595 | P96110.4 | Thermotoga maritima |
| gdhA1 | 15789827 | NP_279651.1 | Halobacterium salinarum |

-continued

| Gene name | GI# | GenBank Accession # | Organism |
|---|---|---|---|
| Ldh | 61222614 | P0A393 | Bacillus cereus |
| nadX | 15644391 | NP_229443.1 | Thermotoga maritima |

Lysine 6-dehydrogenase (deaminating), encoded by lysDH, catalyzes the oxidative deamination of the 6-amino group of L-lysine to form 2-aminoadipate-6-semialdehyde, which in turn non-enzymatically cyclizes to form $\Delta^1$-piperideine-6-carboxylate (Misono and Nagasaki, *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem.* 106:76-80 (1989); and Misono and Nagasaki, *J. Bacteriol.* 150:398-401 (1982)), and *Achromobacter denitrificans* (Ruldeekulthamrong et al., *BMB. Rep.* 41:790-795 (2008)). Such enzymes are particularly good candidates for converting adipate semialdehyde to 6-aminocaproate given the structural similarity between adipate semialdehyde and 2-aminoadipate-6-semialdehyde.

| Gene name | GI# | Accession # | Organism |
|---|---|---|---|
| lysDH | 13429872 | BAB39707 | Geobacillus stearothermophilus |
| lysDH | 15888285 | NP_353966 | Agrobacterium tumefaciens |
| lysDH | 74026644 | AAZ94428 | Achromobacter denitrificans |

2.3.1.a Acyltransferase (transferring CoA to phospho). Acyltransferases that exchange a CoA moiety for a phosphate are in the EC class 2.3.1. Transformations in this category include the conversions of 6-AAHOP to 6-acetamidohexanoyl-CoA (FIG. 13, Step K) and 6-AHOP to 6-aminocaproyl-CoA (FIG. 13, Step L). Exemplary phosphate-transferring acyltransferases include phosphotransacetylase (EC 2.3.1.8), encoded by pta, and phosphotransbutyrylase (EC 2.3.1.19), encoded by ptb. The pta gene from *E. coli* encodes an enzyme that reversibly converts acetyl-CoA into acetyl-phosphate (Suzuki, T., *Biochim. Biophys. Acta* 191:559-569 (1969)). This enzyme can also utilize propionyl-CoA as a substrate, forming propionate in the process (Hesslinger et al., *Mol. Microbiol* 27:477-492 (1998)). Similarly, the ptb gene from *C. acetobutylicum* encodes phosphate transbutyrylase, an enzyme that reversibly converts butyryl-CoA into butyryl-phosphate (Walter et al., Gene 134:107-111 (1993); and Wiesenborn et al., Appl Environ. Microbiol 55:317-322 (1989)). Additional ptb genes are found in butyrate-producing bacterium L2-50 (Louis et al., J. Bacteriol. 186:2099-2106 (2004)) and Bacillus megaterium (Vazquez et al., Curr. Microbiol 42:345-349 (2001)).

| Gene name | GI# | GenBank Accession # | Organism |
|---|---|---|---|
| Pta | 16130232 | NP_416800.1 | Escherichia coli |
| Ptb | 15896327 | NP_349676 | Clostridium acetobutylicum |
| Ptb | 38425288 | AAR19757.1 | butyrate-producing bacterium L2-50 |
| Ptb | 10046659 | CAC07932.1 | Bacillus megaterium |

2.3.1.c Acyltransferase (N-acetyltransferase). N-Acetyltransferases transfer an acetyl group to an amine, forming an N-acetyl group. N-Acetylation serves diverse functions in biological systems including transcriptional regulation, nuclear import, chromosome assembly and nucleosome remodeling (Kouzarides, EMBO J 19:1176-1179 (2000)). N-Acetylation of metabolic intermediates of arginine biosynthetic pathways serves both to protect reactive intermediates from spontaneous cyclization and also to sequester pathway intermediates from competing pathways (Caldovic and Tuchman, Biochem. J 372:279-290 (2003)). Acetylation of 6-ACA (FIG. 13, step D) serves a similar role in the proposed HMD biosynthesis route of FIG. 13, protecting reactive intermediates from spontaneous cyclization.

One candidate enzyme for acetylating 6-ACA is lysine N-acetyltransferase (EC 2.3.1.32), an enzyme which selectively transfers the acetyl moiety from acetyl phosphate to the terminal amino group of L-lysine, beta-L-lysine or L-ornithine. Although this enzyme is not known to acetylate 6-ACA, this substrate is structurally similar to the natural substrate. Lysine N-acetyltransferase has been characterized in Bos taurus (Paik. and Kim, Arch. Biochem. Biophys. 108:221-229, 1964) and Methanosarcina mazei (Pfluger et al., Appl Environ. Microbiol 69:6047-6055 (2003)). Methanogenic archaea M. maripaludis, M. acetivorans, M. barkeri and M. jannaschii are also predicted to encode enzymes with this functionality (Pfluger et al., Appl Environ. Microbiol 69:6047-6055 (2003)).

| Gene name | GI# | GeneBank Accession # | Organism |
|---|---|---|---|
| ablB | 21227037 | NP_632959.1 | Methanosarcina mazei |
| yodP | 44921183 | CAF30418 | Methanococcus maripaludis |
| MA3978 | 20092772 | NP_618847.1 | Methanosarcina acetivorans |
| MJ0635 | 15668816 | NP_247619.1 | Methanocaldococcus jannaschii |
| Mbar_A0671 | 73668215 | YP_304230.1 | Methanosarcina barkeri |

Alternately, 6-ACA acetylation can be catalyzed by an enzyme in the GNAT family of N-acetyltransferases. Such enzymes transfer an acetyl group from acetyl-CoA to a primary amine. The enzyme spermidine N-acetyltransferase (S SAT), also known as diamine N-acetyltransferase (EC 2.3.1.57), is capable of acetylating a variety of small molecule substrates. Purified enzymes from Ascaris suum and Onchocerca volvulus exhibit a broad substrate range that includes HMD (Davids et al., Mol. Biochem. Parasitol. 64:341-344 (1994); and VVittich and Walter, Mol. Biochem. Parasitol. 38:13-17 (1990)), but the associated genes have not been identified to date. Other enzymes with this functionality are found in Bacillus subtilis (Forouhar et al., J. Biol. Chem. 280:40328-40336 (2005)) and Homo sapiens (Casero and Pegg, FASEB J 7:653-661 (1993)). A closely related enzyme is thialysine N-acetyltransferase in C. elegans, an enzyme that accepts a range of substrates including lysine, ornithine, thialysine and others (bo-Dalo et al., Biochem. J 384:129-137 (2004)). Amino acid residues involved in substrate binding were identified in the thialysine N-acetyltransferase from Leishmania major (Luersen, K., FEBS Lett. 579:5347-5352 (2005)). An additional candidate is the diaminobutyrate acetyltransferase (EC 2.3.1.178), an enzyme participating in ectoine biosynthesis in Methylomicrobium alcaliphilum (Reshetnikov et al., Arch. Microbiol 184:286-297 (2006)) C. salexigens (formerly Halomonas elongata) (Canovas et al., Syst. Appl Microbiol 21:487-497 (1998)).

| Gene name | GI# | GenBank Accession # | Organism |
|---|---|---|---|
| paiA | 16080268 | NP_391095.1 | Bacillus subtilis |
| SSAT1 | 114322 | P21673 | Homo sapiens |
| D2023.4 | 17559148 | NP_505978.1 | Caenorhabditis elegans |
| LmjF36.2750 | 68129928 | CAJ09234.1 | Leishmania major |
| ectA | 68366269 | AAY96770.1 | Methylomicrobium alcaliphilum 20Z |
| ectA | 6685422 | Q9ZEU8.1 | Chromohalobacter salexigens |

Figure 14A:
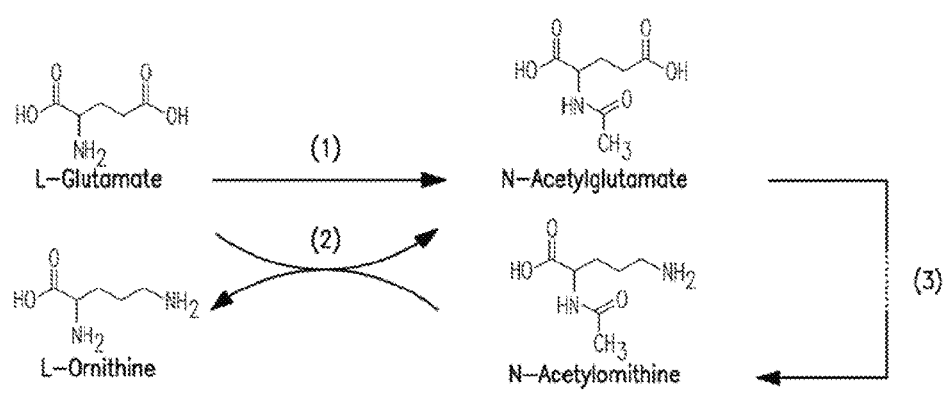
Figure 14B:
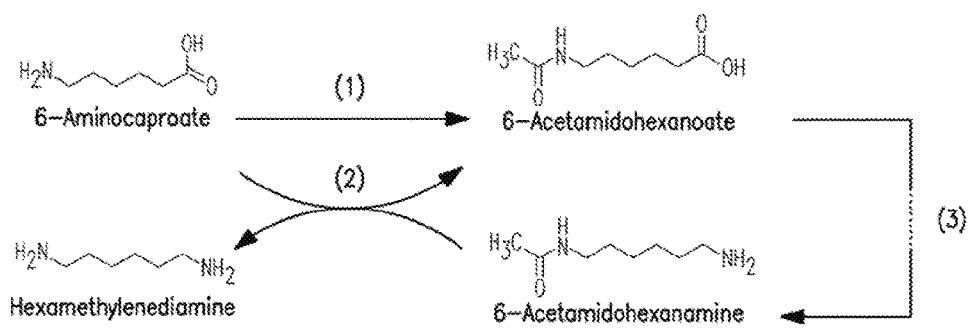

An additional enzyme candidate for acetylating 6-ACA (FIG. 13, Step D) and de-acetylating 6-acetamidehexanamine (FIG. 13, Step H) is ornithine acetyltransferase (OAT, EC 2.3.1.35 and EC 2.3.1.1), a bifunctional enzyme which catalyzes two steps of arginine biosynthesis (FIG. 14A). The first step of arginine biosynthesis (FIG. 14A, step 1) is the N-acetylation of glutamate, catalyzed by OAT with acetyl-CoA as an acetyl donor (O'Reilly and Devine, Microbiology 140 (Pt 5):1023-1025 (1994)). OAT also catalyzes the fifth step of arginine biosynthesis (FIG. 14A, step 2), in which an N-acetyl group is transferred from N-acetyl-L-ornithine to L-glutamate, the first metabolite in the arginine biosynthesis pathway. This transformation serves to recycle the acetyl group and regenerate N-acetylglutamate, conserving energy and thereby making the linear pathway a cyclic route. A similar strategy can be employed in HMD biosynthesis from 6-aminocaproate, with a single enzyme acetylating 6-aminocaproate and de-acetylating 6-acetamidohexanamine to form HMD (FIG. 14B). Exemplary OAT enzymes are encoded by argJ in Bacillus subtilis (O'Reilly and Devine, Microbiology 140 (Pt 5):1023-1025 (1994); and Sakanyan et al., Journal of General Microbiology 138:125-130 (1992)) and ECM40 in S. cerevisiae (Abadjieva et al., J Biol. Chem. 275:11361-11367 (2000); and Liu et al., Eur. J Biochem. 228:291-296 (1995)). Crystal structures of the enzymes from yeast (Maes et al., Acta Crystallogr. Sect. F. Struct. Biol. Cryst. Commun. 62:1294-1297 (2006)) and Mycobacterium tuberculosis (Sankaranarayanan et al., Acta Crystallogr. Sect. F. Struct. Biol. Cryst. Commun. 65:173-176 (2009)) are available. Although encoded by a single open reading frame, OAT enzymes have distinct alpha and beta subunit peptides (Liu et al., Eur. J Biochem. 228:291-296 (1995)).

| Gene name | GI# | GenBank Accession # | Organism |
|---|---|---|---|
| argJ | 16078185 | NP_389002.1 | Bacillus subtilis |
| ECM40 (ARG7) | 6323707 | NP_013778.1 | Saccharomyces cerevisiae |
| Rv1653 | 15608791 | NP_216169.1 | Mycobacterium tuberculosis |

2.3.1.d Acyltransferase (formate C-acyltransferase). The acylation of ketoacids HODH, OHED and 2-OHD to their corresponding CoA derivatives (FIG. 12, Steps L, P and Q) and concurrent release of formate, is catalyzed by formate C-acyltransferase enzymes in the EC class 2.3.1. Enzymes in this class include pyruvate formate-lyase and ketoacid formate-lyase. Pyruvate formate-lyase (PFL, EC 2.3.1.54), encoded by pflB in *E. coli*, converts pyruvate into acetyl-CoA and formate. The active site of PFL contains a catalytically essential glycyl radical that is posttranslationally activated under anaerobic conditions by PFL-activating enzyme (PFL-AE, EC 1.97.1.4) encoded by pflA (Knappe et al., *Proc. Natl. Acad. Sci U.S. A* 81:1332-1335 (1984); and Wong et al., *Biochemistry* 32:14102-14110 (1993)). A pyruvate formate-lyase from *Archaeglubus fulgidus* encoded by pflD has been cloned, expressed in *E. coli* and characterized (Lehtio, L. and A. Goldman, *Protein Eng Des Sel* 17:545-552 (2004)). The crystal structures of the *A. fulgidus* and *E. coli* enzymes have been resolved (Lehtio et al., *J Mol. Biol.* 357:221-235 (2006)). Additional PFL and PFL-AE candidates are found in *Clostridium pasteurianum* (Weidner and Sawers, *J. Bacteriol.* 178:2440-2444 (1996)) and the eukaryotic alga *Chlamydomonas reinhardtii* (Cary et al., *Appl. Environ. Microbiol* 56:1576-1583 (1990)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like PflB, requires post-translational modification by PFL-AE to activate a glycyl radical in the active site (Hesslinger et al., *Mol. Microbiol* 27:477-492 (1998)).

| Gene name | GI# | Accession # | Organism |
|---|---|---|---|
| pflB | 16128870 | NP_415423.1 | Escherichia coli |
| pflA | 16128869 | NP_415422.1 | Escherichia coli |
| tdcE | 48994926 | AAT48170.1 | Escherichia coli |
| pflD | 11499044 | NP_070278.1 | Archaeglubus fulgidus |
| Pfl | 2500058 | Q46266.1 | Clostridium pasteurianum |
| Act | 1072362 | CAA63749.1 | Clostridium pasteurianum |
| pfl1 | 159462978 | XP_001689719.1 | Chlamydomonas reinhardtii |
| pflA1 | 159485246 | XP_001700657.1 | Chlamydomonas reinhardtii |

2.6.1.a Aminotransferase. Steps E, H and J of FIG. 12 and Steps C and G of FIG. 13 require conversion of an aldehyde or ketone to an amino group. This transformation can be accomplished by an aminotransferase (EC 2.6.1.-). The conversion of an aldehyde to a terminal amine (FIG. 12, Step E; FIG. 13, Steps C and G) can be, catalyzed by gamma-aminobutyrate transaminase (GABA transaminase). One *E. coli* GABA transaminase is encoded by gabT and transfers an amino group from glutamate to the terminal aldehyde of succinic semialdehyde (Bartsch et al., *J. Bacteriol.* 172:7035-7042 (1990)). This enzyme exhibits a broad substrate range (Liu et al., *Biochemistry* 43:10896-10905 (2004)). The gene product of puuE encodes the other 4-aminobutyrate transaminase in *E. coli* (Kurihara et al., *J. Biol. Chem.* 280:4602-4608 (2005)). GABA transaminases in *Mus musculus, Pseudomonas fluorescens*, and *Sus scrofa* have been shown to react with 6-aminocaproic acid (Cooper, Methods EnzymoL 113:80-82 (1985); and Scott and Jakoby, *J Biol. Chem.* 234:932-936 (1959)).

| Gene name | GI# | GenBank Accession # | Organism |
|---|---|---|---|
| gabT | 16130576 | NP_417148.1 | Escherichia coli |
| puuE | 16129263 | NP_415818.1 | Escherichia coli |
| Abat | 37202121 | NP_766549.2 | Mus musculus |
| gabT | 70733692 | YP_257332.1 | Pseudomonas fluorescens |
| Abat | 47523600 | NP_999428.1 | Sus scrofa |

Additional enzyme candidates include putrescine aminotransferases or other diamine aminotransferases. Such enzymes are particularly well suited for carrying out the conversion of 6-aminocaproate semialdehyde to HMD. The *E. coli* putrescine aminotransferase is encoded by the ygjG gene and the purified enzyme also was able to transaminate cadaverine and spermidine (Samsonova et al., *BMC. Microbiol* 3:2 (2003)). In addition, activity of this enzyme on 1,7-diaminoheptane and with amino acceptors other than 2-oxoglutarate (e.g., pyruvate, 2-oxobutanoate) has been reported (Kim, *J Biol. Chem.* 239:783-786 (1964); and Samsonova et al., *BMC. Microbiol* 3:2 (2003)). A putrescine aminotransferase with higher activity with pyruvate as the amino acceptor than alpha-ketoglutarate is the spuC gene of *Pseudomonas aeruginosa* (Lu et al., *J. Bacteriol.* 184:3765-3773 (2002)).

| Gene name | GI# | GenBank Accession # | Organism |
|---|---|---|---|
| ygjG | 145698310 | NP_417544 | Escherichia coli |
| spuC | 9946143 | AAG03688 | Pseudomonas aeruginosa |

Additional candidate enzymes include beta-alanine/alpha-ketoglutarate aminotransferases which produce malonic semialdehyde from beta-alanine (WO08027742). The gene product of SkPYD4 in *Saccharomyces kluyveri* was shown to preferentially use beta-alanine as the amino group donor (Andersen and Hansen, Gene 124:105-109 (1993)). SkUGA1 encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both β-alanine and GABA transamination (Andersen and Hansen, Gene 124:105-109 (1993)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat 1968 (Kakimoto et al., *Biochim. Biophys. Acta* 156:374-380 (1968); and Tamaki et al., *Methods Enzymol.* 324:376-389 (2000)).

| Gene name | GI# | GenBank Accession # | Organism |
|---|---|---|---|
| SkyPYD4 | 98626772 | ABF58893.1 | Saccharomyces kluyveri |
| SkUGA1 | 98626792 | ABF58894.1 | Saccharomyces kluyveri |
| UGA1 | 6321456 | NP_011533.1 | Saccharomyces cerevisiae |
| Abat | 122065191 | P50554.3 | Rattus norvegicus |
| Abat | 120968 | P80147.2 | Sus scrofa |

Steps J and H of FIG. 12 are catalyzed by aminotransferases that transform amino acids into oxo-acids. In Step J, OHED is transaminated to form 2-AHE by OHED aminotransferase. The transamination of 2-OHD to 2-AHD by 2-OHD aminotransferase (Step H) is a similar reaction. An exemplary enzyme candidate for catalyzing these reactions is aspartate aminotransferase, an enzyme that naturally transfers an oxo group from oxaloacetate to glutamate, forming alpha-ketoglutarate and aspartate. Aspartate is similar in structure to OHED and 2-AHD. Aspartate aminotransferase activity is catalyzed by, for example, the gene products of aspC from *Escherichia coli* (Yagi et al., *FEBS Lett.* 100:81-84, (1979); and Yagi et al., *Methods Enzymol.* 113: 83-89 (1985)), AAT2 from *Saccharomyces cerevisiae* (Yagi et al., *J. Biochem.* 92:35-43 (1982)) and ASP5 from *Arabidopsis thaliana* (de la Torre et al., *Plant J* 46:414-425 (2006); *Kwok and Hanson, J Exp. Bot.* 55:595-604 (2004); and Wilkie and Warren, *Protein Expr. Purif.* 12:381-389 (1998)). The enzyme from *Rattus norvegicus* has been shown to transaminate alternate substrates such as 2-aminohexanedioic acid and 2,4-diaminobutyric acid (Recasens et al., *Biochemistry* 19:4583-4589 (1980)). Aminotransferases that work on other amino-acid substrates can catalyze this transformation. Valine aminotransferase catalyzes the conversion of valine and pyruvate to 2-ketoisovalerate and alanine. The *E. coli* gene, avtA, encodes one such enzyme (Whalen and Berg, C. *J. Bacteriol.* 150:739-746 (1982)). This gene product also catalyzes the transamination of α-ketobutyrate to generate α-aminobutyrate, although the amine donor in this reaction has not been identified (Whalen and Berg, *J. Bacteriol.* 158:571-574 (1984)). The gene product of the *E. coli* serC catalyzes two reactions, phosphoserine aminotransferase and phosphohydroxythreonine aminotransferase (Lam and Winkler, *J. Bacteriol.* 172:6518-6528 (1990)), and activity on non-phosphorylated substrates could not be detected (Drewke et al., *FEBS. Lett.* 390:179-182 (1996)).

| Gene name | GI# | GenBank Accession # | Organism |
|---|---|---|---|
| aspC | 16128895 | NP_415448.1 | Escherichia coli |
| AAT2 | 1703040 | P23542.3 | Saccharomyces cerevisiae |
| ASP5 | 20532373 | P46248.2 | Arabidopsis thaliana |
| Got2 | 112987 | P00507 | Rattus norvegicus |
| avtA | 49176374 | YP_026231.1 | Escherichia coli |
| serC | 16128874 | NP_415427.1 | Escherichia coli |

2.7.2.a Phosphotransferase (carboxy acceptor). Phosphotransferase enzymes in the EC class 2.7.2 transform carboxylic acids to phosphonic acids with concurrent hydrolysis of one ATP. Steps A and E in FIG. 13 require a phosphotransferase to activate the carboxyl groups of 6-ACA (Step A) and 6-acetamidohexanoate (Step E) to their corresponding phosphonic acids. Butyrate kinase carries out the reversible conversion of butyryl-phosphate to butyrate during acidogenesis in *C. acetobutylicum* (Cary et al., *Appl. Environ. Microbiol* 56:1576-1583 (1990)). This enzyme is encoded by either of the two buk gene products (Huang et al., *J. Mol. Microbiol Biotechnol* 2:33-38 (2000)). Related enzyme isobutyrate kinase from *Thermotoga maritima* has also been expressed in *E. coli* and crystallized (Diao et al., *Acta Crystallogr. D. Biol. Crystallogr.* 59:1100-1102 (2003); and Diao and Hasson, *J. Bacteriol.* 191:2521-2529 (2009)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng and Viola, *Arch. Biochem. Biophys.* 335: 73-81 (1996)). Two additional kinases in *E. coli* are also good candidates: acetate kinase and gamma-glutamyl kinase. The *E. coli* acetate kinase, encoded by ackA (Skarstedt and Silverstein, *J. Biol. Chem.* 251:6775-6783 (1976)), phosphorylates propionate in addition to acetate (Hesslinger et al., *Mol. Microbiol* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Gene name | GI# | GenBank Accession # | Organism |
|---|---|---|---|
| buk1 | 15896326 | NP_349675 | Clostridium acetobutylicum |
| buk2 | 20137415 | Q97II1 | Clostridium acetobutylicum |
| buk2 | 6685256 | Q9X278.1 | Thermotoga maritima |
| lysC | 16131850 | NP_418448.1 | Escherichia coli |
| ackA | 16130231 | NP_416799.1 | Escherichia coli |
| proB | 16128228 | NP_414777.1 | Escherichia coli |

Acetylglutamate kinase phosphorylates acetylated glutamate during arginine biosynthesis and is a good candidate for phosphorylating 6-acetamidohexanoate (FIG. 13, Step E). This enzyme is not known to accept alternate substrates; however, several residues of the *E. coli* enzyme involved in substrate binding and phosphorylation have been elucidated by site-directed mutagenesis (Marco-Martin et al., *J Mol. Biol.* 334:459-476 (2003); and Ramon-Maiques et al., *Structure.* 10:329-342 (2002)). The enzyme is encoded by argB in *Bacillus subtilis* and *E. coli* (Parsot et al., *Gene* 68:275-283 (1988)), and ARG5,6 in *S. cerevisiae* (Pauwels et al., *Eur. J Biochem.* 270:1014-1024 (2003)). The ARG5,6 gene of *S. cerevisiae* encodes a polyprotein precursor that is matured in the mitochondrial matrix to become acetylglutamate kinase and acetylglutamylphosphate reductase, an enzyme candidate for the reduction of 6-AAHOP (FIG. 13, Step F).

| Gene name | GI# | Accession # | Organism |
|---|---|---|---|
| argB | 145698337 | NP_418394.3 | Escherichia coli |
| argB | 16078186 | NP_389003.1 | Bacillus subtilis |
| ARG5,6 | 6320913 | NP_010992.1 | Saccharomyces cerevisiae |

2.8.3.a Coenzyme-A transferase. Coenzyme-A (CoA) transferases catalyze the reversible transfer of a CoA moiety from one molecule to another. In Step M of FIG. 13, 3-aminocaproyl-CoA is formed by the transfer of a CoA group from acetyl-CoA, succinyl-CoA, or another CoA donor. A similar transformation is catalyzed by 6-acetamidohexanoate CoA-transferase, shown in Step I of FIG. 13. Exemplary CoA transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., *Proc. Natl. Acad. Sci U.S. A* 105:2128-2133 (2008); and Sohling and Gottschalk, *J. Bacteriol.* 178:871-880 (1996)). Similar CoA transferase activities are also present in *Trichomonas vaginalis* (van Grinsven et al., *J Biol. Chem.* 283:1411-1418 (2008)) and *Trypanosoma brucei* (Riviere et al., *J. Biol. Chem.* 279:45337-45346 (2004)).

| Gene name | GI# | GenBank Accession # | Organism |
|---|---|---|---|
| cat1 | 729048 | P38946.1 | Clostridium kluyveri |
| cat2 | 172046066 | P38942.2 | Clostridium kluyveri |
| cat3 | 146349050 | EDK35586.1 | Clostridium kluyveri |
| TVAG_395550 | 123975034 | XP_001330176 | Trichomonas vaginalis G3 |
| Tb11.02.0290 | 71754875 | XP_828352 | Trypanosoma brucei |

A CoA transferase that can utilize acetyl-CoA as the CoA donor is acetoacetyl-CoA transferase, encoded by the E. coli atoA (alpha subunit) and atoD. (beta subunit) genes (Korolev et al., Acta Crystallogr. D. Biol. Crystallogr. 58:2116-2121 (2002); and Vanderwinkel et al., Biochem. Biophys. Res. Commun. 33:902-908 (1968)). This enzyme has a broad substrate range (Sramek and Frerman, Arch. Biochem. Biophys. 171:14-26 (1975)) and has been shown to transfer the CoA moiety to acetate from a variety of branched and linear acyl-CoA substrates, including isobutyrate (Matthies and Schink, Appl Environ. Microbiol 58:1435-1439 (1992)), valerate (Vanderwinkel et al., Biochem. Biophys. Res. Commun. 33:902-908 (1968)) and butanoate (Vanderwinkel et al., Biochem. Biophys. Res. Commun. 33:902-908 (1968)). This enzyme is induced at the transcriptional level by acetoacetate, so modification of regulatory control may be necessary for engineering this enzyme into a pathway (Pauli and Overath, Eur. J Biochem. 29:553-562 (1972)). Similar enzymes exist in Corynebacterium glutamicum ATCC 13032 (Duncan et al., Appl. Environ. Microbiol 68:5186-5190 (2002)), Clostridium acetobutylicum (Cary et al., Appl. Environ. Microbiol 56:1576-1583 (1990); and Wiesenborn et al., Appl. Environ. Microbiol 55:323-329 (1989)), and Clostridium saccharoperbutylacetonicum (Kosaka et al., Biosci. Biotechnol Biochem. 71:58-68 (2007)).

| Gene name | GI# | GenBank Accession # | Organism |
|---|---|---|---|
| AtoA | 2492994 | NP_416726 | Escherichia coli K12 |
| AtoD | 2492990 | NP_416725 | Escherichia coli K12 |
| actA | 62391407 | YP_226809.1 | Corynebacterium glutamicum ATCC 13032 |
| cg0592 | 62389399 | YP_224801.1 | Corynebacterium glutamicum ATCC 13032 |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

The glutaconyl-CoA-transferase (EC 2.8.3.12) enzyme from anaerobic bacterium Acidaminococcus fermentans reacts with glutaconyl-CoA and 3-butenoyl-CoA (Mack et al., Eur. J. Biochem. 226:41-51 (1994)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., Eur. J Biochem. 118:315-321 (1981)). The enzyme has been cloned and expressed in E. coli (Mack et al., Eur. J. Biochem. 226:41-51 (1994)).

| Gene name | GI# | GenBank Accession # | Organism |
|---|---|---|---|
| gctA | 559392 | CAA57199.1 | Acidaminococcus fermentans |
| gctB | 559393 | CAA57200.1 | Acidaminococcus fermentans |

Yet another CoA transferase is the two-unit succinyl-CoA:3:oxoacid-CoA transferase encoded by pcaI and pcaJ in Pseudomonas putida (Kaschabek et al., J. Bacteriol. 184:207-215 (2002)). Similar enzymes based on homology exist in Acinetobacter sp. ADP1 (Kowaichuk et al., Gene 146:23-30 (1994)). Additional exemplary succinyl-CoA:3: oxoacid-CoA transferases are present in Helicobacter pylori (Corthesy-Theulaz et al., J. Biol. Chem. 272:25659-25667 (1997)) and Bacillus subtilis (Stols et al., Protein Expr. Purif. 53:396-403 (2007)).

| Gene name | GI# | GeneBank Accession # | Organism |
|---|---|---|---|
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |

3.5.1.a Hydrolase (acting on linear amides). Deacetylation of linear acetamides is catalyzed by an amidohydrolase in the 3.5.1 family of enzymes. Such an enzyme is required for the deacetylation of 6-acetamidohexanamine to HMD (FIG. 13, Step H). An enzyme catalyzing a similar transformation is 4-acetamidobutyrate deacetylase (EC 3.5.1.63), which naturally deacetylates 4-acetamidobutyrate. The enzyme, studied for its role in putrescine degradation in Candida boidinii (Gillyon et al., Journal of General Microbiology 133:2477-2485 (1987)), has been shown to deacetylate a variety of substrates including 6-acetamidohexanoate (Haywood and Large, Journal of General Microbiology 132:7-14 (1986)). Although 6-Acetamidohexanoate is similar in structure to the desired substrate, deacetylation of this compound (FIG. 13, step D, reverse reaction) may hinder efficient production of HMD. Protein engineering or directed evolution may be required to improve specificity for 6-acetamidohexanamine. The gene associated with this activity has not been identified to date.

2. Acetylpolyamine amidohydrolase (EC 3.5.1.62), is another candidate enzyme that forms the diamines putrescine and cadaverine from their acetylated precursors. The acetylpolyamine deacetylase (AphA) from Mycoplana ramosa has been cloned in E. coli and characterized (Sakurada et al., J. Bacteriol. 178:5781-5786 (1996)) and a crystal structure is available (Fujishiro et al., Biochem. Biophys. Res. Commun. 157:1169-1174 (1988)). This enzyme has also been studied in Micrococcus luteus, but the associated gene has not been identified to date (Suzuki et al., Biochim. Biophys. Acta 882:140-142 (1986)). A protein the histone deacetylase superfamily with high sequence similarity to AphA was identified in the M. luteus genome (evalue=1e-18, 37% identity). The N-acetyl-L-ornithine deacetylase from E. coli is another candidate amidohydrolase (EC 3.5.1.16). The E. coli enzyme, encoded by the argE gene (McGregor et al., J Am. Chem. Soc. 127:14100-14107 (2005); and Meinnel et al., J. Bacteriol. 174:2323-2331 (1992)), removes N-acetyl groups from a variety of substrates including ornithine, lysine, glutamine, and other amino acids (Javid-Majd and Blanchard, Biochemistry 39:1285-1293 (2000)).

| Gene name | GI# | GenBank Accession # | Organism |
|---|---|---|---|
| aphA | 3023317 | Q48935.1 | *Mycoplana ramose* |
| MlutDRAFT_1143 | 172071524 | EDT57566.1 | *Micrococcus luteus* |
| argE | 16131795 | NP_418392.1 | *Escherichia coli* |

4.1.1.a Carboxy-lyase. Steps D and F in FIG. 12 are catalyzed by 2-ketoacid decarboxylase enzymes that generate 6-OHE and adipate semialdehyde from OHED (Step F) and 2-OHD (Step D). In addition, alpha-ketoglutarate is decarboxylated to form pathway precursor succinic semialdehyde by alpha-ketoglutarate decarboxylase, a keto-acid decarboxylase. The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in *E. coli* (Killenberg-Jabs et al., *Eur. J. Biochem.* 268:1698-1704 (2001); Li, H. and F. Jordan, *Biochemistry.* 38:10004-10012 (1999); and ter Schure et al., *Appl. Environ. Microbiol.* 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng Des Sel* 18:345-357 (2005)). The crystal structure of this enzyme is available (Killenberg-Jabs et al., *Eur. J. Biochem.* 268:1698-1704 (2001)). Other well-characterized PDC candidates include the enzymes from *Acetobacter pasteurians* (Chandra et al., *Arch. Microbiol.* 176:443-451 (2001)) and *Kluyveromyces lactis* (Krieger et al., *Eur. J. Biochem.* 269:3256-3263 (2002)).

| Gene name | GI# | GeneBank Accession # | Organism |
|---|---|---|---|
| Pdc | 118391 | P06672.1 | *Zymomonas mobilus* |
| pdc1 | 30923172 | P06169 | *Saccharomyces cerevisiae* |
| Pdc | 20385191 | Q8L388 | *Acetobacter pasteurians* |
| pdc1 | 52788279 | Q12629 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al., *Biochemistry* 37:9918-9930 (1998); and Polovnikova et al., *Biochemistry* 42:1820-1830 (2003)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Protein Eng* 15:585-593 (2002); and Lingen et al., *Chembiochem.* 4:721-726 (2003)). The enzyme from *Pseudomonas aeruginosa*, encoded by mdlC, has also been characterized experimentally (Barrowman et al., *FEMS Microbiology Letters* 34:57-60 (1986)). Additional gene candidates from *Pseudomonas stutzeri, Pseudomonas fluorescens* and other organisms can be inferred by sequence homology or identified using a growth selection system developed in *Pseudomonas putida* (Henning et al., *Appl. Environ. Microbiol.* 72:7510-7517 (2006)).

| Gene name | GI# | GenBank Accession # | Organism |
|---|---|---|---|
| mdlC | 3915757 | P20906.2 | *Pseudomonas putida* |
| mdlC | 81539678 | Q9HUR2.1 | *Pseudomonas aeruginosa* |
| dpgB | 126202187 | ABN80423.1 | *Pseudomonas stutzeri* |
| ilvB-1 | 70730840 | YP_260581.1 | *Pseudomonas fluorescens* |

A third enzyme capable of decarboxylating 2-oxoacids is alpha-ketoglutarate decarboxylase (KGl7). The substrate range of this class of enzymes has not been studied to date. The KDC from *Mycobacterium tuberculosis* (Tian et al., *Proc Natl Acad Sci USA* 102:10670-10675 (2005)) has been cloned and functionally expressed in other internal projects at Genomatica. However, it is not an ideal candidate for strain engineering because it is large ("130 kD) and GC-rich. KDC enzyme activity has been detected in several species of rhizobia including *Bradyrhizobium japonicum* and *Mesorhizobium loti* (Green et al., *J. Bacteriol.* 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka and Nakano, *Arch. Biochem. Biophys.* 288:22-28 (1991)). The first twenty amino acids starting from the N-terminus were sequenced MTYKAPVKDVKFLLDKVFKV (SEQ ID NO: 1) (Shigeoka and Nakano, *Arch. Biochem. Biophys.* 288:22-28 (1991)). The gene can be identified by testing candidate genes containing this N-terminal sequence for KDC activity.

| Gene name | GI# | GenBank Accession # | Organism |
|---|---|---|---|
| Kgd | 160395583 | O50463.4 | *Mycobacterium tuberculosis* |
| Kgd | 27375563 | NP_767092.1 | *Bradyrhizobium japonicum* |
| Kgd | 13473636 | NP_105204.1 | *Mesorhizobium loti* |

A fourth candidate enzyme for catalyzing this step is branched chain alpha-ketoacid decarboxylase (BCKA). This class of enzyme has been shown to act on a variety of compounds varying in chain length from 3 to 6 carbons (Oku and Kaneda, *J Biol Chem.* 263:18386-18396 (1988); and Smit et al., *Appl Environ Microbiol.* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., *Appl Environ Microbiol.* 71:303-311 (2005)). The enzyme has been structurally characterized (Berg et al., *Science.* 318:1782-1786 (2007)). Sequence alignments between the *Lactococcus lactis* enzyme and the pyruvate decarboxylase of *Zymomonas mobilis* indicate that the catalytic and substrate recognition residues are nearly identical (Siegert et al., *Protein Eng Des Sel* 18:345-357 (2005)), so this enzyme would be a promising candidate for directed engineering Decarboxylation of alpha-ketoglutarate by a BCKA was detected in *Bacillus subtilis*; however, this activity was low (5%) relative to activity on other branched-chain substrates (Oku and Kaneda, *J Biol Chem.* 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

| Gene name | GI# | GenBank Accession # | Organism |
|---|---|---|---|
| kdcA | 44921617 | AAS49166.1 | *Lactococcus lactis* |

Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J. Biol. Chem.* 267:16601-16606 (1992); Wynn et al., *J. Biol. Chem.* 267: 1881-1887 (1992); and Wynn et al., *J. Biol. Chem.* 267: 12400-12403 (1992)). In these studies, the authors found that co-expression of chaperonins GroEL and GroES enhanced the specific activity of the decarboxylase by 500-fold (Wynn et al., *J. Biol. Chem.* 267:12400-12403 (1992)). These enzymes are composed of two alpha and two beta subunits.

| Gene name | GI# | GenBankAccession # | Organism |
|---|---|---|---|
| BCKDHB | 34101272 | NP_898871.1 | *Homo sapiens* |
| BCKDHA | 11386135 | NP_000700.1 | *Homo sapiens* |
| BCKDHB | 115502434 | P21839 | *Bos taurus* |
| BCKDHA | 129030 | P11178 | *Bos taurus* |

The decarboxylation of 2-AHD to 6-aminocaproate (FIG. 12, Step I) is catalyzed by an amino acid decarboxylase such as aspartate decarboxylase. Aspartate decarboxylase participates in pantothenate biosynthesis and is encoded by gene panD in *Escherichia coli* (Dusch et al., *Appl. Environ. Microbiol* 65:1530-1539 (1999); Merke and Nichols, *FEMS Microbiol Lett.* 143:247-252 (1996); Ramjee et al., *Biochem. J* 323 (Pt 3):661-669 (1997); and Schmitzberger et al., *EMBO J* 22:6193-6204 (2003)). Similar enzymes from *Mycobacterium tuberculosis* (Chopra et al., *Protein Expr. Purif.* 25:533-540 (2002)) and *Corynebacterium glutamicum* (Dusch et al., *Appl. Environ. Microbiol* 65:1530-1539 (1999)) have been expressed and characterized in *E. coli*.

| Gene name | GI# | Accession # | Organism |
|---|---|---|---|
| panD | 67470411 | P0A790 | *Escherichia coli* K12 |
| panD | 18203593 | O9X4N0 | *Corynebacterium Glutamicum* |
| panD | 54041701 | P65660.1 | *Mycobacterium tuberculosis* |

4.1.2.a Aldehyde-lyase. HOHD aldolase, also known as HHED aldolase, catalyzes the conversion of 4-hydroxy-2-oxo-heptane-1,7-dioate (HOHD) into pyruvate and succinic semialdehyde (FIG. 12, Step A). The enzyme is a divalent metal ion dependent class II aldolase, catalyzing the final step of 4-hydroxyphenylacetic acid degradation in *E. coli* C, *E. coli* W, and other organisms. In the native context, the enzyme functions in the degradative direction. The reverse (condensation) reaction is thermodynamically unfavorable; however the equilibrium can be shifted through coupling HOHD aldolase with downstream pathway enzymes that work efficiently on reaction products. Such strategies have been effective for shifting the equilibrium of other aldolases in the condensation direction (Nagata et al., *Appl Microbiol Biotechnol* 44:432-438 (1995); and Pollard et al., *Appl Environ. Microbiol* 64:4093-4094 (1998)). The *E. coli* C enzyme, encoded by hpcH, has been extensively studied and has recently been crystallized (Rea et al., *J Mol. Biol.* 373:866-876 (2007); and Stringfellow et al., *Gene* 166:73-76 (1995)). The *E. coli* W enzyme is encoded by hpaI (Prieto et al., *J. Bacteriol.* 178:111-120 (1996)).

| Gene name | GI# | GenBank Accession # | Organism |
|---|---|---|---|
| hpcH | 633197 | CAA87759.1 | *Escherichia coli* C |
| hpaI | 38112625 | AAR11360.1 | *Escherichia coli* W |

4.2.1.a Hydro-lyase. The enzyme OHED hydratase participates in 4-hydroxyphenylacetic acid degradation, where it converts 2-oxo-hept-4-ene-1,7-dioate (OHED) to 2-oxo-4-hydroxy-hepta-1,7-dioate (HODH) using magnesium as a cofactor (Burks et al., *J. Am. Chem. Soc.* 120 (1998)) (FIG. 12, Step B). OHED hydratase enzyme candidates have been identified and characterized in *E. coli* C (Izumi et al., *J Mol. Biol.* 370:899-911 (2007); and Roper et al., *Gene* 156:47-51 (1995)) and *E. coli* W (Prieto et al., *J. Bacteriol.* 178:111-120 (1996)). Sequence comparison reveals homologs in a range of bacteria, plants and animals. Enzymes with highly similar sequences are contained in *Klebsiella pneumonia* (91% identity, evalue=2e-138) and *Salmonella enterica* (91% identity, evalue=4e-138), among others.

| Gene name | GI# | Gene Bank Accession # | Organism |
|---|---|---|---|
| hpcG | 556840 | CAA57202.1 | *Escherichia coli* C |
| hpaH | 757830 | CAA86044.1 | *Escherichia coli* W |
| hpaH | 150958100 | ABR80130.1 | *Klebsiella pneumoniae* |
| Sari_01896 | 160865156 | ABX21779.1 | *Salmonella enterica* |

Dehydration of 3-hydroxyadipyl-CoA to 2,3-dehydroadipyl-CoA (FIG. 12, Step M) is catalyzed by an enzyme with enoyl-CoA hydratase activity. 3-Hydroxybutyryl-CoA dehydratase (EC 4.2.1.55), also called crotonase, dehydrates 3-hydroxyisobutyryl-CoA to form crotonoyl-CoA (FIG. 14, step 2). Crotonase enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus, Acidianus,* and *Metallosphaera*. Exemplary genes encoding crotonase enzymes can be found in *C. acetobutylicum* (Atsumi et al., *Metab Eng* 10:305-311 (2008); and Boynton et al., *J. Bacteriol.* 178:3015-3024 (1996)), *C. kluyveri* (Hillmer and Gottschalk, *FEBS Lett.* 21:351-354 (1972)), and Metallosphaera sedula (Berg et al., *Science.* 318:1782-1786 (2007)) though the sequence of the latter gene is not known.

| Gene name | GI# | GeneBank Accession # | Organism |
|---|---|---|---|
| Crt | 15895969 | NP_349318.1 | *Clostridium acetobutylicum* |
| crt1 | 153953091 | YP_001393856.1 | *Clostridium kluyveri* |

Enoyl-CoA hydratases (EC 4.2.1.17) also catalyze the dehydration of 3-hydroxyacyl-CoA substrates (Agnihotri and Liu., J. Bacteriol. 188:8551-8559 (2003); Conrad et al., J. Bacteriol. 118:103-111 (1974); and Roberts et al., Arch. Microbiol 117:99-108 (1978)). The enoyl-CoA hydratase of Pseudomonas putida, encoded by ech, catalyzes the conversion of 3-hydroxybutyryl-CoA to crotonoyl-CoA (Roberts et al., Arch. Microbiol 117:99-108 (1978)). Additional enoyl-CoA hydratase candidates are phaA and phaB, of P. putida, and paaA and paaB from P. fluorescens (Olivera et al., Proc. Natl. Acad. Sci U.S. A 95:6419-6424 (1998)). The gene product of pimF in Rhodopseudomonas palustris is predicted to encode an enoyl-CoA hydratase that participates in pimeloyl-CoA degradation (Harrison and Harwood, Microbiology 151:727-736 (2005)). Lastly, a number of Escherichia coli genes have been shown to demonstrate enoyl-CoA hydratase functionality including maoC (Park and Lee, J. Bacteriol. 185:5391-5397 (2003)), paaF (Ismail et al., J. Biochem. 270:3047-3054 (2003); Park and Lee, Appl. Biochem. Biotechnol 113-116:335-346 (2004); and Park and Yup, Biotechnol Bioeng 86:681-686 (2004)) and paaG (Ismail et al., J. Biochem. 270:3047-3054 (2003); Park and Lee, Appl. Biochem. Biotechnol 113-116:335-346 (2004); and Park and Yup, Biotechnol Bioeng 86:681-686 (2004)).

| Gene name | GI# | GenBank Accession # | Organism |
|---|---|---|---|
| Ech | 26990073 | NP_745498.1 | Pseudomonas putida |
| paaA | 26990002 | NP_745427.1 | Pseudomonas putida |
| paaB | 26990001 | NP_745426.1 | Pseudomonas putida |
| phaA | 106636093 | ABF82233.1 | Pseudomonas fluorescens |
| phaB | 106636094 | ABF82234.1 | Pseudomonas fluorescens |
| pimF | 39650635 | CAE29158 | Rhodopseudomonas palustris |
| maoC | 16129348 | NP_415905.1 | Escherichia coli |
| paaF | 16129354 | NP_415911.1 | Escherichia coli |
| paaG | 16129355 | NP_415912.1 | Escherichia coli |

Alternatively, the E. coli gene products of fadA and fadB encode a multienzyme complex involved in fatty acid oxidation that exhibits enoyl-CoA hydratase activity (Nakahigashi and Inokuchi, Nucleic Acids Res. 18:4937 (1990); Yang, J. Bacteriol. 173:7405-7406 (1991); and Yang et al., Biochemistry 30:6788-6795 (1991)). Knocking out a negative regulator encoded by fadR can be utilized to activate the fadB gene product (Sato et al., J Biosci. Bioeng 103:38-44 (2007)). The fadI and fadJ genes encode similar functions and are naturally expressed under anaerobic conditions (Campbell et al., Mol. Microbiol 47:793-805 (2003)).

| Gene name | GI# | GenBank Accession # | Organism |
|---|---|---|---|
| fadA | 49176430 | YP_026272.1 | Escherichia coli |
| fadB | 16131692 | NP_418288.1 | Escherichia coli |
| fadI | 16130275 | NP_416844.1 | Escherichia coli |
| fadJ | 16130274 | NP_416843.1 | Escherichia coli |
| fadR | 16129150 | NP_415705.1 | Escherichia coli |

6.2.1.a Acid-thiol ligase (also called CoA synthetase). Steps I and M of FIG. 13 require acid-thiol ligase or CoA synthetase functionality to transform 6-ACA and 6-acetamidohexanoate into their corresponding CoA derivatives (the terms ligase, synthetase, and synthase are used herein interchangeably and refer to the same enzyme class). Enzymes catalyzing these exact transformations have not been characterized to date; however, several enzymes with broad substrate specificities have been described in the literature. ADP-forming acetyl-CoA synthetase (ACD, EC 6.2.1.13) is an enzyme that couples the conversion of acyl-CoA esters to their corresponding acids with the concomitant synthesis of ATP. ACD I from Archaeoglobus fulgidus, encoded by AF1211, was shown to operate on a variety of linear and branched-chain substrates including isobutyrate, isopentanoate, and fumarate (Musfeldt and Schonheit, J. Bacteriol 184:636-644 (2002)). A second reversible ACD in Archaeoglobus fulgidus, encoded by AF1983, was also shown to have a broad substrate range with high activity on cyclic compounds phenylacetate and indoleacetate (Musfeldt and Schonheit, J. Bacteriol. 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen and Schonheit, Arch. Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen and Schonheit, Arch. Microbiol 182:277-287 (2004)). Directed evolution or engineering can be used to modify this enzyme to operate at the physiological temperature of the host organism. The enzymes from A. fulgidus, H. marismortui and P. aerophilum have all been cloned, functionally expressed, and characterized in E. coli (Brasen and Schonheit, Arch. Microbiol 182:277-287 (2004); and Musfeldt and Schonheit, J. Bacteriol. 184:636-644 (2002)). An additional candidate is the enzyme encoded by sucCD in E. coli, which naturally catalyzes the formation of succinyl-CoA from succinate with the concomitant consumption of one ATP, a reaction which is reversible in vivo (Buck et al., Biochemistry 24:6245-6252 (1985)).

| Gene name | GI# | GenBank Accession # | Organism |
|---|---|---|---|
| AF1211 | 11498810 | NP_070039.1 | Archaeoglobus fulgidus DSM 4304 |
| AF1983 | 11499565 | NP_070807.1 | Archaeoglobus fulgidus DSM 4304 |
| Scs | 55377722 | YP_135572.1 | Haloarcula marismortui ATCC 43049 |
| PAE3250 | 18313937 | NP_560604.1 | Pyrobaculum aerophilum str. IM2 |
| sucC | 16128703 | NP_415256.1 | Escherichia coli |
| sucD | 1786949 | AAC73823.1 | Escherichia coli |

Another candidate enzyme for this step is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from Pseudomonas mendocina, cloned into E. coli, was shown to accept the alternate substrates hexanedioate and nonanedioate (Binieda et al., Biochem. J 340 (Pt 3):793-801 (1999)). Other candidates are found in Bacillus subtilis (Bower et al., J. Bacteriol. 178:4122-4130 (1996)) and Lysinibacillus sphaericus (formerly Bacillus sphaericus) (Ploux et al., Biochem. J 287 (Pt 3):685-690 (1992)).

| Gene name | GI# | GenBank Accession # | Organism |
|---|---|---|---|
| pauA | 15596214 | NP_249708.1 | Pseudomonas mendocina |
| bioW | 50812281 | NP_390902.2 | Bacillus subtilis |
| bioW | 115012 | P22822.1 | Lysinibacillus sphaericus |

Additional CoA-ligases include the rat dicarboxylate-CoA ligase for which the sequence is yet uncharacterized (Vamecq et al., Biochem. J 230:683-693 (1985)), either of the two characterized phenylacetate-CoA ligases from *P. chrysogenum* (Lamas-Maceiras et al., Biochem. J 395:147-155 (2006); and Wang et al., Biochem. Biophys. Res. Commun. 360:453-458 (2007)) and the phenylacetate-CoA ligase from *Pseudomonas putida* (Martinez-Blanco et al., J. Biol. Chem. 265:7084-7090 (1990)). Additional candidate enzymes are acetoacetyl-CoA synthetases from *Mus musculus* (Hasegawa et al., Biochim. Biophys. Acta 1779:414-419 (2008)) and *Homo sapiens* (Ohgami et al., Biochem. Pharmacol. 65:989-994 (2003)) which naturally catalyze the ATP-dependant conversion of acetoacetate into acetoacetyl-CoA.

| Gene name | GI# | GenBank Accession # | Organism |
|---|---|---|---|
| Phl | 77019264 | CAJ15517.1 | *Penicillium chrysogenum* |
| phlB | 152002983 | ABS19624.1 | *Penicillium chrysogenum* |
| paaF | 22711873 | AAC24333.2 | *Pseudomonas putida* |
| AACS | 21313520 | NP_084486.1 | *Mus musculus* |
| AACS | 31982927 | NP_076417.2 | *Homo sapiens* |

The invention will now be described in more detail on the basis of the following nonlimiting examples and with reference to the accompanying figures.

EXAMPLES

Example 1

This experiment illustrates HMD/$CO_2$ pH equilibrium under changing conditions. In this example, a 10% w/w aqueous HMD solution was prepared (70% HMD purchased from Sigma Aldrich). The HMD solution was heated to 30° C. and initial pH recorded. Next, $CO_2$ (approximately 98% pure) was bubbled into the solution for 60 min while monitoring pH. The $CO_2$ sparge was stopped. Air was sparged into solution for 30 min while monitoring pH. The air sparge was kept on and the solution was heated to 80° C. for 40 min. The pH was measured by sampling 3 mL to a falcon tube and cooling to 30° C. The solution was heated to 88° C. for 20 min. The solution was cooled to 30° C. and a final pH recorded. The measured pH values are plotted in Graphs 1-1, 1-2 and 1-3, below. It was noted that the temperature probe on pH meter was reading 44.4° C. at 300 min. and cooled back down to 30° C. by the end of the 60 min. This was most likely caused by the exothermic acid/base reaction. This temperature, increase can also account for the nonlinearity in FIG. 27-29 because pH decreases with increasing temperature.

TABLE 1-1

| Conditions and pH response | | |
|---|---|---|
| Condition change | pH (temp. in ° C.) | Comments |
| Initial conditions | 12.25 (30) | pH probe calibrated at 22° C. |
| Sparge $CO_2$ for 60 min. at 30° C. | 7.96 (30) | |
| House air sparge for 30 min. at 30° C. | 8.23 (30) | 10 bubbles/sec. sparge rate |
| Heated to 80° C. for 30 min. w/ sparge | 10.49 (30) | pH measure in a sample cooled to 30° C. |
| Heated to 88° C. for 15 min. w/ sparge | 10.76 (30) 11.02 (22.5) | pH measured in a sample and after bulk cooled down. Readings agreed +/− 0.01 |
| Sat open to air over night | 10.78 (20.6) | Some decrease in pH overnight. |

Table 1-2 shows simulated molar ratio of $CO_2$:HMD based on pH. It can be observed that 1.8 equivalents of $CO_2$ go into solution very quickly. The rate of absorption starts to slow down significantly when 2 equivalents are reached.

TABLE 1-2

| HMD:$CO_2$ in solution for selected points based on pH simulation. | |
|---|---|
| pH | Simulated $CO_2$:HMD (molar ratio in solution) |
| 10.76 | 0.523 |
| 9.77 | 1.314 |
| 9.00 | 1.820 |
| 8.23 | 1.994 |
| 7.96 | 2.038 |
| 12.433 | Control for = 0.86M, pKw = 13.840 |

The results illustrate that air and heat can restore the pH all the way back up to 11.02. Extraction should be possible at this pH. Aeration during fermentation may be able to strip off some of the dissolved $CO_2$.

Example 2

This example reports the results of a simulated fermentation process. Briefly, $CO_2$ (approximately 98% pure) and HMD (70% HMD from Sigma Aldrich) were fed into an MM9 solution that had the following composition:
 0.68% (6.8 g/L) Disodium phosphate $Na_2HPO_4$
 0.3% (3 g/L) Monopotassium phosphate $KH_2PO_4$
 0.15%(1.5 g/L) Ammonium chloride $NH_4Cl$
 0.1% (1 g/L) Ammonium sulfate $(NH_4)_2SO_4$
 0.05% (0.5 g/L) Sodium chloride NaCl
The experimental conditions for this example are listed in Table 2-1.

TABLE 2-1

| Summary of Experimental conditions | | |
|---|---|---|
| Input | Number | Unit |
| Feed rate HMD | 0.6 | mL/min |
| Feed [HMD] | 1.16 | mol/L |
| Initial reactor volume | 0.6 | L |
| Total time of exp. | 24 | hours |
| Final solution volume | 1.464 | L |
| Final [HMD] | 0.685 | mol/L |
| Molar ratio $CO_2$ | 3.2 | to 1 HMD |
| Temp. of inlet $CO_2$ | 21 | ° C. |
| $CO_2$ feed rate | 54.8 | mL/min |

TABLE 2-1-continued

Summary of Experimental conditions

| Input | Number | Unit |
|---|---|---|
| Air to $CO_2$ ratio | 4 | to 1 $CO_2$ |
| Air feed rate | 219 | mL/min |
| Total gas sparge rate | 274 | mL/min |

The measured pH of the solution and concentration of HMD added over time are set out in FIG. 30.

This feed rate used in this example corresponds to an average rate of 3.31 g/L/hr (a reasonable production rate in an industrial fermentation process). The final titer and feed concentration of HMD was confirmed by LCMS. The HMD and $CO_2$ reach a dynamic equilibrium around pH 8.5. As more HMD is added, more $CO_2$ is absorbed. The simulated HMD:$CO_2$ ratio is 1.95 for pH=8.53. This ratio indicates that the major species in solution is the $HMD^{2+}(HCO_3)_2$ salt (hexamethylenediamine bis-bicarbonate). FIGS. 31 and 32 illustrate the relative concentration of species as a function of pH for HMD and $H_2CO_3$, respectively.

At pH 8.5 (dashed, black line) the major species in solution are the diprotonated HMD and bicarbonate. A minority presence of HMD-carbamate may be present as well.

Example 3

This example demonstrates the generation of HMD, as the free base, from the protonated and/or carbonate/carbamate compounds formed by contacting an aqueous solution of HMD with $CO_2$ gas, where the aqueous solution was MM9 medium.

A 250 mL four-neck flask was fitted With a condenser, temperature probe, and air sparge needle. The system was open to air through the top of the condenser. The feed was an aqueous HMD solution in MM9 where pH was adjusted to 8.68 with CO2. The feed solution was analyzed for HMD concentration by LCMS ad the pH was measured. The solution was sparged with air and refluxed at 85° C. for three hours. The resulting solution's pH was taken and the concentration of HMD measured by LCMS.

TABLE 3-1

Summary of regeneration results

| Stream | pH | [HDM] mol/L | $CO_2$:HMD ratio* |
|---|---|---|---|
| Feed | 8.68 @ 21.7° C. | 834.0 | 1.91 |

TABLE 3-1-continued

Summary of regeneration results

| Stream | pH | [HDM] mol/L | $CO_2$:HMD ratio* |
|---|---|---|---|
| Product | 11.26 @ 23.5° C. | 954.7 | 0.277 |

*Based on calculation from pH.

The positive pH change from 8.68 to 11.26 shown in Table 3-1 indicates that $CO_2$ was stripped out of solution. The concentration increased slightly as some water escaped through the condenser and the solution was concentrated. The fraction of HMD in free base form at pH 11.26 is 57%.

Example 4

The example describes the solvent extraction of HMD from the $CO_2$ stripped solution prepared in Example 3 above as well as extracting HMD from an aqueous solution without pH adjustment as a control for solvent performance. The following protocol was used in this example:

The pH of the aqueous feed was measured. In a 50 mL falcon tube, 20 g of solvent was mixed with 20 g of feed. This combination was further aggressively mixed in the falcon tube for 5 minutes and vortexed for 1 minute. The tube with the mixed solvent and feed was allowed to settle until phase separation was complete. The volume of the bottom, aqueous layer was recorded. A sample of the top layer was carefully pipetted out the top layer. A sample the bottom layer was also obtained and the pH of the bottom layer measured. The recovery, distribution coefficients and selectivity based on mass balance were calculated.

The extraction data for three solvents extracting HMD from water are set out in Table 4-1.

TABLE 4-1

Results of solvent screening. HMD in deionized (DI) water. [HMD] = 835 mM

| Solvent used* | % Solubility | pH before | pH after | % water in extract | Selectivity | % recovery |
|---|---|---|---|---|---|---|
| 1-hexanol | 0.59 | 12.70 | 12.31 | 11.68 | 10.76 | 66.4 |
| Isopentanol | 2.8 | 12.70 | 12.16 | 9.08 | 19.07 | 71.4 |
| Cyclohexanol | 3.6 | 12.70 | 12.36 | 16.65 | 8.13 | 70.9 |
| Hexane | $9.4 \times 10^{-4}$ | 12.55 | 12.54 | <0.001 | >1,000 | 9.1 |

*All solvents were received from Sigma Aldrich at >97% purity

Based on the screening reported in Table 4-1, 1-hexanol was initially used for extracting the product of the HMD regeneration solution prepared in Example 3 above because it has the lower water solubility than isopentanol and cyclohexanol. Alkanes, specifically hexane, were screened and subsequently tested due to extremely low water solubility. Hexane extracted little if any water and provided reasonable recovery of the available free base.

Table 4-2 illustrates that with 1:1 solvent to feed ratio, HMD may be extracted in 25.8% overall recovery or 4% in the case of hexane. Based on the pH before extraction, only 60% of free base HMD is available. Thus, approximately 43% of the available free base HMD was extracted by the solvent 1-hexanol and about 7% by hexane. Hexane extracted little if any water and provided reasonable recovery of the available free base.

TABLE 4-2

Results of extracting stripped solution from "regeneration experiment." [HMD] = 955 mM

| Solvent used | % Solubility | pH before | pH after | % water in extract | Selectivity | % recovery |
|---|---|---|---|---|---|---|
| 1-hexanol | 0.59 | 11.44 | 11.02 | 9.02 | 2.70 | 25.8 |
| Hexane | 9.4 × 10−4 | 11.48 | 11.42 | <0.001 | >1,000 | 4.0 |

Example 5

Comparative Example

When a modeled HMD fermentation was controlled to a pH 7 with H2SO4, assuming 88% of glucose is converted to HMD on a mass basis, and a final HMD titer of 116 g/L, 0.843 g H2SO4 per g HMD is needed to maintain the pH at 7. Due to the amount of sulfuric acid used, carbon dioxide is not readily absorbed. This resulted in a final DIC/TDCA value of less than 0.5%. The fermentation model takes into account, among other things, cellular growth and respiration, byproduct formation, and media composition needed.

Example 5A

When an HMD fermentation was modeled at a pH of 8.5, assuming 88% of glucose is converted to HMD on a mass basis, and a final HMD titer of 116 g/L, no sulfuric acid is needed to maintain the pH of 8.5 (based on experimental results). Carbon dioxide is readily absorbed by the HMD. During the seed fermentation, the DIC/TDCA rose from <1% to approximately 54%. During the product fermentation, the value rose from approximately 54% to approximately 96%. The fermentation model takes into account, among other things, cellular growth and respiration, byproduct formation, and media composition needed.

Example 5B

When a modeled HMD fermentation is controlled to a pH of 7 with only CO2, assuming 88% of glucose is converted to HMD on a mass basis, and a final HMD titer of 116 g/L, It is shown that 2.4 moles of CO2 would need to be absorbed per mole of HMD. It has been experimentally shown in other examples that a pH of 7 can be reached with CO2 as the only acid used in pH control. During the seed fermentation model, the DIC/TDCA rose from <1% to approximately 82%. During the product fermentation model, the value rose from approximately 82% to approximately 97%. The fermentation model takes into account, among other things, cellular growth and respiration, byproduct formation, and media composition needed.

Example 6

Solvents such as alkanes were evaluated as suitable solvents for HMD free base recovery from aqueous solutions. See FIGS. 33 and 34. ASPEN (Aspen Plus ver 8.6; Aspen Technology, Inc., USA) software was used to model percent HMD recovered from a 50% aqueous solution of HMD by solvent extraction with hexane or heptane. The components included in the Aspen model were water, HMD, DIC (dissolved inorganic carbon), and solvent (hexane or heptane). An electrolyte NRTL model (ENRTL-RK) in ASPEN was used. A 50% HMD solution was modeled since that is an attainable concentration, especially using the methods described herein for water and CO2 removal, and is believed to be a concentration that avoids or reduces precipitation of HMD. For the model CO2 content in the 50% HMD solution was 0.3%. However, as the efficiency of solvent extraction increases with higher HMD concentrations, the HMD concentration limit for solvent extraction may be even higher.

In this example the extraction column had 10 theoretical stages. In this model the HMD comprised about 96.6% free base (solvent extractable form), thus the plotted values slightly underestimate the percent recovery of the recoverable form of HMD. These in silico modeling results demonstrate that alkanes can be effective solvents for HMD recovery from aqueous solutions at a range of solvent to HMD solution ratios.

The efficiency of solvent extraction increases with decrease in DIC concentration as shown below, supporting the importance of CO2 removal. DIC decrease results in higher pH and higher concentration of recoverable free base form.

Example 7

ASPEN Plus was used to model the use of either a water evaporator (a multi-effect evaporator) or a steam stripping column alone to achieve water and CO2 removal prior to HMD recovery. Conditions were as above; the components included in the ASPEN model were water, HMD, DIC species and hexane; an electrolyte NRTL model was used. While either step can be removed, and despite increasing electricity and steam usage in the evaporator when more water is evaporated, a savings in utility costs is realized with use of the evaporator because it is more efficient at removing water than the stripping column. The figure below (FIG. 35) shows steam and electricity usages as a function of total water removed when no stripping column is present. The plotted utility costs are for the evaporator step. The maximum ("Max") steam and electricity usage refer to the point where a 50% HMD by weight aqueous solution was achieved. As mentioned above this HMD concentration was selected for the model as it is believed suitable for extraction, avoiding further water and $CO_2$ removal which could lead to precipitate formation as the solution is concentrated. As the efficiency of solvent extraction increases with higher HMD concentrations, further concentration may be useful.

The figure below (FIG. 36) demonstrates steam usage in a stripping column in the case where no evaporator is present. A concentration limit is a 50% by weight HMD solution. As more water is evaporated from the feed, the duty and steam usage of the reboiler increases significantly. However, this is partially offset by the lower capital cost of a stripping column compared to an evaporation unit. The "Max" point on the FIG. 36 indicates the point where the 50% HMD solution is obtained.

Example 8

Preparation of an HMDA Producing Microbiol Organism Having Carbonic Anhydrase

*Escherichia coli* is used as a target organism to engineer to produce HMDA having nucleic acids encoding the enzymes utilized in the HMDA pathway and carbonic anhydrase.

The gene encoding a *Desulfovibrio vulgaris* (GenBank accession ACL09337.1 GI:218758438, SEQ ID) is codonoptimized for expression in *E. coli* and is cloned into an expression vector under the control of a constitutive promoter. This vector also contains an origin of replication and an antibiotic resistance gene. Also cloned into an expression vector or integrated into the host, *E. coli* in this example, are genes encoding enzymes for production of a diamine, e.g, HMD.

The resulting plasmids are transformed into *E. coli*, for example MG1655 or ATCC 8739, by chemical transformation or electroporation. For chemical transformation, cells are grown to mid-log growth phase, as determined by the optical density at 600 nm (0.5-0.8). The cells are harvested, washed and finally treated with CaCl2). To chemically transform these *E. coli* cells, purified plasmid DNA is allowed to mix with the cell suspension in a microcentrifuge tube on ice. A heat shock is applied to the mixture and followed by a 30-60 minute recovery incubation in rich culture medium. For electroporation, *E. coli* cells grown to mid-log growth phase are washed with water several times and finally resuspended into 10% glycerol solution. To electroporate DNA into these cells, a mixture of cells and DNA is pipetted into a disposable plastic cuvette containing electrodes. A short electric pulse is then applied to the cells to form small holes in the membrane where DNA could enter. The cell suspension is then incubated with rich liquid medium followed by plating on solid agar plates. Detailed protocol is described in Molecular Cloning: A Laboratory Manual Third Edition, Sambrook and Russell, 2001, Cold Spring Harbor Laboratory Press, 3rd Edition.

The resulting genetically engineered *E. coli* is cultured in glucose-containing medium following procedures well known in the art (see, for example, Sambrook et al., supra, 2001). The expression of the carbonic anhydrase and HMDA genes are corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce carbonic anhydrase can be confirmed using phenolphtheleine pH indicator to monitor pH change as carbonic anhydrase converts carbonate to $CO_2$ and the resulting pH of the solution containing the DA increases. The color change of phenolphtheleine can be monitored by absorbance at 550 nm. An assay is conducted by adding 300 mM-1000 mM DA to a cell lysate or the extracellular media with 300 mM-400 mM $KHCO_3$ and 400 μM-1100 μM phenolphthalein (Alvizo, et. al. 2014 PNAS 111(46): 16436-16441). Another assay for carbonic anhydrase activity is a colorimetric assay using 4-nitrophenylacetate as a substrate; 3 mM 4-nitrophenylacetate (Verpoorte et. al. 1967 J. Biol. Chem. 242: 4221-4229. Carbonic anhydrase can alas be monitored by production of CO2. HMD can be confirmed by HPLC.

What is claimed:

1. A process for diamine (DA) production comprising the steps of:
a) culturing a genetically engineered microorganism comprising a diamine (DA) synthesis pathway selected from the group consisting of hexamethylenediamine, cadaverine, putrescine, ethylenediamine and heptamethylenediamine with at least one exogenous nucleic acid encoding at least one enzyme of the DA synthesis pathway for producing a DA in medium under suitable conditions and for a sufficient period of time to produce DA and form one or more of DA carbonate, DA bicarbonate, and/or DA bis-bicarbonate in a cultured medium and a carbonic anhydrase in sufficient amount to (a) enhance the formation of the DA carbonate, DA bicarbonate, and/or, DA bis-bicarbonate by converting carbon dioxide to a bicarbonate and/or carbonate ions, (b) enhance the release of carbon dioxide from a solution of DA carbonate, DA bicarbonate, and/or DA bis-bicarbonate by converting a bicarbonate and/or carbonate ions to carbon dioxide, or (c) both (a) and (b);
wherein
i) carbon dioxide, carbonate, bicarbonate or carbonic acid predominantly control pH of the medium;
ii) percent dissolved inorganic carbon (DIC) in the medium is greater than or equal to 40%; and the DIC is determined by the formula:

DIC/TDCA×100 where TDCA is the Total Dissolved Counter Anions and is the sum of DIC and other anions; or
iii) at least 40% of diamine species in the medium comprises one or more of DA carbonate, DA bicarbonate, and/or DA bis-bicarbonate;
b) converting at least one or more of the DA carbonate, DA bicarbonate, and/or DA bis-bicarbonate into DA free base and carbon dioxide; and
c) isolating the DA free base.

2. The process of claim 1, further comprising removing solids from the cultured medium to form the DA carbonate, DA bicarbonate, and/or DA bis-bicarbonate.

3. The process of claim 1, further comprising removing water from the DA free base mixture and optional recycling water to a fermenter.

4. The process of claim 1, further comprising extracting the DA free base with organic solvent in an extractor to form an extracted DA free base solution and aqueous raffinate, and optionally recycling the aqueous raffinate to the extractor.

5. The process of claim 1, further comprising distilling the DA free base to form purified DA free base and organic solvent, optionally recycling the solvent to the extractor, and optionally removing undesired impurities.

6. The process of claim 1, further comprising adding an aqueous base to remove the DA carbonate, DA bicarbonate, and/or DA bis-bicarbonate from the DA free base.

7. The process of claim 1, wherein ≥50% to ≤99% of the diamine in the medium comprises one or more of a DA carbonate, DA bicarbonate, and/or DA bis-bicarbonate.

8. The process of claim 1, wherein the genetically engineered microorganism further forms one or more of carbon dioxide, carbonate, bicarbonate or carbonic acid.

9. The process claim 1, wherein one or more of carbon dioxide, carbonate, bicarbonate or carbonic acid is externally added to the medium.

10. The process claim 1, wherein the converting at least one or more of the DA carbonate, DA bicarbonate, and/or DA bis-bicarbonate into DA free base and carbon dioxide is by heating.

\* \* \* \* \*